(12) United States Patent
Askew et al.

(10) Patent No.: US 6,413,955 B1
(45) Date of Patent: Jul. 2, 2002

(54) INTEGRIN RECEPTOR ANTAGONISTS

(75) Inventors: Ben C. Askew, Newbury Park, CA (US); Garry R. Smith, Limerick, PA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/677,677

(22) Filed: Oct. 2, 2000

Related U.S. Application Data
(60) Provisional application No. 60/157,490, filed on Oct. 4, 1999.

(51) Int. Cl.[7] ............... A61K 31/55; C07D 213/02; C07D 403/02; C07D 207/00
(52) U.S. Cl. ............ 514/213.01; 514/300; 546/1; 546/112; 546/122; 546/193; 546/548; 546/543
(58) Field of Search .................. 514/300, 213.01; 546/1, 122, 193, 112; 548/543

(56) References Cited

U.S. PATENT DOCUMENTS

| | | | |
|---|---|---|---|
| 5,455,243 A | 10/1995 | Duggan et al. | 514/218 |
| 5,981,546 A | 11/1999 | Duggan et al. | 514/300 |
| 6,017,926 A | 1/2000 | Askew et al. | 514/300 |
| 6,066,648 A | 5/2000 | Duggan et al. | 514/300 |

FOREIGN PATENT DOCUMENTS

| | | |
|---|---|---|
| EP | 0 796 855 | 9/1997 |
| WO | WO 98/08840 | 3/1998 |
| WO | WO 98/18460 | 5/1998 |
| WO | WO 99/30709 | 6/1999 |
| WO | 9930709 * | 6/1999 |
| WO | WO 99/30713 | 6/1999 |
| WO | WO 99/31061 | 6/1999 |
| WO | WO 99/31099 | 6/1999 |
| WO | WO 00/09503 | 2/2000 |
| WO | 0009503 * | 2/2000 |

OTHER PUBLICATIONS

Duggan M., et al., "Ligands to the integrin receptor $\alpha v \beta 3$", *Expert Opinion on Therapeutic Patents,* vol. 10, pp. 1367–1383 (2000).

Miller, W. H., et al., "Identification and in vivo efficacy of small-molecule antagonists of integrin $\alpha v \beta 3$ (the vironectin receptor)", *Drug Discovery Today,* vol. 5, pp 397–408 (2000).

Gowen, M., et al., "Emerging therapies for osteoporosis", *Emerging Drugs,* vol. 5, pp 1–43 (2000).

Kerr, J. S., et al., "Small molecule $\alpha v$ integrin antagonists: novel anticancer agents", *Expert Opinion on Investigational Drugs,* vol. 9, pp 1271–1279 (2000).

* cited by examiner

Primary Examiner—Mukund J. Shah
Assistant Examiner—Sudhaker B. Patel
(74) Attorney, Agent, or Firm—Philippe L. Durette; Melvin Winokur

(57) ABSTRACT

The present invention relates to compounds and derivatives thereof, their synthesis, and their use as vitronectin receptor antagonists. More particularly, the compounds of the present invention are antagonists of the integrin receptors $\alpha v \beta 3$ and/or $\alpha v \beta 5$ and are useful for inhibiting bone resorption, treating and preventing osteoporosis, and inhibiting vascular restenosis, diabetic retinopathy, macular degeneration, angiogenesis, atherosclerosis, inflammatory arthritis, cancer, and metastatic tumor growth.

21 Claims, No Drawings

INTEGRIN RECEPTOR ANTAGONISTS

CROSS-REFERENCE TO RELATED APPLICATIONS

The present application claims priority of U.S. provisional application Ser. No. 60/157,490, filed Oct. 4, 1999, the contents of which are hereby incorporated by reference.

FIELD OF THE INVENTION

The present invention relates to compounds and derivatives thereof, their synthesis, and their use as integrin receptor antagonists. More particularly, the compounds of the present invention are antagonists of the integrin receptors $\alpha v\beta 3$ and/or $\alpha v\beta 5$ and are useful for inhibiting bone resorption, treating and preventing osteoporosis, and inhibiting vascular restenosis, diabetic retinopathy, macular degeneration, angiogenesis, atherosclerosis, inflammatory arthritis, cancer, and metastatic tumor growth.

BACKGROUND OF THE INVENTION

It is believed that a wide variety of disease states and conditions can be mediated by acting on integrin receptors and that integrin receptor antagonists represent a useful class of drugs. Integrin receptors are heterodimeric transmembrane receptors through which cells attach to and communicate with extracellular matrices and other cells. (See S. B. Rodan and G. A. Rodan, "Integrin Function In Osteoclasts", *Journal of Endocrinology*, Vol. 154, S47–S56 (1997), which is incorporated by reference herein in its entirety).

In one aspect of the present invention, the compounds herein are useful for inhibiting bone resorption. Bone resorption is mediated by the action of cells known as osteoclasts. Osteoclasts are large multinucleated cells of up to about 400 mm in diameter that resorb mineralized tissue, chiefly calcium carbonate and calcium phosphate, in vertebrates. Osteoclasts are actively motile cells that migrate along the surface of bone, and can bind to bone, secrete necessary acids and proteases, thereby causing the actual resorption of mineralized tissue from the bone. More specifically, osteoclasts are believed to exist in at least two physiological states, i.e. the secretory state and the migratory or motile state. In the secretory state, osteoclasts are flat, attach to the bone matrix via a tight attachment zone (sealing zone), become highly polarized, form a ruffled border, and secrete lysosomal enzymes and protons to resorb bone. The adhesion of osteoclasts to bone surfaces is an important initial step in bone resorption. In the migratory or motile state, the osteoclasts migrate across bone matrix and do not take part in resorption until they again attach to bone.

Integrins are involved in osteoclast attachment, activation and migration. The most abundant integrin on osteoclasts, e.g., on rat, chicken, mouse and human osteoclasts is $\alpha v\beta 3$, which belongs to the vitronectin subclass of integrin receptors, and which is thought to interact in bone with matrix proteins that contain the RGD sequence. Antibodies to $\alpha v\beta 3$ block bone resorption in vitro indicating that this integrin plays a key role in the resorptive process. There is increasing evidence to suggest that $\alpha v\beta 3$ ligands can be used effectively to inhibit osteoclast mediated bone resorption in vivo in mammals.

The current major bone diseases of public concern are osteoporosis, hypercalcemia of malignancy, osteopenia due to bone metastases, periodontal disease, hyperparathyroidism, periarticular erosions in rheumatoid arthritis, Paget's disease, immobilization-induced osteopenia, and glucocorticoid-induced osteoporosis. All of these conditions are characterized by bone loss, resulting from an imbalance between bone resorption, i.e. breakdown, and bone formation, which continues throughout life at the rate of about 14% per year on the average. However, the rate of bone turnover differs from site to site; for example, it is higher in the trabecular bone of the vertebrae and the alveolar bone in the jaws than in the cortices of the long bones. The potential for bone loss is directly related to turnover and can amount to over 5% per year in vertebrae immediately following menopause, a condition which leads to increased fracture risk.

In the United States, there are currently about 20 million people with detectable fractures of the vertebrae due to osteoporosis. In addition, there are about 250,000 hip fractures per year attributed to osteoporosis. This clinical situation is associated with a 12% mortality rate within the first two years, while 30% of the patients require nursing home care after the fracture.

Individuals suffering from all the conditions listed above would benefit from treatment with agents which inhibit bone resorption.

Additionally, $\alpha v\beta 3$ ligands have been found to be useful in treating and/or inhibiting restenosis, i.e. recurrence of stenosis after corrective surgery on the heart valve, atherosclerosis, diabetic retinopathy, macular degeneration, and angiogenesis, i.e. formation of new blood vessels. Moreover, it has been postulated that the growth of tumors depends on an adequate blood supply, which in turn is dependent on the growth of new vessels into the tumor; thus, inhibition of angiogenesis can cause tumor regression in animal models. (See *Harrison's Principles of Internal Medicine*, 12$^{th}$ ed., 1991, which is incorporated by reference herein in its entirety). Therefore, $\alpha v\beta 3$ antagonists which inhibit angiogenesis can be useful in the treatment of cancer by inhibiting tumor growth. (See, e.g., Brooks et al., *Cell*, 79:1157–1164 (1994), which is incorporated by reference herein in its entirety).

Moreover, compounds of this invention can also inhibit neovascularization by acting as antagonists of the integrin receptor, $\alpha v\beta 5$, which also belongs to the vitronectin subclass. A monoclonal antibody for $\alpha v\beta 5$ has been shown to inhibit VFGF-induced angiogenesis in rabbit cornea and the chick chorioallantoic membrane model. (See M. C. Friedlander, et al., *Science* 270, 1500–1502, 1995, which is incorporated by reference herein in its entirety). Thus, compounds that antagonize $\alpha v\beta 5$ are useful for treating and preventing macular degeneration, diabetic retinopathy, cancer, and metastatic tumor growth.

Evidence has also been presented suggesting that angiogenesis is a central factor in the initiation and persistence of arthritic disease, and that the vascular integrin $\alpha v\beta 3$ may be a preferred target in inflammatory arthritis. Therefore, $\alpha v\beta 3$ antagonists which inhibit angiogenesis may represent a novel therapeutic approach to the treatment of arthritic disease, such as rheumatoid arthritis (see C. M. Storgard, et al., "Decreased angiogenesis and arthritic disease in rabbits treated with an $\alpha v\beta 3$ antagonist," *J. Clin. Invest.*, 103: 47–54 (1999), which is incorporated by reference in its entirety).

Additionally, compounds of the instant invention can inhibit angiogenesis and inflammation by acting as antagonists of $\alpha v$ integrin receptors associated with other $\beta$ subunits, suh as $\alpha v\beta 6$ and $\alpha v\beta 8$ (See, for example, Melpo Christofidou-Solomidou, et al., *Expression and Function of Endothelial Cell $\alpha v$ Integrin Receptors in Wound-Induced*

Human Angiogensis in Human Skin/SCID Mice Chimeras, American Journal of Pathology, Vol. 151, No. 4 pp.975–83 (October 1997) and Xiao-Zhu Huang, et al., *Inactivation of the Integrin β6 Subunit Gene Reveals a Role of Epithelial Integrins in Regulating Inflammation in the Lungs and Skin*, Journal of Cell Biology, Vol. 133, No. 4 pp.921–28 (May 1996), which are incorporated by reference herein in their entirety).

In addition, certain compounds of this invention antagonize both the αvβ3 and αvβ5 receptors. These compounds, referred to as "dual αvβ3/αvβ5 antagonists," are useful for inhibiting bone resorption, treating and preventing osteoporosis, and inhibiting vascular restenosis, diabetic retinopathy, macular degeneration, angiogenesis, atherosclerosis, inflammatory arthritis, cancer, and metastatic tumor growth.

It is therefore an object of the present invention to provide compounds which are useful as integrin receptor antagonists.

It is another object of the present invention to provide compounds which are useful as αvβ3 receptor antagonists.

It is another object of the present invention to provide compounds which are useful as αvβ5 receptor antagonists.

It is another object of the present invention to provide compounds which are useful as dual αvβ3/αvβ5 receptor antagonists.

It is another object of the present invention to provide pharmaceutical compositions comprising integrin receptor antagonists.

It is another object of the present invention to provide methods for making the pharmaceutical compositions of the present invention.

It is another object of the present invention to provide methods for eliciting an integrin receptor antagonizing effect in a mammal in need thereof by administering the compounds and pharmaceutical compositions of the present invention.

It is another object of the present invention to provide compounds and pharmaceutical compositions useful for inhibiting bone resorption, restenosis, atherosclerosis, inflammatory arthritis, diabetic retinopathy, macular degeneration, angiogenesis, cancer, and metastatic tumor growth.

It is another object of the present invention to provide compounds and pharmaceutical compositions useful for treating osteoporosis.

It is another object of the present invention to provide methods for inhibiting bone resorption, restenosis, atherosclerosis, inflammatory arthritis, diabetic retinopathy, macular degeneration, angiogenesis, cancer, and metastatic tumor growth.

It is another object of the present invention to provide methods for treating osteoporosis.

These and other objects will become readily apparent from the detailed description which follows.

SUMMARY OF THE INVENTION

The present invention relates to compounds of the formula

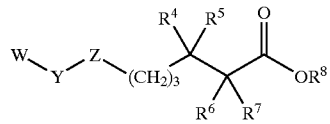

wherein any methylene ($CH_2$) carbon atom of the propylene $[(CH_2)_3]$ chain in the formula can be independently substituted by one or two $R^3$ substituents;

W is selected from the group consisting of
 a 5- or 6-membered monocyclic aromatic or nonaromatic ring system having 1, 2, 3 or 4 heteroatoms selected from the group consisting of N, O, and S wherein the ring nitrogen atoms are unsubstituted or substituted with one $R^1$ substituent and the ring carbon atoms are unsubstituted or substituted with one or two $R^1$ substituents, and
 a 9- to 14-membered polycyclic ring system, wherein the polycyclic ring system has 1, 2, 3 or 4 heteroatoms selected from the group consisting of N, O, and S, and wherein the ring nitrogen atoms are unsubstituted or substituted with one $R^1$ substituent and the ring carbon atoms are unsubstituted or substituted with one or two $R^1$ substituents;

Y is selected from the group consisting of
 —$(CH_2)_m$—,
 —$(CH_2)_m$—O—$(CH_2)_n$—,
 —$(CH_2)_m$—$NR^2$—$(CH_2)_n$—,
 —$(CH_2)_m$—S—$(CH_2)_n$—,
 —$(CH_2)_m$—SO—$(CH_2)_n$—,
 —$(CH_2)_m$—O—$(CH_2)_n$—,
 —$(CH_2)_m$—O—$(CH_2)_n$—O—$(CH_2)_p$—,
 —$(CH_2)_m$—O—$(CH_2)_n$—$NR^2$—$(CH_2)_p$—,
 —$(CH_2)_m$—$NR^2$—$(CH_2)_n$—$NR^2$—$(CH_2)_p$—,
 —$(CH_2)_m$—O—$(CH_2)_n$—S—$(CH_2)_p$—,
 —$(CH_2)_m$—S—$(CH_2)_n$—S—$(CH_2)_p$—,
 —$(CH_2)_m$—$NR^2$—$(CH_2)_n$—S—$(CH_2)_p$—,
 —$(CH_2)_m$—$NR^2$—$(CH_2)_n$—O—$(CH_2)_p$—,
 —$(CH_2)_m$—S—$(CH_2)_n$—O—$(CH_2)_p$—, and
 —$(CH_2)_m$—S—$(CH_2)_n$—$NR^2$—$(CH_2)_p$—,
wherein any methylene ($CH_2$) carbon atom in Y, other than in $R^2$, can be substituted by one or two $R^3$ substituents;

Z is a 5- or 6-membered heterocyclic ring system having 1 to 3 heteroatoms selected from the group consisting of N, O, and S, and wherein the ring system is either unsubstituted or substituted with one or more substituents independently selected from the group consisting of $R^9$, such that two $R^9$ substituents, when on the same carbon atom, are taken together with the carbon atom to which they are attached to form a $C_3$–$C_6$ cycloalkyl group;

$R^1$ is independently selected from the group consisting of hydrogen, halogen, $C_{1-10}$ alkyl, $C_{3-8}$ cycloalkyl, $C_{3-8}$ cycloheteroalkyl, $C_{3-8}$ cycloalkyl $C_{1-6}$ alkyl, $C_{3-8}$ cycloheteroalkyl $C_{1-6}$ alkyl, aryl, aryl $C_{1-8}$ alkyl, amino, amino $C_{1-8}$ alkyl, $C_{1-3}$ acylamino, $C_{1-3}$ acylamino $C_{1-8}$ alkyl, $(C_{1-6}$ alkyl$)_p$amino, $(C_{1-6}$ alkyl$)_p$ amino $C_{1-8}$ alkyl, $C_{1-4}$ alkoxy, $C_{1-4}$ alkoxy $C_{1-6}$ alkyl, hydroxycarbonyl, hydroxycarbonyl $C_{1-6}$ alkyl, $C_{1-3}$ alkoxycarbonyl, $C_{1-3}$ alkoxycarbonyl $C_{1-6}$ alkyl, hydroxycarbonyl-$C_{1-6}$ alkyloxy, hydroxy, hydroxy $C_{1-6}$ alkyl, $C_{1-6}$ alkyloxy-$C_{1-6}$ alkyl, nitro, cyano, trifluoromethyl, trifluoromethoxy, trifluoroethoxy, $C_{1-8}$ alkyl-S(O)$_p$, $(C_{1-8}$ alkyl$)_p$ aminocarbonyl, $C_{1-8}$ alkyloxycarbonylamino, ($C_{1-8}$ alkyl)$_p$aminocarbonyloxy, (aryl $C_{1-8}$ alkyl)$_p$amino, (aryl)$_p$amino, aryl $C_{1-8}$-alkylsulfonylamino, and $C_{1-8}$ alkylsulfonylamino;

or two $R^1$ substituents, when on the same carbon atom, are taken together with the carbon atom to which they are attached to form a carbonyl group;

each $R^2$ is independently selected from the group consisting of
hydrogen,
aryl,
aminocarbonyl,
$C_{3-8}$ cycloalkyl,
amino $C_{1-6}$ alkyl,
(aryl)$_p$aminocarbonyl,
(aryl $C_{1-5}$ alkyl)$_p$aminocarbonyl,
hydroxycarbonyl $C_{1-6}$ alkyl,
$C_{1-8}$ alkyl,
aryl $C_{1-6}$ alkyl,
($C_{1-6}$ alkyl)$_p$amino $C_{2-6}$ alkyl,
(aryl $C_{1-6}$ alkyl)$_p$amino $C_{2-6}$ alkyl,
$C_{1-8}$ alkylsulfonyl,
$C_{1-8}$ alkoxycarbonyl,
aryloxycarbonyl,
aryl $C_{1-8}$ alkoxycarbonyl,
$C_{1-8}$ alkylcarbonyl,
arylcarbonyl,
aryl $C_{1-6}$ alkylcarbonyl,
($C_{1-8}$ alkyl)$_p$aminocarbonyl,
aminosulfonyl,
$C_{1-8}$ alkylaminosulfonyl,
(aryl)$_p$aminosulfonyl,
(aryl $C_{1-8}$ alkyl)$_p$aminosulfony,
arylsulfonyl,
aryl$C_{1-6}$ alkylsulfonyl,
$C_{1-6}$ alkylthiocarbonyl,
arylthiocarbonyl, and
aryl $C_{1-6}$ alkylthiocarbonyl,
wherein any of the alkyl groups of $R^2$ are either unsubstituted or substituted with one to three $R^1$ substituents;

each $R^3$ is independently selected from the group consisting of
hydrogen,
aryl,
$C_{1-10}$ alkyl,
aryl-$(CH_2)_r$—O—$(CH_2)_s$—,
aryl-$(CH_2)_r$S(O)$_p$—$(CH_2)_s$—,
aryl-$(CH_2)_r$—C(O)—$(CH_2)_s$—,
aryl-$(CH_2)_r$—C(O)—N($R^2$)—$(CH_2)_s$—,
aryl-$(CH_2)_r$—N($R^2$)—C(O)—$(CH_2)_s$—,
aryl-$(CH_2)_r$—N($R^2$)—$(CH_2)_s$—,
halogen,
hydroxyl,
oxo,
trifluoromethyl,
$C_{1-8}$ alkylcarbonylamino,
aryl $C_{1-5}$ alkoxy,
$C_{1-5}$ alkoxycarbonyl,
($C_{1-8}$ alkyl)$_p$aminocarbonyl,
$C_{1-6}$ alkylcarbonyloxy,
$C_{3-8}$ cycloalkyl,
($C_{1-6}$ alkyl)$_p$amino,
amino $C_{-6}$ alkyl,
arylaminocarbonyl,
aryl $C_{1-5}$ alkylaminocarbonyl,
aminocarbonyl,
aminocarbonyl $C_{1-6}$ alkyl,
hydroxycarbonyl,
hydroxycarbonyl $C_{1-6}$ alkyl,
HC≡C—$(CH_2)_t$—,
$C_{1-6}$ alkyl-C≡C—$(CH_2)_t$—,
$C_{3-7}$ cycloalkyl-C≡C—$(CH_2)_t$—,
aryl-C≡C—$(CH_2)_t$—,
$C_{1-6}$ alkylaryl-C≡C—$(CH_2)_t$—,
$CH_2$=CH—$(CH_2)_t$—,
$C_{1-6}$ alkyl-CH=CH—$(CH_2)_t$—,
$C_{3-7}$ cycloalkyl-CH=CH—$(CH_2)_t$—,
aryl-CH=CH—$(CH_2)_t$—,
$C_{1-6}$ alkylaryl-CH=CH—$(CH_2)_t$—,
$C_{1-6}$ alkyl-$SO_2$—$(CH_2)_t$—,
$C_{1-6}$ alkylaryl-$SO_2$—$(CH_2)_t$—,
$C_{1-6}$ alkoxy,
aryl $C_{1-6}$ alkoxy,
aryl $C_{1-6}$ alkyl,
($C_{1-6}$ alkyl)$_p$amino $C_{1-6}$ alkyl,
(aryl)$_p$amino,
(aryl)$_p$amino $C_{1-6}$ alkyl,
(aryl $C_{1-6}$ alkyl)$_p$amino,
(aryl $C_{1-6}$ alkyl)$_p$amino $C_{1-6}$ alkyl,
arylcarbonyloxy,
aryl $C_{1-6}$ alkylcarbonyloxy,
($C_{1-6}$ alkyl)$_p$aminocarbonyloxy,
$C_{1-8}$ alkylsulfonylamino,
arylsulfonylamino,
$C_{1-8}$ alkylsulfonylamino $C_{1-6}$ alkyl,
arylsulfonylamino $C_{1-6}$ alkyl,
aryl $C_{1-6}$ alkylsulfonylamino,
aryl $C_{1-6}$ alkylsulfonylamino $C_{1-6}$ alkyl,
$C_{1-8}$ alkoxycarbonylamino,
$C_{1-8}$ alkoxycarbonylamino $C_{1-8}$ alkyl,
aryloxycarbonylamino $C_{1-8}$ alkyl,
aryl $C_{1-8}$ alkoxycarbonylamino,
aryl $C_{1-8}$ alkoxycarbonylamino $C_{1-8}$ alkyl,
$C_{1-8}$ alkylcarbonylamino,
C1-8 alkylcarbonylamino $C_{1-6}$ alkyl,
arylcarbonylamino $C_{1-6}$ alkyl,
aryl $C_{1-6}$ alkylcarbonylamino,
aryl $C_{1-6}$ alkylcarbonylamino $C_{1-6}$ alkyl,
aminocarbonylamino $C_{1-6}$ alkyl,
($C_{1-8}$ alkyl)$_p$aminocarbonylamino,
($C_{1-8}$ alkyl)$_p$aminocarbonylamino $C_{1-6}$ alkyl,
(aryl)$_p$aminocarbonylamino $C_{1-6}$ alkyl,
(aryl $C_{1-8}$ alkyl)$_p$aminocarbonylamino,
(aryl $C_{1-8}$ alkyl)$_p$aminocarbonylamino $C_{1-6}$ alkyl,
aminosulfonylamino $C_{1-6}$ alkyl,
($C_{1-8}$ alkyl)$_p$aminosulfonyl amino,
($C_{1-8}$ alkyl)$_p$aminosulfonylamino $C_{1-6}$ alkyl,
(aryl)$_p$aminosulfonylamino $C_{1-6}$ alkyl,
(aryl $C_{1-8}$ alkyl)$_p$aminosulfonylamino,
(aryl $C_{1-8}$ alkyl)$_p$aminosulfonylamino $C_{1-6}$ alkyl,
$C_{1-6}$ alkylsulfonyl,
$C_{1-6}$ alkylsulfonyl $C_{1-6}$ alkyl,
arylsulfonyl $C_{1-6}$ alkyl,
aryl $C_{1-6}$ alkylsulfonyl,
aryl $C_{1-6}$ alkylsulfonyl $C_{1-6}$ alkyl,
$C_{1-6}$ alkylcarbonyl,
$C_{1-6}$ alkylcarbonyl $C_{1-6}$ alkyl,
arylcarbonyl $C_{1-6}$ alkyl,
aryl $C_{1-6}$ alkylcarbonyl,
aryl $C_{1-6}$ alkylcarbonyl $C_{1-6}$ alkyl,
$C_{1-6}$ alkylthiocarbonylamino,
$C_{1-6}$ alkylthiocarbonylamino $C_{1-6}$ alkyl,
arylthiocarbonylamino $C_{1-6}$ alkyl,
aryl $C_{1-6}$ alkylthiocarbonylamino, aryl $C_{1-6}$ alkylthiocarbonylamino $C_{1-6}$ alkyl,
$(C_{1-8}$ alkyl)$_p$aminocarbonyl $C_{1-6}$ alkyl,
(aryl)$_p$aminocarbonyl $C_{1-6}$ alkyl,
(aryl $C_{1-8}$ alkyl)$_p$aminocarbonyl, and
(aryl $C_{1-8}$ alkyl)$_p$aminocarbonyl $C_{1-6}$ alkyl,
or two $R^3$ substituents, when on the same carbon atom are taken together with the carbon atom to which they are attached to form a cyclopropyl group,
wherein any of the alkyl groups of $R^3$ are either unsubstituted or substituted with one to three $R^1$ substituents, and provided that each $R^3$ is selected such that in the resultant compound the carbon atom or atoms to which $R^3$ is attached is itself attached to no more than one heteroatom;
$R^4$ and $R^5$ are each independently selected from the group consisting of
hydrogen,
$C_{1-10}$ alkyl,
aryl,
aryl-$(CH_2)_r$—O—$(CH_2)_s$—,
aryl-$(CH_2)_r$S(O)$_p$—$(CH_2)_s$—,
aryl-$(CH_2)_r$—C(O)—$(CH_2)_s$—,
aryl-$(CH_2)_r$—C(O)—N($R^2$)—$(CH_2)_s$—,
aryl-$(CH_2)_r$—N($R^2$)—C(O)—$(CH_2)_s$—,
aryl-$(CH_2)_r$—N($R^2$)—$(CH_2)_s$—,
halogen,
hydroxyl,
$C_{1-8}$ alkylcarbonylamino,
aryl $C_{1-5}$ alkoxy,
$C_{1-5}$ alkoxycarbonyl,
$(C_{1-8}$ alkyl)$_p$aminocarbonyl,
$C_{1-6}$ alkylcarbonyloxy,
$C_{3-8}$ cycloalkyl,
$(C_{1-6}$ alkyl)$_p$amino,
amino $C_{1-6}$ alkyl,
arylaminocarbonyl,
aryl $C_{1-5}$ alkylaminocarbonyl,
aminocarbonyl,
aminocarbonyl $C_{1-6}$ alkyl,
hydroxycarbonyl,
hydroxycarbonyl $C_{1-6}$ alkyl,
HC≡C—$(CH_2)_t$—,
$C_{1-6}$ alkyl-C≡C—$(CH_2)_t$—,
$C_{3-7}$ cycloalkyl-C≡C—$(CH_2)_t$—,
aryl-C≡C—$(CH_2)_t$—,
$C_{1-6}$ alkylaryl-C≡C—$(CH_2)_t$—,
$CH_2$=CH—$(CH_2)_t$—,
$C_{1-6}$ alkyl-CH=CH—$(CH_2)_t$—,
$C_{3-7}$ cycloalkyl-CH=CH—$(CH_2)_t$—,
aryl-CH=CH—$(CH_2)_t$—,
$C_{1-6}$ alkylaryl-CH=CH—$(CH_2)_t$—,
$C_{1-6}$ alkyl-$SO_2$—$(CH_2)_t$—,
$C_{1-6}$ alkylaryl-$SO_2$—$(CH_2)_t$—,
$C_{1-6}$ alkoxy,
aryl $C_{1-6}$ alkoxy,
aryl $C_{1-6}$ alkyl,
$(C_{1-6}$ alkyl)$_p$amino $C_{1-6}$ alkyl,
(aryl)$_p$amino,
(aryl)$_p$amino $C_{1-6}$ alkyl,
(aryl $C_{1-6}$ alkyl)$_p$amino,
(aryl $C_{1-6}$ alkyl)$_p$amino $C_{1-6}$ alkyl,
arylcarbonyloxy,
aryl $C_{1-6}$ alkylcarbonyloxy,
$(C_{1-6}$ alkyl)$_p$aminocarbonyloxy,
$C_{1-8}$ alkylsulfonylamino,
arylsulfonylamino,
$C_{1-8}$ alkylsulfonylamino $C_{1-6}$ alkyl,
arylsulfonylamino $C_{1-6}$ alkyl,
aryl $C_{1-6}$ alkylsulfonylamino,
aryl $C_{1-6}$ alkylsulfonylamino $C_{1-6}$ alkyl,
$C_{1-8}$ alkoxycarbonylamino,
$C_{1-8}$ alkoxycarbonylamino $C_{1-8}$ alkyl,
aryloxycarbonylamino $C_{1-8}$ alkyl,
aryl $C_{1-8}$ alkoxycarbonylamino,
aryl $C_{1-8}$ alkoxycarbonylamino $C_{1-8}$ alkyl,
$C_{1-8}$ alkylcarbonylamino,
$C_{1-8}$ alkylcarbonylamino $C_{1-6}$ alkyl,
arylcarbonylamino $C_{1-6}$ alkyl,
aryl $C_{1-6}$ alkylcarbonylamino,
aryl $C_{1-6}$ alkylcarbonylamino $C_{1-6}$ alkyl,
aminocarbonylamino $C_{1-6}$ alkyl,
$(C_{1-8}$ alkyl)$_p$aminocarbonylamino,
$(C_{1-8}$ alkyl)$_p$aminocarbonylamino $C_{1-6}$ alky,
(aryl)$_p$aminocarbonylamino $C_{1-6}$ alkyl,
(aryl $C_{1-8}$ alkyl)$_p$aminocarbonylamino,
(aryl $C_{1-8}$ alkyl)$_p$aminocarbonylamino $C_{1-6}$ alkyl,
aminosulfonylamino $C_{1-6}$ alkyl,
$(C_{1-8}$ alkyl)$_p$aminosulfonylamino,
$(C_{1-8}$ alkyl)$_p$aminosulfonylamino $C_{1-6}$ alkyl,
(aryl)$_p$aminosulfonylamino $C_{1-6}$ alkyl,
(aryl $C_{1-8}$ alkyl)$_p$aminosulfonylamino,
(aryl $C_{1-8}$ alkyl)$_p$aminosulfonylamino $C_{1-6}$ alkyl,
$C_{1-6}$ alkylsulfonyl,
$C_{1-6}$ alkylsulfonyl $C_{1-6}$ alkyl,
arylsulfonyl $C_{1-6}$ alkyl,
aryl $C_{1-6}$ alkylsulfonyl,
aryl $C_{1-6}$ alkylsulfonyl $C_{1-6}$ alkyl,
$C_{1-6}$ alkylcarbonyl,
$C_{1-6}$ alkylcarbonyl $C_{1-6}$ alkyl,
arylcarbonyl $C_{1-6}$ alkyl,
aryl $C_{1-6}$ alkylcarbonyl,
aryl $C_{1-6}$ alkylcarbonyl $C_{1-6}$ alkyl,
$C_{1-6}$ alkylthiocarbonylamino,
$C_{1-6}$ alkylthiocarbonylamino C1-6 alkyl,
arylthiocarbonylamino $C_{1-6}$ alkyl,
aryl $C_{1-6}$ alkylthiocarbonylamino,
aryl $C_{1-6}$ alkylthiocarbonylamino $C_{1-6}$ alkyl,
$(C_{1-8}$ alkyl)$_p$aminocarbonyl $C_{1-6}$ alkyl,
(aryl)$_p$aminocarbonyl $C_{1-6}$ alkyl,
(aryl $C_{1-8}$ alkyl)$_p$aminocarbonyl, and
(aryl $C_{1-8}$ alkyl)$_p$aminocarbonyl $C_{1-6}$ alkyl;
or $R^4$ and $R^5$ are taken together with the carbon atom to which they are attached to form a carbonyl group,
wherein any of the alkyl groups of $R^4$ or $R^5$ are either unsubstituted or substituted with one to three $R^1$ substituents, and provided that each $R^4$ and $R^5$ are selected such that in the resultant compound the carbon atom to which $R^4$ and $R^5$ are attached is itself attached to no more than one heteroatom;
$R^6$ and $R^7$ are each independently selected from the group consisting of
hydrogen,
$C_{1-10}$ alkyl,
aryl,
aryl-$(CH_2)_r$—O—$(CH_2)_s$—,
aryl-$(CH_2)_r$—S(O)$_p$—$(CH_2)_s$—,
aryl-$(CH_2)_r$—C(O)—$(CH_2)_s$—,
aryl-$(CH_2)_r$—C(O)—N($R^2$)—$(CH_2)_s$—,
aryl-$(CH_2)_r$—N($R^2$)—C(O)—$(CH_2)_s$—,
aryl-$(CH_2)_r$—N($R^2$)—$(CH_2)_s$—,
halogen,
hydroxyl,
$C_{1-8}$ alkylcarbonylamino,
aryl $C_{1-5}$ alkoxy, $C_{1-5}$ alkoxycarbonyl,
$(C_{1-8}$ alkyl$)_p$aminocarbonyl,
$C_{1-6}$ alkylcarbonyloxy,
$C_{3-8}$ cycloalkyl,
$(C_{1-6}$ alkyl$)_p$amino,
amino $C_{1-6}$ alkyl,
arylaminocarbonyl,
aryl $C_{1-5}$ alkylaminocarbonyl,
aminocarbonyl,
aminocarbonyl $C_{1-6}$ alkyl,
hydroxycarbonyl,
hydroxycarbonyl $C_{1-6}$ alkyl,
$HC\equiv C-(CH_2)_t-$,
$C_{1-6}$ alkyl-$C\equiv C-(CH_2)_t-$,
$C_{3-7}$ cycloalkyl-$C\equiv C-(CH_2)_t-$,
aryl-$C\equiv C-(CH_2)_t-$,
$C_{1-6}$ alkylaryl-$C\equiv C-(CH_2)_t-$,
$CH_2=CH-(CH_2)_t-$,
$C_{1-6}$ alkyl-$CH=CH-(CH_2)_t-$,
$C_{3-7}$ cycloalkyl-$CH=CH-(CH_2)_t-$,
aryl-$CH=CH-(CH_2)_t-$,
$C_{1-6}$ alkylaryl-$CH=CH-(CH_2)_t-$,
$C_{1-6}$ alkyl-$SO_2-(CH_2)_t-$,
$C_{1-6}$ alkylaryl-$SO_2-(CH_2)_t-$,
$C_{1-6}$ alkoxy,
aryl $C_{1-6}$ alkoxy,
aryl $C_{1-6}$ alkyl,
$(C_{1-6}$ alkyl$)_p$amino $C_{1-6}$ alkyl,
(aryl$)_p$amino,
(aryl$)_p$amino $C_{1-6}$ alkyl,
(aryl $C_{1-6}$ alkyl$)_p$amino,
(aryl $C_{1-6}$ alkyl$)_p$amino $C_{1-6}$ alkyl,
arylcarbonyloxy,
aryl $C_{1-6}$ alkylcarbonyloxy,
$(C_{1-6}$ alkyl$)_p$aminocarbonyloxy,
$C_{1-8}$ alkylsulfonylamino,
arylcarbonylamino,
arylsulfonylamino,
$C_{1-8}$ alkylsulfonylamino $C_{1-6}$ alkyl,
arylsulfonylamino $C_{1-6}$ alkyl,
aryl $C_{1-6}$ alkylsulfonylamino,
aryl $C_{1-6}$ alkylsulfonylamino $C_{1-6}$ alkyl,
$C_{1-8}$ alkoxycarbonylamino,
$C_{1-8}$ alkoxycarbonylamino $C_{1-8}$ alkyl,
aryloxycarbonylamino $C_{1-8}$ alkyl,
aryl $C_{1-8}$ alkoxycarbonylamino,
aryl $C_{1-8}$ alkoxycarbonylamino $C_{1-8}$ alkyl,
$C_{1-8}$ alkylcarbonylamino $C_{1-6}$ alkyl,
arylcarbonylamino $C_{1-6}$ alkyl,
aryl $C_{1-6}$ alkylcarbonylamino,
aryl $C_{1-6}$ alkylcarbonylamino $C_{1-6}$ alkyl,
aminocarbonylamino $C_{1-6}$ alkyl,
$(C_{1-8}$ alkyl$)_p$aminocarbonylamino,
$(C_{1-8}$ alkyl$)_p$aminocarbonylamino $C_{1-6}$ alkyl,
(aryl$)_p$aminocarbonylamino $C_{1-6}$ alkyl,
arylaminocarbonylamino,
(aryl $C_{1-8}$ alkyl$)_p$aminocarbonylamino,
(aryl $C_{1-8}$ alkyl$)_p$aminocarbonylamino $C_{1-6}$ alkyl,
aminosulfonylamino $C_{1-6}$ alkyl,
$(C_{1-8}$ alkyl$)_p$aminosulfonylamino,
$(C_{1-8}$ alkyl$)_p$aminosulfonylamino $C_{1-6}$ alkyl,
(aryl$)_p$aminosulfonylamino $C_{1-6}$ alkyl,
(aryl $C_{1-8}$ alkyl$)_p$aminosulfonylamino,
(aryl $C_{1-8}$ alkyl$)_p$aminosulfonylamino $C_{1-6}$ alkyl,
$C_{1-6}$ alkylsulfonyl,
$C_{1-6}$ alkylsulfonyl $C_{1-6}$ alkyl,
arylsulfonyl $C_{1-6}$ alkyl,
aryl $C_{1-6}$ alkylsulfonyl,
aryl $C_{1-6}$ alkylsulfonyl $C_{1-6}$ alkyl,
$C_{1-6}$ alkylcarbonyl,
$C_{1-6}$ alkylcarbonyl $C_{1-6}$ alkyl,
arylcarbonyl $C_{1-6}$ alkyl,
aryl $C_{1-6}$ alkylcarbonyl,
aryl $C_{1-6}$ alkylcarbonyl $C_{1-6}$ alkyl,
$C_{1-6}$ alkylthiocarbonylamino,
$C_{1-6}$ alkylthiocarbonylamino $C_{1-6}$ alkyl,
arylthiocarbonylamino $C_{1-6}$ alkyl,
aryl $C_{1-6}$ alkylthiocarbonylamino,
aryl $C_{1-6}$ alkylthiocarbonylamino $C_{1-6}$ alkyl,
$(C_{1-8}$ alkyl$)_p$aminocarbonyl $C_{1-6}$ alkyl,
(aryl$)_p$aminocarbonyl $C_{1-6}$ alkyl,
(aryl $C_{1-8}$ alkyl$)_p$aminocarbonyl,
(aryl $C_{1-8}$ alkyl$)_p$aminocarbonyl $C_{1-6}$ alkyl, and
$C_{7-20}$ polycyclyl $C_{0-8}$ alkylsulfonylamino;
wherein any of the alkyl groups of $R^6$ and $R^7$ are either unsubstituted or substituted with one to three $R^1$ substituents, and provided that each $R^6$ and $R^7$ are selected such that in the resultant compound the carbon atom to which $R^6$ and $R^7$ are attached is itself attached to no more than one heteroatom;

$R^8$ is selected from the group consisting of
hydrogen,
$C_{1-8}$ alkyl,
aryl,
aryl $C_{1-8}$ alkyl,
$C_{1-8}$ alkylcarbonyloxy $C_{1-4}$ alkyl,
aryl $C_{1-8}$ alkylcarbonyloxy $C_{1-4}$ alkyl,
$C_{1-8}$ alkylaminocarbonylmethylene, and
$C_{1-8}$ dialkylaminocarbonylmethylene;

each $R^9$ is independently selected from the group consisting of hydrogen,
$C_{1-8}$ alkyl,
aryl,
halogen,
hydroxyl,
oxo,
aminocarbonyl,
$C_{3-8}$ cycloalkyl,
amino $C_{1-6}$ alkyl,
(aryl$)_p$aminocarbonyl,
hydroxycarbonyl,
(aryl $C_{1-5}$ alkyl$)_p$aminocarbonyl,
hydroxycarbonyl $C_{1-6}$ alkyl,
aryl $C_{1-6}$ alkyl,
$(C_{1-6}$ alkyl$)_p$amino $C_{1-6}$ alkyl,
(aryl $C_{1-6}$ alkyl$)_p$amino $C_{2-6}$ alkyl,
$C_{1-8}$ alkylsulfonyl,
$C_{1-8}$ alkoxycarbonyl,
aryloxycarbonyl,
aryl $C_{1-8}$ alkoxycarbonyl,
$C_{1-8}$ alkylcarbonyl,
arylcarbonyl,
aryl $C_{1-6}$ alkylcarbonyl,
$(C_{1-8}$ alkyl$)_p$aminocarbonyl,
aminosulfonyl,
$C_{1-8}$ alkylaminosulfonyl,
(aryl$)_p$aminosulfonyl,
(aryl $C_{1-8}$ alkyl$)_p$aminosulfonyl,
$C_{1-6}$ alkylsulfonyl,
arylsulfonyl,
aryl $C_{1-6}$ alkylsulfonyl,
aryl $C_{1-6}$ alkylcarbonyl,
$C_{1-6}$ alkylthiocarbonyl,
arylthiocarbonyl, aryl $C_{1-6}$ alkylthiocarbonyl,
aryl-$(CH_2)_r$—O—$(CH_2)_s$—,
aryl-$(CH_2)_r$S(O)$_p$—$(CH_2)_s$—,
aryl-$(CH_2)_r$—C(O)—$(CH_2)_s$—,
aryl-$(CH_2)_r$—C(O)—N($R^2$)—$(CH_2)_s$—,
aryl-$(CH_2)_r$—N($R^2$)—C(O)—$(CH_2)_s$—,
aryl-$(CH_2)_r$—N($R^2$)—$(CH_2)_s$—,
HC≡C—$(CH_2)_t$—,
$C_{1-6}$ alkyl-C≡C—$(CH_2)_t$—,
$C_{3-7}$ cycloalkyl-C≡C—$(CH_2)_t$—,
aryl-C≡C—$(CH_2)_t$—,
$C_{1-6}$ alkylaryl-C≡C—$(CH_2)_t$—,
$CH_2$=CH—$(CH_2)_t$—,
$C_{1-6}$ alkyl-CH=CH—$(CH_2)_t$—,
$C_{3-7}$ cycloalkyl-CH=CH—$(CH_2)_t$—,
aryl-CH=CH—$(CH_2)_t$—,
$C_{1-6}$ alkylaryl-CH=CH—$(CH_2)_t$—,
$C_{1-6}$ alkyl-$SO_2$—$(CH_2)_t$—,
$C_{1-6}$ alkylaryl-$SO_2$—$(CH_2)_t$—,
$C_{7-20}$ polycyclyl $C_{0-8}$ alkylsulfonylamino $C_{0-6}$ alkyl,
$C_{7-20}$ polycyclyl $C_{0-8}$ alkylcarbonylamino $C_{0-6}$ alkyl,
$C_{7-20}$ polycyclyl $C_{0-8}$ alkylaminosulfonyolamino $C_{0-6}$ alkyl,
$C_{7-20}$ polycyclyl $C_{0-8}$ alkylaminocarbonylamino $C_{0-6}$ alkyl,
$C_{7-20}$ polycyclyl $C_{0-8}$ alkyloxycarbonylamino $C_{0-6}$ alkyl,
$C_{1-8}$ alkylcarbonylamino,
aryl $C_{1-5}$ alkoxy,
$C_{1-5}$ alkoxycarbonyl,
$(C_{1-8}$ alkyl$)_p$aminocarbonyl,
$C_{1-6}$ alkylcarbonyloxy,
$(C_{1-6}$ alkyl$)_p$amino,
aminocarbonyl $C_{1-6}$ alkyl,
$C_{1-6}$ alkoxy,
aryl $C_{1-6}$ alkoxy,
(aryl)$_p$amino,
(aryl)$_p$amino $C_{1-6}$ alkyl,
(aryl $C_{1-6}$ alkyl)$_p$amino,
(aryl $C_{1-6}$ alkyl)$_p$amino $C_{1-6}$ alkyl,
arylcarbonyloxy,
aryl $C_{1-6}$ alkylcarbonyloxy,
$(C_{1-6}$ alkyl$)_p$aminocarbonyloxy,
$C_{1-8}$ alkylsulfonylamino,
arylsulfonylamino,
$C_{1-8}$ alkylsulfonylamino $C_{1-6}$ alkyl,
arylsulfonylamino $C_{1-6}$ alkyl,
aryl $C_{1-6}$ alkylsulfonylamino,
aryl $C_{1-6}$ alkylsulfonylamino $C_{1-6}$ alkyl,
$C_{1-8}$ alkoxycarbonylamino,
$C_{1-8}$ alkoxycarbonylamino $C_{1-8}$ alkyl,
aryloxycarbonylamino $C_{1-8}$ alkyl,
aryl $C_{1-8}$ alkoxycarbonylamino,
aryl $C_{1-8}$ alkoxycarbonylamino $C_{1-8}$ alkyl,
$C_{1-8}$ alkylcarbonylamino,
$C_{1-8}$ alkylcarbonylamino $C_{1-6}$ alkyl,
arylcarbonylamino $C_{1-6}$ alkyl,
aryl $C_{1-6}$ alkylcarbonylamino,
aryl $C_{1-6}$ alkylcarbonylamino $C_{1-6}$ alkyl,
aminocarbonylamino $C_{1-6}$ alkyl,
$(C_{1-8}$ alkyl$)_p$aminocarbonylamino,
$(C_{1-8}$ alkyl$)_p$aminocarbonylamino $C_{1-6}$ alkyl,
(aryl)$_p$aminocarbonylamino $C_{1-6}$ alkyl,
(aryl $C_{1-8}$ alkyl)$_p$aminocarbonylamino,
(aryl $C_{1-8}$ alkyl)$_p$aminocarbonylamino $C_{1-6}$ alkyl,
aminosulfonylamino $C_{1-6}$ alkyl,
$(C_{1-8}$ alkyl$)_p$aminosulfonylamino,
$(C_{1-8}$ alkyl$)_p$aminosulfonylamino $C_{1-6}$ alkyl,
(aryl)$_p$aminosulfonylamino $C_{1-6}$ alkyl,
(aryl $C_{1-8}$ alkyl)$_p$aminosulfonylamino,
(aryl $C_{1-8}$ alkyl)$_p$aminosulfonylamino $C_{1-6}$ alkyl,
$C_{1-6}$ alkylsulfonyl,
$C_{1-6}$ alkylsulfonyl $C_{1-6}$ alkyl,
arylsulfonyl $C_{1-6}$ alkyl,
aryl $C_{1-6}$ alkylsulfonyl,
aryl $C_{1-6}$ alkylsulfonyl $C_{1-6}$ alkyl,
$C_{1-6}$ alkylcarbonyl,
$C_{1-6}$ alkylcarbonyl $C_{1-6}$ alkyl,
arylcarbonyl $C_{1-6}$ alkyl,
aryl $C_{1-6}$ alkylcarbonyl,
aryl $C_{1-6}$ alkylcarbonyl $C_{1-6}$ alkyl,
$C_{1-6}$ alkylthiocarbonylamino,
$C_{1-6}$ alkylthiocarbonylamino $C_{1-6}$ alkyl,
arylthiocarbonylarmino $C_{1-6}$ alkyl,
aryl $C_{1-6}$ alkylthiocarbonylamino,
aryl $C_{1-6}$ alkylthiocarbonylamino $C_{1-6}$ alkyl,
$(C_{1-8}$ alkyl$)_p$aminocarbonyl $C_{1-6}$ alkyl,
(aryl)$_p$aminocarbonyl $C_{1-6}$ alkyl,
(aryl $C_{1-8}$ alkyl)$_p$aminocarbonyl, and
(aryl $C_{1-8}$ alkyl)$_p$aminocarbonyl $C_{1-6}$ alkyl;

and wherein any of the alkyl groups of $R^9$ are either unsubstituted or substituted with one to three $R^1$ substituents;

wherein each m is independently an integer from 0 to 3;

each n is independently an integer from 0 to 3;

each p is independently an integer from 0 to 2;

each r is independently an integer from 0 to 3;

each s is independently an integer from 0 to 3; and each t is independently an integer from 0 to 3;

or a pharmaceutically acceptable salt thereof.

The present invention also relates to pharmaceutical compositions comprising the compounds of the present invention and a pharmaceutically acceptable carrier.

The present invention also relates to methods for making the pharmaceutical compositions of the present invention.

The present invention also relates to methods for eliciting an integrin receptor antagonizing effect in a mammal in need thereof by administering the compounds and pharmaceutical compositions of the present invention.

The present invention also relates to methods for inhibiting bone resorption, restenosis, atherosclerosis, inflammatory arthritis, diabetic retinopathy, macular degeneration, angiogenesis, wound healing, cancer, and metastatic tumor growth by administering the compounds and pharmaceutical compositions of the present invention.

The present invention also relates to methods for treating osteoporosis by administering the compounds and pharmaceutical compositions of the present invention.

DETAILED DESCRIPTION OF THE INVENTION

The present invention relates to compounds useful as integrin receptor antagonists. Representative compounds of the present invention are described by the following structural formula:

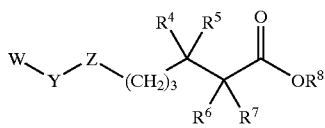

wherein any methylene (CH$_2$) carbon atom of the propylene [(CH$_2$)$_3$] chain in the formula can be independently substituted by one or two R$^3$ substituents;

W is selected from the group consisting of
- a 5- or 6-membered monocyclic aromatic or nonaromatic ring system having 1, 2, 3 or 4 heteroatoms selected from the group consisting of N, O, and S wherein the ring nitrogen atoms are unsubstituted or substituted with one R$^1$ substituent and the ring carbon atoms are unsubstituted or substituted with one or two R$^1$ substituents, and
- a 9- to 14-membered polycyclic ring system, wherein the polycyclic ring system has 1, 2, 3 or 4 heteroatoms selected from the group consisting of N, O, and S, and wherein the ring nitrogen atoms are unsubstituted or substituted with one R$^1$ substituent and the ring carbon atoms are unsubstituted or substituted with one or two R$^1$ substituents;

Y is selected from the group consisting of
—(CH$_2$)$_m$—,
—(CH$_2$)$_m$—O—(CH$_2$)$_n$—,
—(CH$_2$)$_m$—NR$^2$—(CH$_2$)$_n$—,
—(CH$_2$)$_m$—S—(CH$_2$)$_n$—,
—(CH$_2$)$_m$—SO—(CH$_2$)$_n$—,
—(CH$_2$)$_m$—SO$_2$—(CH$_2$)$_n$—,
—(CH$_2$)$_m$—O—(CH$_2$)$_n$—O—(CH$_2$)$_p$—,
—(CH$_2$)$_m$—O—(CH$_2$)$_n$—NR$^2$—(CH$_2$)$_p$—,
—(CH$_2$)$_m$—NR$^2$—(CH$_2$)$_n$—NR$^2$—(CH$_2$)$_p$—,
—(CH$_2$)$_m$—O—(CH$_2$)$_n$—S—(CH$_2$)$_p$—,
—(CH$_2$)$_m$—S—(CH$_2$)$_n$—S—(CH$_2$)$_p$—,
—(CH$_2$)$_m$—NR$^2$—(CH$_2$)$_n$—S—(CH$_2$)$_p$—,
—(CH$_2$)$_m$—NR$^2$—(CH$_2$)$_n$—O—(CH$_2$)$_p$—,
—(CH$_2$)$_m$—S—(CH$_2$)$_n$—O—(CH$_2$)$_p$—, and
—(CH$_2$)$_m$—S—(CH$_2$)$_n$—NR$^2$—(CH$_2$)$_p$—, wherein any methylene (CH$_2$) carbon atom in Y, other than in R$^2$, can be substituted by one or two R$^3$ substituents;

Z is a 5- or 6-membered heterocyclic ring system having 1 to 3 heteroatoms selected from the group consisting of N, O, and S, and wherein the ring system is either unsubstituted or substituted with one or more substituents independently selected from the group consisting of R$^9$, such that two R$^9$ substituents, when on the same carbon atom, are taken together with the carbon atom to which they are attached to form a C$_3$–C$_6$ cycloalkyl group;

R$^1$ is independently selected from the group consisting of
hydrogen, halogen, C$_{1-10}$ alkyl, C$_{3-8}$ cycloalkyl, C$_{3-8}$ cycloheteroalkyl, C$_{3-8}$ cycloalkyl C$_{1-6}$ alkyl, C$_{3-8}$ cycloheteroalkyl C$_{1-6}$ alkyl, aryl, aryl C$_{1-8}$ alkyl, amino, amino C$_{1-8}$ alkyl, C$_{1-3}$ acylamino, C$_{1-3}$ acylamino C$_{1-8}$ alkyl, (C$_{1-6}$ alkyl)$_p$amino, (C$_{1-6}$ alkyl)$_p$ amino C$_{1-8}$ alkyl, C$_{1-4}$ alkoxy, C$_{1-4}$ alkoxy C$_{1-6}$ alkyl, hydroxycarbonyl, hydroxycarbonyl C$_{1-6}$ alkyl, C$_{1-3}$ alkoxycarbonyl, C$_{1-3}$ alkoxycarbonyl C$_{1-6}$ alkyl, hydroxycarbonyl-C$_{1-6}$ alkyloxy, hydroxy, hydroxy C$_{1-6}$ alkyl, C$_{1-6}$ alkyloxy-C$_{1-6}$ alkyl, nitro, cyano, trifluoromethyl, trifluoromethoxy, trifluoroethoxy, C$_{1-8}$ alkyl-S(O)$_p$, (C$_{1-8}$ alkyl)$_p$ aminocarbonyl, C$_{1-8}$ alkyloxycarbonylamino, (C$_{1-8}$ alkyl)$_p$aminocarbonyloxy, (aryl C$_{1-8}$ alkyl)$_p$amino, (aryl)$_p$amino, aryl C$_{1-8}$-alkylsulfonylamino, and C$_{1-8}$ alkylsulfonylamino;

or two R$^1$ substituents, when on the same carbon atom, are taken together with the carbon atom to which they are attached to form a carbonyl group;

each R$^2$ is independently selected from the group consisting of
hydrogen,
aryl,
aminocarbonyl,
C$_{3-8}$ cycloalkyl,
amino C$_{1-6}$ alkyl,
(aryl)$_p$aminocarbonyl,
(aryl C$_{1-5}$ alkyl)$_p$aminocarbonyl,
hydroxycarbonyl C$_{1-6}$ alkyl,
C$_{1-8}$ alkyl,
aryl C$_{1-6}$ alkyl,
(C$_{1-6}$ alkyl)$_p$amino C$_{2-6}$ alkyl,
(aryl C$_{1-6}$ alkyl)$_p$amino C$_{2-6}$ alkyl,
C$_{1-8}$ alkylsulfonyl,
C$_{1-8}$ alkoxycarbonyl,
aryloxycarbonyl,
aryl C$_{1-8}$ alkoxycarbonyl,
C$_{1-8}$ alkylcarbonyl,
arylcarbonyl,
aryl C$_{1-6}$ alkylcarbonyl,
(C$_{1-8}$ alkyl)$_p$aminocarbonyl,
aminosulfonyl,
C$_{1-8}$ alkylaminosulfonyl,
(aryl)$_p$aminosulfonyl,
(aryl C$_{1-8}$ alkyl)$_p$aminosulfonyl,
arylsulfonyl,
aryl C$_{1-6}$ alkylsulfonyl,
C$_{1-6}$ alkylthiocarbonyl,
arylthiocarbonyl, and
aryl C$_{1-6}$ alkylthiocarbonyl, wherein any of the alkyl groups of R$^2$ are either unsubstituted or substituted with one to three R$^1$ substituents;

each R$^3$ is independently selected from the group consisting of
hydrogen,
aryl,
C$_{1-10}$ alkyl,
aryl-(CH$_2$)$_r$—O—(CH$_2$)$_s$—,
aryl(CH$_2$)$_r$S(O)(CH$_2$)$_s$—,
aryl-(CH$_2$)$_r$—C(O)—(CH$_2$)$_s$—,
aryl-(CH$_2$)$_r$—C(O)—N(R$^2$)—(CH$_2$)$_s$—,
aryl-(CH$_2$)$_r$—N(R$^2$)—C(O)—(CH$_2$)$_s$—,
aryl-(CH$_2$)$_r$—N(R$^2$)—(CH$_2$)$_s$—,
halogen,
hydroxyl,
oxo,
trifluoromethyl,
C$_{1-8}$ alkylcarbonylamino,
aryl C$_{1-5}$ alkoxy,
C$_{1-5}$ alkoxycarbonyl,
(C$_{1-8}$ alkyl)$_p$aminocarbonyl,
C$_{1-6}$ alkylcarbonyloxy,
C$_{3-8}$ cycloalkyl,
(C$_{1-6}$ alkyl)$_p$amino,
amino C$_{1-6}$ alkyl,
arylaminocarbonyl,
aryl C$_{1-5}$ alkylaminocarbonyl,
aminocarbonyl,
aminocarbonyl C$_{1-6}$ alkyl, hydroxycarbonyl,
hydroxycarbonyl $C_{1-6}$ alkyl,
$HC\equiv C-(CH_2)_t-$,
$C_{1-6}$ alkyl-$C\equiv C-(CH_2)_t-$,
$C_{3-7}$ cycloalkyl-$C\equiv C-(CH_2)_t-$,
aryl-$C\equiv C-(CH_2)_t-$,
$C_{1-6}$ alkylaryl-$C\equiv C-(CH_2)_t-$,
$CH_2=CH-(CH_2)_t-$,
$C_{1-6}$ alkyl-$CH=CH-(CH_2)_t-$,
$C_{3-7}$ cycloalkyl-$CH=CH-(CH_2)_t-$,
aryl-$CH=CH-(CH_2)_t-$,
$C_{1-6}$ alkylaryl-$CH=CH-(CH_2)_t-$,
$C_{1-6}$ alkyl-$SO_2-(CH_2)_t-$,
$C_{1-6}$ alkylaryl-$SO_2-(CH_2)_t-$,
$C_{1-6}$ alkoxy,
aryl $C_{1-6}$ alkoxy,
aryl $C_{1-6}$ alkyl,
$(C_{1-6}$ alkyl$)_p$amino $C_{1-6}$ alkyl,
(aryl$)_p$amino,
(aryl$)_p$amino $C_{1-6}$ alkyl,
(aryl $C_{1-6}$ alkyl$)_p$amino,
(aryl $C_{1-6}$ alkyl$)_p$amino $C_{1-6}$ alkyl,
arylcarbonyloxy,
aryl $C_{1-6}$ alkylcarbonyloxy,
$(C_{1-6}$ alkyl$)_p$aminocarbonyloxy,
$C_{1-8}$ alkylsulfonylamino,
arylsulfonylamino,
$C_{1-8}$ alkylsulfonylamino $C_{1-6}$ alkyl,
arylsulfonylamino $C_{1-6}$ alkyl,
aryl $C_{1-6}$ alkylsulfonylamino,
aryl $C_{1-6}$ alkylsulfonylamino $C_{1-6}$ alkyl,
$C_{1-8}$ alkoxycarbonylamino,
$C_{1-8}$ alkoxycarbonylamino $C_{1-8}$ alkyl,
aryloxycarbonylamino $C_{1-8}$ alkyl,
aryl $C_{1-8}$ alkoxycarbonylamino,
aryl $C_{1-8}$ alkoxycarbonylamino $C_{1-8}$ alkyl,
$C_{1-8}$ alkylcarbonylamino,
$C_{1-8}$ alkylcarbonylamino $C_{1-6}$ alkyl,
arylcarbonylamino $C_{1-6}$ alkyl,
aryl $C_{1-6}$ alkylcarbonylamino,
aryl $C_{1-6}$ alkylcarbonylamino $C_{1-6}$ alkyl,
aminocarbonylamino $C_{1-6}$ alkyl,
$(C_{1-8}$ alkyl$)_p$aminocarbonylamino,
$(C_{1-8}$ alkyl$)_p$aminocarbonylamino $C_{1-6}$ alkyl,
(aryl$)_p$aminocarbonylamino $C_{1-6}$ alkyl,
(aryl $C_{1-8}$ alkyl$)_p$aminocarbonylamino,
(aryl $C_{1-8}$ alkyl$)_p$aminocarbonylamino $C_{1-6}$ alkyl,
aminosulfonylamino $C_{1-6}$ alkyl,
$(C_{1-8}$ alkyl$)_p$aminosulfonylamino,
$(C_{1-8}$ alkyl$)_p$aminosulfonylamino $C_{1-6}$ alkyl,
(aryl$)_p$aminosulfonylamino $C_{1-6}$ alkyl,
(aryl $C_{1-8}$ alkyl$)_p$aminosulfonylamino,
(aryl $C_{1-8}$ alkyl$)_p$aminosulfonylamino $C_{1-6}$ alkyl,
$C_{1-6}$ alkylsulfonyl,
$C_{1-6}$ alkylsulfonyl $C_{1-6}$ alkyl,
arylsulfonyl $C_{1-6}$ alkyl,
aryl $C_{1-6}$ alkylsulfonyl,
aryl $C_{1-6}$ alkylsulfonyl $C_{1-6}$ alkyl,
$C_{1-6}$ alkylcarbonyl,
$C_{1-6}$ alkylcarbonyl $C_{1-6}$ alkyl,
arylcarbonyl $C_{1-6}$ alkyl,
aryl $C_{1-6}$ alkylcarbonyl,
aryl $C_{1-6}$ alkylcarbonyl $C_{1-6}$ alkyl,
$C_{1-6}$ alkylthiocarbonylamino,
$C_{1-6}$ alkylthiocarbonylamino $C_{1-6}$ alkyl,
arylthiocarbonylamino $C_{1-6}$ alkyl,
aryl $C_{1-6}$ alkylthiocarbonylamino,
aryl $C_{1-6}$ alkylthiocarbonylamino $C_{1-6}$ alkyl,
$(C_{1-8}$ alkyl$)_p$aminocarbonyl $C_{1-6}$ alkyl,
(aryl$)_p$aminocarbonyl $C_{1-6}$ alkyl,
(aryl $C_{1-8}$ alkyl$)_p$aminocarbonyl, and
(aryl $C_{1-8}$ alkyl$)_p$aminocarbonyl $C_{1-6}$ alkyl,
or two $R^3$ substituents, when on the same carbon atom are taken together with the carbon atom to which they are attached to form a carbonyl group or a cyclopropyl group,
wherein any of the alkyl groups of $R^3$ are either unsubstituted or substituted with one to three $R^1$ substituents, and provided that each $R^3$ is selected such that in the resultant compound the carbon atom or atoms to which $R^3$ is attached is itself attached to no more than one heteroatom;
$R^4$ and $R^5$ are each independently selected from the group consisting of
hydrogen,
$C_{1-10}$ alkyl,
aryl,
aryl-$(CH_2)_r-O-(CH_2)_s-$,
aryl-$(CH_2)_r-S(O)_p-(CH_2)_s-$,
aryl-$(CH_2)_r-C(O)-(CH_2)_s-$,
aryl-$(CH_2)_r-C(O)-N(R^2)-(CH_2)_s-$,
aryl-$(CH_2)_r-N(R^2)-C(O)-(CH_2)_s-$,
aryl-$(CH_2)_r-N(R^2)-(CH_2)_s-$,
halogen,
hydroxyl,
$C_{1-8}$ alkylcarbonylamino,
aryl $C_{1-5}$ alkoxy,
$C_{1-5}$ alkoxycarbonyl,
$(C_{1-8}$ alkyl$)_p$aminocarbonyl,
$C_{1-6}$ alkylcarbonyloxy,
$C_{3-8}$ cycloalkyl,
$(C_{1-6}$ alkyl$)_p$amino,
amino $C_{1-6}$ alkyl,
arylaminocarbonyl,
aryl $C_{1-5}$ alkylaminocarbonyl,
aminocarbonyl,
aminocarbonyl $C_{1-6}$ alkyl,
hydroxycarbonyl,
hydroxycarbonyl $C_{1-6}$ alkyl,
$HC\equiv C-(CH_2)_t-$,
$C_{1-6}$ alkyl-$C\equiv C-(CH_2)_t-$,
$C_{3-7}$ cycloalkyl-$C\equiv C-(CH_2)_t-$,
aryl-$C\equiv C-(CH_2)_t-$,
$C_{1-6}$ alkylaryl-$C\equiv C-(CH_2)_t-$,
$CH_2=CH-(CH_2)_t-$,
$C_{1-6}$ alkyl-$CH=CH-(CH_2)_t-$,
$C_{3-7}$ cycloalkyl-$CH=CH-(CH_2)_t-$,
aryl-$CH=CH-(CH_2)_t-$,
$C_{1-6}$ alkylaryl-$CH=CH-(CH_2)_t-$,
$C_{1-6}$ alkyl-$SO_2-(CH_2)_t-$,
$C_{1-6}$ alkylaryl-$SO_2-(CH_2)_t-$,
$C_{1-6}$ alkoxy,
aryl $C_{1-6}$ alkoxy,
aryl $C_{1-6}$ alkyl,
$(C_{1-6}$ alkyl$)_p$amino $C_{1-6}$ alkyl,
(aryl$)_p$amino,
(aryl$)_p$amino $C_{1-6}$ alkyl,
(aryl $C_{1-6}$ alkyl$)_p$amino,
(aryl $C_{1-6}$ alkyl$)_p$amino $C_{1-6}$ alkyl,
arylcarbonyloxy,
aryl $C_{1-6}$ alkylcarbonyloxy,
$(C_{1-6}$ alkyl$)_p$aminocarbonyloxy,
$C_{1-8}$ alkylsulfonylamino,
arylsulfonylamino, $C_{1-8}$ alkylsulfonylamino $C_{1-6}$ alkyl,
arylsulfonylamino $C_{1-6}$ alkyl,
aryl $C_{1-6}$ alkylsulfonylamino,
aryl $C_{1-6}$ alkylsulfonylamino $C_{1-6}$ alkyl,
$C_{1-8}$ alkoxycarbonylamino,
$C_{1-8}$ alkoxycarbonylamino $C_{1-8}$ alkyl,
aryloxycarbonylamino $C_{1-8}$ alkyl,
aryl $C_{1-8}$ alkoxycarbonylamino,
aryl $C_{1-8}$ alkoxycarbonylamino $C_{1-8}$ alkyl,
$C_{1-8}$ alkylcarbonylamino,
$C_{1-8}$ alkylcarbonylamino $C_{1-6}$ alkyl,
arylcarbonylamino $C_{1-6}$ alkyl,
aryl $C_{1-6}$ alkylcarbonylamino,
aryl $C_{1-6}$ alkylcarbonylamino $C_{1-6}$ alkyl,
aminocarbonylamino $C_{1-6}$ alkyl,
$(C_{1-8}$ alkyl$)_p$aminocarbonylamino,
$(C_{1-8}$ alkyl$)_p$aminocarbonylamino $C_{1-6}$ alkyl,
(aryl$)_p$aminocarbonylamino $C_{1-6}$ alkyl,
(aryl $C_{1-8}$ alkyl$)_p$aminocarbonylamino,
(aryl $C_{1-8}$ alkyl$)_p$aminocarbonylamino $C_{1-6}$ alkyl,
aminosulfonylamino $C_{1-6}$ alkyl,
$(C_{1-8}$ alkyl$)_p$aminosulfonylamino,
$(C_{1-8}$ alkyl$)_p$aminosulfonylamino $C_{1-6}$ alkyl,
(aryl$)_p$aminosulfonylamino $C_{1-6}$ alkyl,
(aryl $C_{1-8}$ alkyl$)_p$aminosulfonylamino,
(aryl $C_{1-8}$ alkyl$)_p$aminosulfonylamino $C_{1-6}$ alkyl,
$C_{1-6}$ alkylsulfonyl,
$C_{1-6}$ alkylsulfonyl $C_{1-6}$ alkyl,
arylsulfonyl $C_{1-6}$ alkyl,
aryl $C_{1-6}$ alkylsulfonyl,
aryl $C_{1-6}$ alkylsulfonyl $C_{1-6}$ alkyl,
$C_{1-6}$ alkylcarbonyl,
$C_{1-6}$ alkylcarbonyl $C_{1-6}$ alkyl,
arylcarbonyl $C_{1-6}$ alkyl,
aryl $C_{1-6}$ alkylcarbonyl,
aryl $C_{1-6}$ alkylcarbonyl $C_{1-6}$ alkyl,
$C_{1-6}$ alkylthiocarbonylamino,
$C_{1-6}$ alkylthiocarbonylamino $C_{1-6}$ alkyl,
arylthiocarbonylamino $C_{1-6}$ alkyl,
aryl $C_{1-6}$ alkylthiocarbonylamino,
aryl $C_{1-6}$ alkylthiocarbonylamino $C_{1-6}$ alkyl,
$(C_{1-8}$ alkyl$)_p$aminocarbonyl $C_{1-6}$ alkyl,
(aryl$)_p$aminocarbonyl $C_{1-6}$ alkyl,
(aryl $C_{1-8}$ alkyl$)_p$aminocarbonyl, and
(aryl $C_{1-8}$ alkyl$)_p$aminocarbonyl $C_{1-6}$ alkyl;

or $R^4$ and $R^5$ are taken together with the carbon atom to which they are attached to form a carbonyl group, wherein any of the alkyl groups of $R^4$ or $R^5$ are either unsubstituted or substituted with one to three $R^1$ substituents, and provided that each $R^4$ and $R^5$ are selected such that in the resultant compound the carbon atom to which $R^4$ and $R^5$ are attached is itself attached to no more than one heteroatom;

$R^6$ and $R^7$ are each independently selected from the group consisting of
hydrogen,
$C_{1-10}$ alkyl,
aryl,
aryl-$(CH_2)_r$—O—$(CH_2)_s$—,
aryl-$(CH_2)_r$S(O)$_p$—$(CH_2)_s$—,
aryl-$(CH_2)_r$—C(O)—$(CH_2)_s$—,
aryl-$(CH_2)_r$—C(O)—N($R^2$)—$(CH_2)_s$—,
aryl-$(CH_2)_r$—N($R^2$)—C(O)—$(CH_2)_s$—,
aryl-$(CH_2)_r$—N($R^2$)—$(CH_2)_s$—,
halogen,
hydroxyl, $C_{1-8}$ alkylcarbonylamino,
aryl $C_{1-5}$ alkoxy,
$C_{1-5}$ alkoxycarbonyl,
$(C_{1-8}$ alkyl$)_p$aminocarbonyl,
$C_{1-6}$ alkylcarbonyloxy,
$C_{3-8}$ cycloalkyl,
$(C_{1-6}$ alkyl$)_p$amino,
amino $C_{1-6}$ alkyl,
arylaminocarbonyl,
aryl $C_{1-5}$ alkylaminocarbonyl,
aminocarbonyl,
aminocarbonyl $C_{1-6}$ alkyl,
hydroxycarbonyl,
hydroxycarbonyl $C_{1-6}$ alkyl,
HC≡C—$(CH_2)_t$—,
$C_{1-6}$ alkyl-C≡C—$(CH_2)_t$—,
$C_{3-7}$ cycloalkyl-C≡C—$(CH_2)_t$—,
aryl-C≡C—$(CH_2)_t$—,
$C_{1-6}$ alkylaryl-C≡C—$(CH_2)_t$—,
$CH_2$=CH—$(CH_2)_t$—,
$C_{1-6}$ alkyl-CH=CH—$(CH_2)_t$—,
$C_{3-7}$ cycloalkyl-CH=CH—$(CH_2)_t$—,
aryl-CH=CH—$(CH_2)_t$—,
$C_{1-6}$ alkylaryl-CH=CH—$(CH_2)_t$—,
$C_{1-6}$ alkyl-$SO_2$—$(CH_2)_t$—,
$C_{1-6}$ alkylaryl-$SO_2$—$(CH_2)_t$—,
$C_{1-6}$ alkoxy,
aryl $C_{1-6}$ alkoxy,
aryl $C_{1-6}$ alkyl,
$(C_{1-6}$ alkyl$)_p$amino $C_{1-6}$ alkyl,
(aryl$)_p$amino,
(aryl$)_p$amino $C_{1-6}$ alkyl,
(aryl $C_{1-6}$ alkyl$)_p$amino,
(aryl $C_{1-6}$ alkyl$)_p$amino $C_{1-6}$ alkyl,
arylcarbonyloxy,
aryl $C_{1-6}$ alkylcarbonyloxy,
$(C_{1-6}$ alkyl$)_p$aminocarbonyloxy,
$C_{1-8}$ alkylsulfonylamino,
arylcarbonylamino,
arylsulfonylamino,
$C_{1-8}$ alkylsulfonylamino $C_{1-6}$ alkyl,
arylsulfonylamino $C_{1-6}$ alkyl,
aryl $C_{1-6}$ alkylsulfonylamino,
aryl $C_{1-6}$ alkylsulfonylamino $C_{1-6}$ alkyl,
$C_{1-8}$ alkoxycarbonylamino,
$C_{1-8}$ alkoxycarbonylamino $C_{1-8}$ alkyl,
aryloxycarbonylamino $C_{1-8}$ alkyl,
aryl $C_{1-8}$ alkoxycarbonylamino,
aryl $C_{1-8}$ alkoxycarbonylamino $C_{1-8}$ alkyl,
$C_{1-8}$ alkylcarbonylamino $C_{1-6}$ alkyl,
arylcarbonylamino $C_{1-6}$ alkyl,
aryl $C_{1-6}$ alkylcarbonylamino,
aryl $C_{1-6}$ alkylcarbonylamino $C_{1-6}$ alkyl,
aminocarbonylamino $C_{1-6}$ alkyl,
$(C_{1-8}$ alkyl$)_p$aminocarbonylamino,
$(C_{1-8}$ alkyl$)_p$aminocarbonylamino $C_{1-6}$ alkyl,
(aryl$)_p$aminocarbonylamino $C_{1-6}$ alkyl,
arylaminocarbonylamino,
(aryl $C_{1-8}$ alkyl$)_p$aminocarbonylamino,
(aryl $C_{1-8}$ alkyl$)_p$aminocarbonylamino $C_{1-6}$ alkyl,
aminosulfonylamino $C_{1-6}$ alkyl,
$(C_{1-8}$ alkyl$)_p$aminosulfonylamino,
$(C_{1-8}$ alkyl$)_p$aminosulfonylamino $C_{1-6}$ alkyl,
(aryl$)_p$aminosulfonylamino $C_{1-6}$ alkyl,
(aryl $C_{1-8}$ alkyl$)_p$aminosulfonylamino,
(aryl $C_{1-8}$ alkyl$)_p$aminosulfonylamino $C_{1-6}$ alkyl,
$C_{1-6}$ alkylsulfonyl, $C_{1-6}$ alkylsulfonyl $C_{1-6}$ alkyl,
arylsulfonyl $C_{1-6}$ alkyl,
aryl $C_{1-6}$ alkylsulfonyl,
aryl $C_{1-6}$ alkylsulfonyl $C_{1-6}$ alkyl,
$C_{1-6}$ alkylcarbonyl,
$C_{1-6}$ alkylcarbonyl $C_{1-6}$ alkyl,
arylcarbonyl $C_{1-6}$ alkyl,
aryl $C_{1-6}$ alkylcarbonyl,
aryl $C_{1-6}$ alkylcarbonyl $C_{1-6}$ alkyl,
$C_{1-6}$ alkylthiocarbonylamino,
$C_{1-6}$ alkylthiocarbonylamino $C_{1-6}$ alkyl,
arylthiocarbonylamino $C_{1-6}$ alkyl,
aryl $C_{1-6}$ alkylthiocarbonylamino,
aryl $C_{1-6}$ alkylthiocarbonylamino $C_{1-6}$ alkyl,
$(C_{1-8}$ alkyl$)_p$aminocarbonyl $C_{1-6}$ alkyl,
(aryl$)_p$aminocarbonyl $C_{1-6}$ alkyl,
(aryl $C_{1-8}$ alkyl$)_p$aminocarbonyl,
(aryl $C_{1-8}$ alkyl$)_p$aminocarbonyl $C_{1-6}$ alkyl, and
$C_{7-20}$ polycyclyl $C_{0-8}$ alkylsulfonylamino;
wherein any of the alkyl groups of $R^6$ and $R^7$ are either unsubstituted or substituted with one to three $R^1$ substituents, and provided that each $R^6$ and $R^7$ are selected such that in the resultant compound the carbon atom to which $R^6$ and $R^7$ are attached is itself attached to no more than one heteroatom;
$R^8$ is selected from the group consisting of
hydrogen,
$C_{1-8}$ alkyl,
aryl,
aryl $C_{1-8}$ alkyl,
$C_{1-8}$ alkylcarbonyloxy $C_{1-4}$ alkyl,
aryl $C_{1-8}$ alkylcarbonyloxy $C_{1-4}$ alkyl,
$C_{1-8}$ alkylaminocarbonylmethylene, and
$C_{1-8}$ dialkylaminocarbonylmethylene;
each $R^9$ is independently selected from the group consisting of
hydrogen,
$C_{1-8}$ alkyl,
aryl,
halogen,
hydroxyl,
oxo,
aminocarbonyl,
amino $C_{1-6}$ alkyl,
(aryl$)_p$aminocarbonyl,
hydroxycarbonyl,
(aryl $C_{1-5}$ alkyl$)_p$aminocarbonyl,
hydroxycarbonyl $C_{1-6}$ alkyl,
aryl $C_{1-6}$ alkyl,
$(C_{1-6}$ alkyl$)_p$amino $C_{1-6}$ alkyl,
(aryl $C_{1-6}$ alkyl$)_p$amino $C_{2-6}$ alkyl,
$C_{1-8}$ alkylsulfonyl,
$C_{1-8}$ alkoxycarbonyl,
aryloxycarbonyl,
aryl $C_{1-8}$ alkoxycarbonyl,
$C_{1-8}$ alkylcarbonyl,
arylcarbonyl,
aryl $C_{1-6}$ alkylcarbonyl,
$(C_{1-8}$ alkyl$)_p$aminocarbonyl,
aminosulfonyl,
$C_{1-8}$ alkylaminosulfonyl,
(aryl$)_p$aminosulfonyl,
(aryl $C_{1-8}$ alkyl$)_p$aminosulfonyl,
$C_{1-6}$ alkylsulfonyl,
arylsulfonyl,
aryl $C_{1-6}$ alkylsulfonyl,
aryl $C_{1-6}$ alkylcarbonyl,
$C_{1-6}$ alkylthiocarbonyl,
arylthiocarbonyl,
aryl $C_{1-6}$ alkylthiocarbonyl,
aryl-$(CH_2)_r$—O—$(CH_2)_s$—,
aryl-$(CH_2)_r$—S(O)$_p$—$(CH_2)_s$—,
aryl-$(CH_2)_r$—C(O)—$(CH_2)_s$—,
aryl-$(CH_2)_r$—C(O)—N($R^2$)—$(CH_2)_s$—,
aryl-$(CH_2)_r$—N($R^2$)—C(O)—$(CH_2)_s$—,
aryl-$(CH_2)_r$—N($R^2$)—$(CH_2)_s$—,
HC≡C—$(CH_2)_t$—,
$C_{1-6}$ alkyl-C≡C—$(CH_2)_t$—,
$C_{3-7}$ cycloalkyl-C≡C—$(CH_2)_t$—,
aryl-C≡C—$(CH_2)_t$—,
$C_{1-6}$ alkylaryl-C≡C—$(CH_2)_t$—,
$CH_2$=CH—$(CH_2)_t$—,
$C_{1-6}$ alkyl-CH=CH—$(CH_2)_t$—,
$C_{3-7}$ cycloalkyl-CH=CH—$(CH_2)_t$—,
aryl-CH=CH—$(CH_2)_t$—,
$C_{1-6}$ alkylaryl-CH=CH—$(CH_2)_t$—,
$C_{1-6}$ alkyl-SO$_2$—$(CH_2)_t$—,
$C_{1-6}$ alkylaryl-SO$_2$—$(CH_2)_t$—,
$C_{7-20}$ polycyclyl $C_{0-8}$ alkylsulfonylamino $C_{0-6}$ alkyl,
$C_{7-20}$ polycyclyl $C_{0-8}$ alkylcarbonylamino $C_{0-6}$ alkyl,
$C_{7-20}$ polycyclyl $C_{0-8}$ alkylaminosulfonylamino $C_{0-6}$ alkyl,
$C_{7-20}$ polycyclyl $C_{0-8}$ alkylaminocarbonylamino $C_{0-6}$ alkyl,
$C_{7-20}$ polycyclyl $C_{0-8}$ alkyloxycarbonylamino $C_{0-6}$ alkyl,
$C_{1-8}$ alkylcarbonylamino,
aryl $C_{1-5}$ alkoxy,
$C_{1-5}$ alkoxycarbonyl,
$(C_{1-8}$ alkyl$)_p$aminocarbonyl,
$C_{1-6}$ alkylcarbonyloxy,
$(C_{1-6}$ alkyl$)_p$amino,
aminocarbonyl $C_{1-6}$ alkyl,
$C_{1-6}$ alkoxy,
aryl $C_{1-6}$ alkoxy,
(aryl$)_p$amino,
(aryl$)_p$amino $C_{1-6}$ alkyl,
(aryl $C_{1-6}$ alkyl$)_p$amino,
(aryl $C_{1-6}$ alkyl$)_p$amino $C_{1-6}$ alkyl,
arylcarbonyloxy,
aryl $C_{1-6}$ alkylcarbonyloxy,
$(C_{1-6}$ alkyl$)_p$aminocarbonyloxy,
$C_{1-8}$ alkylsulfonylamino,
arylsulfonylamino,
$C_{1-8}$ alkylsulfonylamino $C_{1-6}$ alkyl,
arylsulfonylamino $C_{1-6}$ alkyl,
aryl $C_{1-6}$ alkylsulfonylamino,
aryl $C_{1-6}$ alkylsulfonylamino $C_{1-6}$ alkyl,
$C_{1-8}$ alkoxycarbonylamino,
$C_{1-8}$ alkoxycarbonylamino $C_{1-8}$ alkyl,
aryloxycarbonylamino $C_{1-8}$ alkyl,
aryl $C_{1-8}$ alkoxycarbonylamino,
aryl $C_{1-8}$ alkoxycarbonylamino $C_{1-8}$ alkyl,
$C_{1-8}$ alkylcarbonylamino,
$C_{1-8}$ alkylcarbonylamino $C_{1-6}$ alkyl,
arylcarbonylamino $C_{1-6}$ alkyl,
aryl $C_{1-6}$ alkylcarbonylamino,
aryl $C_{1-6}$ alkylcarbonylamino $C_{1-6}$ alkyl,
aminocarbonylamino $C_{1-6}$ alkyl,
$(C_{1-8}$ alkyl$)_p$aminocarbonylamino,
$(C_{1-8}$ alkyl$)_p$aminocarbonylamino $C_{1-6}$ alkyl,
(aryl$)_p$aminocarbonylamino $C_{1-6}$ alkyl,
(aryl $C_{1-8}$ alkyl$)_p$aminocarbonylamino,
(aryl $C_{1-8}$ alkyl$)_p$aminocarbonylamino $C_{1-6}$ alkyl, aminosulfonylamino $C_{1-6}$ alkyl,
$(C_{1-8}$ alkyl$)_p$aminosulfonylamino,
$(C_{1-8}$ alkyl$)_p$aminosulfonylamino $C_{1-6}$ alkyl,
(aryl$)_p$aminosulfonylamino $C_{1-6}$ alkyl,
(aryl $C_{1-8}$ alkyl$)_p$aminosulfonylamino,
(aryl $C_{1-8}$ alkyl$)_p$aminosulfonylamino $C_{1-6}$ alkyl,
$C_{1-6}$ alkylsulfonyl,
$C_{1-6}$ alkylsulfonyl $C_{1-6}$ alkyl,
arylsulfonyl $C_{1-6}$ alkyl,
aryl $C_{1-6}$ alkylsulfonyl,
aryl $C_{1-6}$ alkylsulfonyl $C_{1-6}$ alkyl,
$C_{1-6}$ alkylcarbonyl,
$C_{1-6}$ alkylcarbonyl $C_{1-6}$ alkyl,
arylcarbonyl $C_{1-6}$ alkyl,
aryl $C_{1-6}$ alkylcarbonyl,
aryl $C_{1-6}$ alkylcarbonyl $C_{1-6}$ alkyl,
$C_{1-6}$ alkylthiocarbonylamino,
$C_{1-6}$ alkylthiocarbonylamino $C_{1-6}$ alkyl,
arylthiocarbonylamino $C_{1-6}$ alkyl,
aryl $C_{1-6}$ alkylthiocarbonylamino,
aryl $C_{1-6}$ alkylthiocarbonylamino $C_{1-6}$ alkyl,
$(C_{1-8}$ alkyl$)_p$aminocarbonyl $C_{1-6}$ alkyl,
(aryl$)_p$aminocarbonyl $C_{1-6}$ alkyl,
(aryl $C_{1-8}$ alkyl$)_p$aminocarbonyl, and
(aryl $C_{1-8}$ alkyl$)_p$aminocarbonyl $C_{1-6}$ alkyl;
and wherein any of the alkyl groups of $R^9$ are either unsubstituted or substituted with one to three $R^1$ substituents;
wherein each m is independently an integer from 0 to 3;
each n is independently an integer from 0 to 3;
each p is independently an integer from 0 to 2;
each r is independently an integer from 0 to 3;
each s is independently an integer from 0 to 3; and
each t is independently an integer from 0 to 3;
or a pharmaceutically acceptable salt thereof.

In one embodiment of the present invention, W is a 6-membered monocyclic aromatic or nonaromatic ring system having 1 or 2 nitrogen atoms wherein each non-aromatic ring nitrogen atom is optionally substituted with one $R^1$ substituent and each carbon atom is optionally substituted with one or two $R^1$ substituents, or a 9- to 14-membered polycyclic ring system, wherein the polycyclic ring system has 1, 2, 3, or 4 heteroatoms selected from the group consisting of N, O, and S wherein the ring nitrogen atoms are unsubstituted or substituted with one $R^1$ substituent and the ring carbon atoms are unsubstituted or substituted with one or two $R^1$ substituents.

In a class of this embodiment of the present invention, W is

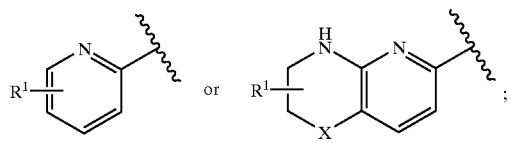

wherein X is $(CH_2)_{0-2}$, O, or S;

In a subclass of this class of the present invention, W is

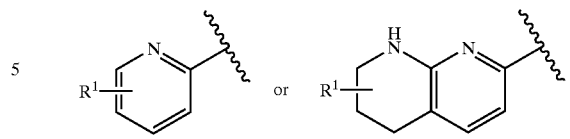

In a further subclass of this class of the present invention, W is

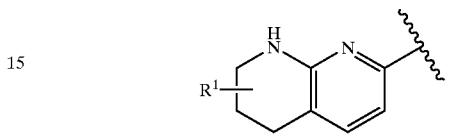

In one embodiment of the present invention, Y is selected from the group consisting of —$(CH_2)_m$—,
—$(CH_2)_m$—O—$(CH_2)_n$—,
—$(CH_2)_m$—$NR^2$—$(CH_2)_n$—,
—$(CH_2)_m$—S—$(CH_2)_n$—,
—$(CH_2)_m$—SO—$(CH_2)_n$—,
—$(CH_2)_m$—$SO_2$—$(CH_2)_n$—,
—$(CH_2)_m$—O—$(CH_2)_n$—O—$(CH_2)_p$—,
—$(CH_2)_m$—O—$(CH_2)_n$—$NR^2$—$(CH_2)_p$—,
—$(CH_2)_m$—$NR^2$—$(CH_2)_n$—$NR^2$—$(CH_2)_p$—, and
—$(CH_2)_m$—$NR^2$—$(CH_2)_n$—O—$(CH_2)_p$—, wherein any carbon atom in Y, other than in $R^2$, can be substituted by one or two $R^3$ substituents.

In a class of this embodiment of the present invention, Y is selected from the group consisting of $(CH_2)_m$, $(CH_2)_m$—O—$(CH_2)_n$, and $(CH_2)_m$—$NR^2$—$(CH_2)_n$, wherein any methylene $(CH_2)$ carbon atom in Y, other than in $R^2$, can be substituted by one or two $R^3$ substituents.

In one embodiment of the present invention, Z is selected from the group consisting of

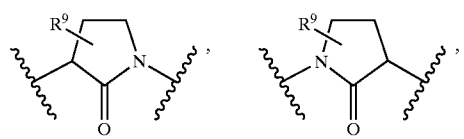

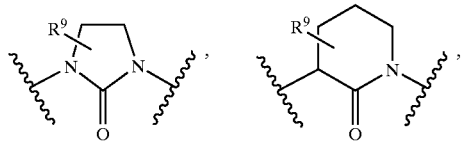

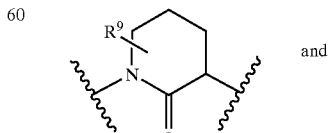 and

In a class of this embodiment of the present invention, Z is selected from the group consisting of

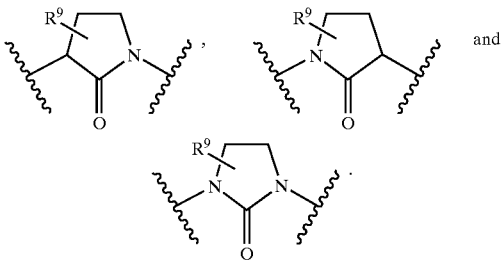

In a subclass of this class of the present invention, Z represents

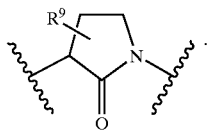

In one embodiment of the present invention, $R^1$ is selected from the group consisting of hydrogen, halogen, $C_{1-10}$ alkyl, $C_{3-8}$ cycloalkyl, $C_{3-8}$ cycloheteroalkyl, hydroxy, nitro, cyano, trifluoromethyl, and trifluoromethoxy.

In a class of this embodiment of the present invention, $R^1$ is selected from the group consisting of hydrogen, halogen, $C_{1-10}$ alkyl, $C_{3-8}$ cycloalkyl, trifluoromethyl, and trifluoromethoxy.

In one embodiment of the present invention, $R^2$ is selected from the group consisting of
hydrogen,
aryl,
$C_{3-8}$ cycloalkyl,
$C_{1-8}$ alkyl,
$C_{1-8}$ alkylcarbonyl,
arylcarbonyl,
$C_{1-6}$ alkylsulfonyl,
arylsulfonyl,
aryl$C_{1-6}$ alkylsulfonyl,
aryl$C_{1-6}$ alkylcarbonyl,
$C_{1-8}$ alkylaminocarbonyl,
aryl$C_{1-5}$ alkylaminocarbonyl,
aryl$C_{1-8}$ alkoxycarbonyl, and
$C_{1-8}$alkoxycarbonyl.

In a class of this embodiment of the present invention, $R^2$ is selected from the group consisting of
hydrogen,
$C_{1-8}$ alkyl,
$C_{1-8}$ alkylcarbonyl,
arylcarbonyl,
aryl$C_{1-6}$ alkylcarbonyl,
$C_{1-6}$ alkylsulfonyl,
arylsulfonyl, and
aryl$C_{1-6}$ alkylsulfonyl.

In one embodiment of the present invention, $R^3$ is selected from the group consisting of
hydrogen,
fluoro,
trifluoromethyl,
aryl,
$C_{1-8}$ alkyl,
aryl $C_{1-6}$ alkyl,
hydroxyl,
oxo,
arylaminocarbonyl,
aryl $C_{1-5}$ alkylaminocarbonyl,
aminocarbonyl, and
aminocarbonyl $C_{1-6}$ alkyl.

In a class of this embodiment of the present invention, $R^3$ is selected from the group consisting of
fluoro,
aryl,
$C_{1-8}$ alkyl,
aryl $C_{1-6}$ alkyl,
hydroxyl,
oxo, and
arylaminocarbonyl.

In one embodiment of the present invention, $R^4$ and $R^5$ are each independently selected from the group consisting of
hydrogen,
aryl,
$C_{1-8}$ alkyl,
aryl-C≡C—$(CH_2)_t$—,
aryl $C_{1-6}$ alkyl,
$CH_2$=CH—$(CH_2)_t$—, and
HC≡C—$(CH_2)_t$—.

In a class of this embodiment of the present invention, $R^5$ is hydrogen and $R^4$ is selected from the group consisting of
hydrogen,
aryl,
$C_{1-8}$ alkyl,
aryl-C≡C—$(CH_2)_t$—,
aryl $C_{1-6}$ alkyl,
$CH_2$=CH—$(CH_2)_t$—, and
HC≡C—$(CH_2)_t$—.

In a subclass of this class of the present invention, $R^5$, $R^6$, and $R^7$ are each hydrogen and $R^4$ is selected from the group consisting of
hydrogen,
aryl,
$C_{1-8}$ alkyl,
aryl-C≡C—$(CH_2)_t$—,
aryl $C_{1-6}$ alkyl,
$CH_2$=CH—$(CH_2)_t$—, and
HC≡C—$(CH_2)_t$—.

In another embodiment of the present invention, $R^6$ and $R^7$ are each independently selected from the group consisting of
hydrogen,
aryl,
$C_{1-8}$ alkylcarbonylamino,
arylcarbonylamino,
$C_{1-8}$ alkylsulfonylamino,
arylsulfonylamino,
$C_{1-8}$ alkylsulfonylamino $C_{1-6}$ alkyl,
arylsulfonylamino $C_{1-6}$ alkyl,
aryl $C_{1-6}$ alkylsulfonylamino, aryl $C_{1-6}$ alkylsulfonylamino $C_{1-6}$ alkyl,
$C_{1-8}$ alkoxycarbonylamino,
$C_{1-8}$ alkoxycarbonylamino $C_{1-8}$ alkyl,
aryloxycarbonylamino $C_{1-8}$ alkyl,
aryl $C_{1-8}$ alkoxycarbonylamino,
aryl $C_{1-8}$ alkoxycarbonylamino $C_{1-8}$ alkyl,
$C_{1-8}$ alkylcarbonylamino $C_{1-6}$ alkyl,
arylcarbonylamino $C_{1-6}$ alkyl,
aryl $C_{1-6}$ alkylcarbonylamino,
aryl $C_{1-6}$ alkylcarbonylamino $C_{1-6}$ alkyl,
aminocarbonylamino $C_{1-6}$ alkyl,
$(C_{1-8}$ alkyl$)_p$aminocarbonylamino,
$(C_{1-8}$ alkyl$)_p$aminocarbonylamino $C_{1-6}$ alkyl,
(aryl$)_p$aminocarbonylamino $C_{1-6}$ alkyl,
(aryl $C_{1-8}$ alkyl$)_p$aminocarbonylamino,
(aryl $C_{1-8}$ alkyl$)_p$aminocarbonylamino $C_{1-6}$ alkyl,
aminosulfonylamino $C_{1-6}$ alkyl,
$(C_{1-8}$ alkyl$)_p$aminosulfonylamino,
$(C_{1-8}$ alkyl$)_p$aminosulfonylamino $C_{1-6}$ alkyl,
(aryl$)_p$aminosulfonylamino $C_{1-6}$ alkyl,
(aryl $C_{1-8}$ alkyl$)_p$aminosulfonylamino,
(aryl $C_{1-8}$ alkyl$)_p$aminosulfonylamino $C_{1-6}$ alkyl,
$C_{1-6}$ alkylthiocarbonylamino,
$C_{1-6}$ alkylthiocarbonylamino $C_{1-6}$ alkyl,
arylthiocarbonylamino $C_{1-6}$ alkyl,
aryl $C_{1-6}$ alkylthiocarbonylamino, and
aryl $C_{1-6}$ alkylthiocarbonylamino $C_{1-6}$ alkyl.

In a class of this embodiment of the present invention, $R^7$ is hydrogen and $R^6$ is selected from the group consisting of consisting of
hydrogen,
aryl,
$C_{1-8}$ alkylcarbonylamino,
aryl $C_{1-6}$ alkylcarbonylamino,
arylcarbonylamino,
$C_{1-8}$ alkylsulfonylamino,
aryl $C_{1-6}$ alkylsulfonylamino,
arylsulfonylamino,
$C_{1-8}$ alkoxycarbonylamino,
aryl $C_{1-8}$ alkoxycarbonylamino,
arylaminocarbonylamino,
$(C_{1-8}$ alkyl$)_p$aminocarbonylamino,
(aryl $C_{1-8}$ alkyl$)_p$aminocarbonylamino,
$(C_{1-8}$ alkyl$)_p$aminosulfonyl amino, and
(aryl $C_{1-8}$ alkyl$)_p$aminosulfonylamino.

In a subclass of this class of the present invention, $R^4$, $R^5$, and $R^7$ are each hydrogen and $R^6$ is selected from the group consisting of
hydrogen,
aryl,
$C_{1-8}$ alkylcarbonylamino,
aryl $C_{1-6}$ alkylcarbonylamino,
arylcarbonylamino,
$C_{1-8}$ alkylsulfonylamino,
aryl $C_{1-6}$ alkylsulfonylamino,
arylsulfonylamino,
$C_{1-8}$ alkoxycarbonylamino,
aryl $C_{1-8}$ alkoxycarbonylamino,
arylaminocarbonylamino,
$(C_{1-8}$ alkyl$)_p$aminocarbonylamino,
(aryl $C_{1-8}$ alkyl$)_p$aminocarbonylamino,
$(C_{1-8}$ alkyl$)_p$aminosulfonylamino, and
(aryl $C_{1-8}$ alkyl$)_p$aminosulfonylamino, In one embodiment of the present invention, $R^8$ is selected from the group consisting of hydrogen, methyl, and ethyl.

In a class of this embodiment of the present invention, $R^8$ is hydrogen.

In one embodiment of the present invention, $R^9$ is independently selected from the group consisting of hydrogen and $C_{1-8}$ alkyl.

In a class of this embodiment of the present invention $R^9$ is hydrogen.

In one embodiment of the present invention, m is an integer from 0 to 2.

In one embodiment of the present invention, n is an integer from 0 to 1.

In one embodiment of the present invention, r is an integer from 1 to 2.

In one embodiment of the present invention, s is an integer from 0 to 2.

In one embodiment of the present invention, t is an integer from 0 to 2.

In a class of this embodiment of the present invention, t is an integer from 0 to 1.

In certain embodiments of the present invention the compounds have stereochemistry as designated in the following structural formula:

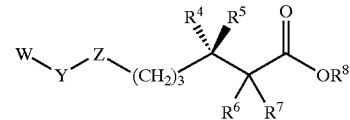

wherein the substituents W, Y, Z, $R^1$, $R^2$, $R^3$, $R^4$, $R^5$, $R^6$, $R^7$, $R^8$, and $R^9$, and the subscripts m, n, p, r, s, and t are as described above.

In certain embodiments of the present invention the compounds have stereochemistry as designated in the following structural formula:

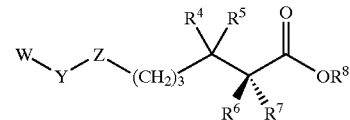

wherein the substituents W, Y, Z, $R^1$, $R^2$, $R^3$, $R^4$, $R^5$, $R^6$, $R^7$, $R^8$, and $R^9$, and the subscripts m, n, p, r, s, and t are as described above.

Illustrative but nonlimiting examples of compounds of the present invention that are useful as integrin receptor antagonists are the following:

3(R or S)-(6-Methoxy-pyridin-3-yl)-6-{2-oxo-3(R)-[2-(5,6,7,8-tetrahydro-[1,8]naphthyridin-2-yl)-ethyl]-pyrrolidin-1-yl }hexanoic acid;

3(S or R)-(6-Methoxy-pyridin-3-yl)-6-{2-oxo-3(R)-[2-(5,6,7,8-tetrahydro-[1,8]naphthyridin-2-yl)-ethyl]-pyrrolidin-1-yl}hexanoic acid;

3(R or S)-(6-Methoxy-pyridin-3-yl)-6-{2-oxo-3(S)-[2-(5,6,7,8-tetrahydro-[1,8]naphthyridin-2-yl)-ethyl]-pyrrolidin-1-yl }hexanoic acid;

3(S or R)-(6-Methoxy-pyridin-3-yl)-6-{2-oxo-3(S)-[2-(5,6,7,8-tetrahydro-[1,8]naphthyridin-2-yl)-ethyl]-pyrrolidin-1-yl}hexanoic acid;

3(S or R)-(6-Methoxy-pyridin-3-yl)-6-{5(S or R)-methyl-2-oxo-3(S)-[(5,6,7,8-tetrahydro-[1,8]naphthyridin-2-yl)-ethyl]-pyrrolidin-1-yl}hexanoic acid;

3(S or R)-(6-Methoxy-pyridin-3-yl)-6-{5(R or S)-methyl-2-oxo-3(S)-[(5,6,7,8-tetrahydro-[1,8]naphthyridin-2-yl)-ethyl]-pyrrolidin-1-yl }hexanoic acid;

3(S)-(6-Methoxy-pyridin-3-yl)-6-{5(R)-methyl-2-oxo-3(S)-[(5,6,7,8-tetrahydro-[1,8]naphthyridin-2-ylmethyl)-amino]-pyrrolidin-1-yl}-hexanoic acid;

3(S)-(2-Methyl-pyrimidin-5-yl)-$^6$-{5(R)-methyl-2-oxo-3(S)-[(5,6,7,8-tetrahydro-[1,8]naphthyridin-2-ylmethyl)-amino]-pyrrolidin-1-yl }-hexanoic acid;

3(R or S)-(2-Methoxy-pyrimidin-5-yl)-$^6$-{2-oxo-3(S)-[2-(5,6,7,8-tetrahydro-[1,8]naphthyridin-2-yl)-ethyl]-pyrrolidin-1-yl }hexanoic acid;

3(S or R)-(2-Methoxy-pyrimidin-5-yl)-6-{5(S or R)-methyl-2-oxo-3(S)-[(5,6,7,8-tetrahydro-[1,8]naphthyridin-2-yl)-ethyl]-pyrrolidin-1-yl }hexanoic acid; and 3(S or R)-(2-Methoxy-pyrimidin-5-yl)-6-{5(R or S)-methyl-2-oxo-3(S)-[(5,6,7,8-tetrahydro-[1,8]naphthyridin-2-yl)-ethyl]-pyrrolidin-1-yl }hexanoic acid;

or a pharmaceutically acceptable salt thereof.

For use in medicine, the salts of the compounds of this invention refer to non-toxic "pharmaceutically acceptable salts." Other salts may, however, be useful in the preparation of the compounds according to the invention or of their pharmaceutically acceptable salts. Salts of basic compounds encompassed within the term "pharmaceutically acceptable salts" refer to non-toxic salts of the compounds of this invention which are generally prepared by reacting the free base with a suitable organic or inorganic acid. Representative salts of basic compounds of the present invention include, but are not limited to, the following: acetate, benzenesulfonate, benzoate, bicarbonate, bisulfate, bitartrate, borate, bromide, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucaine ammonium salt, oleate, oxalate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

The compounds of the present invention can have chiral centers and occur as racemates, racemic mixtures, diastereomeric mixtures, and as individual diastereomers, or enantiomers with all isomeric forms being included in the present invention. Therefore, where a compound is chiral, the separate enantiomers or diastereomers, substantially free of the other, are included within the scope of the invention; further included are all mixtures of the two enantiomers. Also included within the scope of the invention are crystalline polymorphs and hydrates of the compounds of the instant invention.

The present invention includes within its scope prodrugs of the compounds of this invention. In general, such prodrugs will be functional derivatives of the compounds of this invention which are readily convertible in vivo into the required compound. Thus, in the methods of treatment of the present invention, the term "administering" shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs," ed. H. Bundgaard, Elsevier, 1985, which is incorporated by reference herein in its entirety. Metabolites of these compounds include active species produced upon introduction of compounds of this invention into the biological milieu.

The term "therapeutically effective amount" shall mean that amount of a drug or pharmaceutical agent that will elicit the biological or medical response of a tissue, system, animal or human that is being sought by a researcher or clinician.

The term "integrin receptor antagonist," as used herein, refers to a compound which binds to and antagonizes either the $\alpha v\beta 3$ receptor or the $\alpha v\beta 5$ receptor, or a compound which binds to and antagonizes a combination of these receptors (for example, a dual $\alpha v\beta 3/\alpha v\beta 5$ receptor antagonist).

The term "bone resorption," as used herein, refers to the process by which osteoclasts degrade bone.

The term "alkyl" shall mean straight or branched chain alkanes of one to ten total carbon atoms, or any number within this range (i.e., methyl, ethyl, 1-propyl, 2-propyl, n-butyl, s-butyl, t-butyl, etc.).

The term "alkenyl" shall mean straight or branched chain alkenes of two to ten total carbon atoms, or any number within this range.

The term "alkynyl" shall mean straight or branched chain alkynes of two to ten total carbon atoms, or any number within this range.

The term "cycloalkyl" shall mean cyclic rings of alkanes of three to eight total carbon atoms, or any number within this range (i.e., cyclopropyl, cyclobutyl, cyclopentyl, cyclohexyl, cycloheptyl or cyclooctyl).

The term "cycloheteroalkyl," as used herein, shall mean a 3- to 8-membered fully saturated heterocyclic ring containing one or two heteroatoms chosen from N, O or S. Examples of cycloheteroalkyl groups include, but are not limited to piperidinyl, pyrrolidinyl, azetidinyl, morpholinyl, piperazinyl.

The term "alkoxy," as used herein, refers to straight or branched chain alkoxides of the number of carbon atoms specified (e.g., $C_{1-5}$ alkoxy), or any number within this range (i.e., methoxy, ethoxy, etc.).

The term "aryl," as used herein, refers to a monocyclic or polycyclic system comprising at least one aromatic ring, wherein the monocylic or polycyclic system contains 0, 1, 2, 3, or 4 heteroatoms chosen from N, O, or S, and wherein the monocylic or polycylic system is either unsubstituted or substituted with one or more groups independently selected from hydrogen, halogen, $C_{1-10}$ alkyl, $C_{3-8}$ cycloalkyl, aryl, aryl $C_{1-8}$ alkyl, amino, amino $C_{1-8}$ alkyl, $C_{1-3}$ acylamino, $C_{1-3}$ acylamino $C_{1-8}$ alkyl, $C_{1-6}$ alkylamino, $C_{1-6}$ alkylamino $C_{1-8}$ alkyl, $C_{1-6}$ dialkylamino, $C_{1-6}$ dialkylamino-$C_{1-8}$ alkyl, $C_{1-4}$ alkoxy, $C_{1-4}$ alkoxy $C_{1-6}$ alkyl, hydroxycarbonyl, hydroxycarbonyl $C_{1-6}$ alkyl, $C_{1-5}$ alkoxycarbonyl, $C_{1-3}$ alkoxycarbonyl $C_{1-6}$ alkyl, hydroxycarbonyl $C_{1-6}$ alkyloxy, hydroxy, hydroxy $C_{1-6}$ alkyl, cyano, trifluoromethyl, oxo or $C_{1-5}$ alkylcarbonyloxy. Examples of aryl include, but are not limited to, phenyl, naphthyl, pyridyl, pyrryl, pyrazolyl, pyrazinyl, pyrimidinyl, imidazolyl, benzimidazolyl, benzthiazolyl, benzoxazolyl, indolyl, thienyl, furyl, dihydrobenzofuryl, benzo(1,3)dioxolane, oxazolyl, isoxazolyl and thiazolyl, which are either unsubstituted or substituted with one or more groups independently selected from hydrogen, halogen, $C_{1-10}$ alkyl, $C_{3-8}$ cycloalkyl, aryl, aryl $C_{1-8}$ alkyl, amino, amino $C_{1-8}$ alkyl, $C_{1-3}$ acylamino, $C_{1-3}$ acylamino $C_{1-8}$ alkyl, $C_{1-6}$ alkylamino, $C_{1-6}$ alkylamino-$C_{1-8}$ alkyl, $C_{1-6}$ dialkylamino, $C_{1-6}$ dialkylamino $C_{1-8}$ alkyl, $C_{1-4}$ alkoxy, $C_{1-4}$ alkoxy $C_{1-6}$ alkyl, hydroxycarbonyl, hydroxycarbonyl $C_{1-6}$ alkyl, $C_{1-5}$ alkoxycarbonyl, $C_{1-3}$ alkoxycarbonyl $C_{1-6}$ alkyl, hydroxycarbonyl $C_{1-6}$ alkyloxy, hydroxy, hydroxy $C_{1-6}$ alkyl, cyano, trifluoromethyl, oxo or $C_{1-5}$ alkylcarbonyloxy. Preferably, the aryl group is unsubstituted, mono-, di-, tri- or tetra-substituted with one to four of the above-named substituents; more preferably, the aryl group is unsubstituted, mono-, di- or tri-substituted with one to three of the above-named substituents; most preferably, the aryl group is unsubstituted, mono- or di-substituted with one to two of the above-named substituents.

Whenever the term "alkyl" or "aryl" or either of their prefix roots appear in a name of a substituent (e.g., aryl $CO_8$ alkyl) it shall be interpreted as including those limitations given above for "alkyl" and "aryl." Designated numbers of carbon atoms (e.g., $C_{1-10}$) shall refer independently to the number of carbon atoms in an alkyl or cyclic alkyl moiety or to the alkyl portion of a larger substituent in which alkyl appears as its prefix root.

The terms "arylalkyl" and "alkylaryl" include an alkyl portion where alkyl is as defined above and to include an aryl portion where aryl is as defined above. Examples of arylalkyl include, but are not limited to, benzyl, fluorobenzyl, chlorobenzyl, phenylethyl, phenylpropyl, fluorophenylethyl, chlorophenylethyl, thienylmethyl, thienylethyl, and thienylpropyl. Examples of alkylaryl include, but are not limited to, toluene, ethylbenzene, propylbenzene, methylpyridine, ethylpyridine, propylpyridine and butylpyridine.

In the compounds of the present invention, two $R^1$ substituents, when on the same carbon atom, can be taken together with the carbon to which they are attached to form a carbonyl group.

In the compounds of the present invention, two $R^3$ substituents, when on the same carbon atom, can be taken together with the carbon atom to which they are attached to form a carbonyl group. In such instances, the limitation, that in the resultant compound the carbon atom or atoms to which $R^3$ is attached is itself attached to no more than one heteroatom, does not apply. Also, in the compounds of the present invention, two $R^3$ substituents, when on the same carbon atom, can be taken together with the carbon atom to which they are attached to form a cyclopropyl group.

In the compounds of the present invention, $R^4$ and $R^5$ can be taken together with the carbon atom to which they are attached to form a carbonyl group. In such instances, the limitation, that in the resultant compound the carbon atom to which $R^4$ and $R^5$ is attached is itself attached to no more than one heteroatom, does not apply.

In the compounds of the present invention, two $R^9$ substituents, when on the same carbon atom, can be taken together with the carbon atom to which they are attached to form a $C_3$–$C_6$ cycloalkyl group.

The term "halogen" shall include iodine, bromine, chlorine, and fluorine.

The term "oxy" means an oxygen (O) atom. The term "thio" means a sulfur (S) atom. The term "oxo" means "=O". The term "carbonyl" means "C=O."

The term "substituted" shall be deemed to include multiple degrees of substitution by a named substitutent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

Under standard nomenclature used throughout this disclosure, the terminal portion of the designated side chain is described first, followed by the adjacent functionality toward the point of attachment. For example, a $C_{1-5}$ alkylcarbonylamino $C_{1-6}$ alkyl substituent is equivalent to

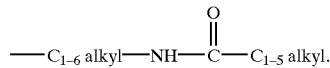

In choosing compounds of the present invention, one of ordinary skill in the art will recognize that the various substituents, i.e. W, Y, Z, $R^1$, $R^2$, $R^3$, $R^4$, $R^5$, $R^6$, $R^7$, $R^8$, and $R^9$, and the subscripts m, n, p, r, s, and t are to be chosen in conformity with well-known principles of chemical structure connectivity.

Representative compounds of the present invention typically display submicromolar affinity for the integrin receptors, particularly the αvβ3 and/or αvβ5 receptors. Compounds of this invention are therefore useful for treating mammals suffering from a bone condition caused or mediated by increased bone resorption, who are in need of such therapy. Pharmacologically effective amounts of the compounds, including pharmaceutically acceptable salts thereof, are administered to the mammal, to inhibit the activity of mammalian osteoclasts.

The compounds of the present invention are administered in dosages effective to antagonize the αvβ3 receptor where such treatment is needed, as, for example, in the prevention or treatment of osteoporosis.

Further exemplifying the invention is the method wherein the integrin receptor antagonizing effect is an αvβ3 antagonizing effect. An illustration of the invention is the method wherein the αvβ3 antagonizing effect is selected from inhibition of bone resorption, restenosis, angiogenesis, diabetic retinopathy, macular degeneration, inflammatory arthritis, cancer, or metastatic tumor growth. Preferably, the αvβ3 antagonizing effect is the inhibition of bone resorption.

An example of the invention is the method wherein the integrin receptor antagonizing effect is an αvβ5 antagonizing effect. More specifically, the αvβ5 antagonizing effect is selected from inhibition of: restenosis, angiogenesis, diabetic retinopathy, macular degeneration, inflammatory arthritis, cancer, or metastatic tumor growth.

Illustrating the invention is the method wherein the integrin receptor antagonizing effect is a dual $\alpha v\beta 3/\alpha v\beta 5$ antagonizing effect. More particularly, the dual $\alpha v\beta 3/\alpha v\beta 5$ antagonizing effect is selected from inhibition of bone resorption, restenosis, angiogenesis, diabetic retinopathy, macular degeneration, inflammatory arthritis, cancer, or metastatic tumor growth.

Illustrating the invention is the method wherein the $\alpha v\beta 3$ antagonizing effect is selected from inhibition of bone resorption, inhibition of restenosis, inhibition of angiogenesis, inhibition of diabetic retinopathy, inhibition of macular degeneration, inhibition of atherosclerosis and inflammatory arthritis, or inhibition of cancer or metastatic tumor growth. Preferably, the $\alpha v\beta 3$ antagonizing effect is the inhibition of bone resorption.

More particularly illustrating the invention is a pharmaceutical composition comprising any of the compounds described above and a pharmaceutically acceptable carrier. Another example of the invention is a pharmaceutical composition made by combining any of the compounds described above and a pharmaceutically acceptable carrier. Another illustration of the invention is a process for making a pharmaceutical composition comprising combining any of the compounds described above and a pharmaceutically acceptable carrier.

Further illustrating the invention is a method Of treating and/or preventing a condition mediated by antagonism of an integrin receptor in a mammal in need thereof, comprising administering to the mammal a therapeutically effective amount of any of the compounds described above. Preferably, the condition is selected from bone resorption, osteoporosis, restenosis, diabetic retinopathy, macular degeneration, angiogenesis, atherosclerosis, inflammatory arthritis, cancer, and metastatic tumor growth. More preferably, the condition is selected from osteoporosis and cancer. Most preferably, the condition is osteoporosis.

More specifically exemplifying the invention is a method of eliciting an integrin antagonizing effect in a mammal in need thereof, comprising administering to the mammal a therapeutically effective amount of any of the compounds or any of the pharmaceutical compositions described above. Preferably, the integrin antagonizing effect is an $\alpha v\beta 3$ antagonizing effect; more specifically, the $\alpha v\beta 3$ antagonizing effect is selected from inhibition of bone resorption, inhibition of restenosis, inhibition of atherosclerosis, inhibition of angiogenesis, inhibition of diabetic retinopathy, inhibition of macular degeneration, inhibition of inflammatory arthritis, or inhibition of cancer or metastatic tumor growth. Most preferably, the $\alpha v\beta 3$ antagonizing effect is inhibition of bone resorption. Alternatively, the integrin antagonizing effect is an $\alpha v\beta 5$ antagonizing effect or a dual $\alpha v\beta 3/\alpha v\beta 5$ antagonizing effect. Examples of $\alpha v\beta 5$ antagonizing effects are inhibition of restenosis, atherosclerosis, angiogenesis, diabetic retinopathy, macular degeneration, inflammatory arthritis, or metastatic tumor growth.

Additional examples of the invention are methods of inhibiting bone resorption and of treating and/or preventing osteoporosis in a mammal in need thereof, comprising administering to the mammal a therapeutically effective amount of any of the compounds or any of the pharmaceutical compositions described above.

Additional illustrations of the invention are methods of treating hypercalcemia of malignancy, osteopenia due to bone metastases, periodontal disease, hyperparathyroidism, periarticular erosions in rheumatoid arthritis, Paget's disease, immobilization-induced osteopenia, and glucocorticoid treatment in a mammal in need thereof, comprising administering to the mammal a therapeutically effective amount of any of the compounds or any of the pharmaceutical compositions described above.

More particularly exemplifying the invention is the use of any of the compounds described above in the preparation of a medicament for the treatment and/or prevention of osteoporosis in a mammal in need thereof. Still further exemplifying the invention is the use of any of the compounds described above in the preparation of a medicament for the treatment and/or prevention of bone resorption, cancer, metastatic tumor growth, restenosis, atherosclerosis, diabetic retinopathy, macular degeneration, inflammatory arthritis, and/or angiogenesis.

Also exemplifying the invention are compositions further comprising an active ingredient selected from the group consisting of a.) an organic bisphosphonate or a pharmaceutically acceptable salt or ester thereof, b.) an estrogen receptor modulator, c.) an androgen receptor modulator, d.) a cytotoxic/antiproliferative agent, e.) a matrix metalloproteinase inhibitor, f.) an inhibitor of epidermal-derived, fibroblast-derived, or platelet-derived growth factors, g.) an inhibitor of VEGF, h.) an antibody to a growth factor or to a growth factor receptor, i.) an inhibitor of Flk-1/KDR, Flt-1, Tck/Tie-2, or Tie-1, j.) a cathepsin K inhibitor, k.) a growth hormone secretagogue, l.) an inhibitor of osteoclast proton ATPase, and m.) a prenylation inhibitor, such as a farnesyl transferase inhibitor or a geranylgeranyl transferase inhibitor or a dual farnesyl/geranylgeranyl transferase inhibitor; and mixtures thereof.

(See, B. Millauer et al., "Dominant-Negative Inhibition of Flk-1 Suppresses the Growth of Many Tumor Types in Vivo", *Cancer Research*, 56, 1615–1620 (1996), which is incorporated by reference herein in its entirety).

Preferably, the active ingredient is selected from the group consisting of:

a.) an organic bisphosphonate or a pharmaceutically acceptable salt or ester thereof, b.) an estrogen receptor modulator, c.) an androgen receptor modulator, d.) an inhibitor of osteoclast proton ATPase, and e.) a cathepsin K inhibitor; and mixtures thereof.

Nonlimiting examples of such bisphosphonates include alendronate, etidronate, pamidronate, risedronate, ibandronate, and pharmaceutically acceptable salts and esters thereof. A particularly preferred bisphosphonate is alendronate, especially alendronate monosodium trihydrate.

Nonlimiting examples of estrogen receptor modulators include estrogen, progesterin, estradiol, droloxifene, raloxifene, and tamoxifene.

Nonlimiting examples of cytotoxic/antiproliferative agents are taxol, vincristine, vinblastine, and doxorubicin.

Cathepsin K, formerly known as cathepsin O2, is a cysteine protease and is described in PCT International Application Publication No. WO 96/13523, published May 9, 1996; U.S. Pat. No. 5,501,969, issued Mar. 3, 1996; and U.S. Pat. No. 5,736,357, issued Apr. 7, 1998, all of which are incorporated by reference herein in their entirety. Cysteine proteases, specifically cathepsins, are linked to a number of disease conditions, such as tumor metastasis, inflammation, arthritis, and bone remodeling. At acidic pH's, cathepsins can degrade type-I collagen. Cathepgin protease inhibitors can inhibit osteoclastic bone resorption by inhibiting the degradation of collagen fibers and are thus useful in the treatment of bone resorption diseases, such as osteoporosis.

The proton ATPase which is found on the apical membrane of the osteoclast has been reported to play a significant role in the bone resorption process. Therefore, this proton pump represents an attractive target for the design of inhibitors of bone resorption which are potentially useful for the treatment and prevention of osteoporosis and related metabolic diseases (see C. Farina et al., "Selective inhibitors of the osteoclast vacuolar proton ATPase as novel bone antiresorptive agents," *DDT*, 4:163–172 (1999)).

Evidence has been presented that androgenic steroids play a physiological role in the development of bone mass in men and women and that androgens act directly on bone. Androgen receptors have been demonstrated in human osteoblast-like cell lines and androgens have been shown to directly stimulate bone cell proliferation and differentiation. For a discussion, reference is made to S. R. Davis, "The therapeutic use of androgens in women," *J. Steroid Biochem. Mol. Biol.*, 69: 177–184 (1999) and K. A. Hansen and S. P. T. Tho, "Androgens and Bone Health," *Seminars in Reproductive Endocrinology*," 16: 129–134 (1998). Thus, androgen receptor modulators may have utility in the treatment and prevention of bone loss in women.

The present invention is also directed to combinations of the compounds of the present invention with one or more agents useful in the prevention or treatment of osteoporosis. For example, the compounds of the instant invention may be effectively administered in combination with effective amounts of other agents such as an organic bisphosphonate, an estrogen receptor modulator, an androgen receptor modulator, a cathepsin K inhibitor, or an inhibitor of the osteoclast proton ATPase.

Additional illustrations of the invention are methods of treating metastatic tumor growth in a mammal in need thereof, comprising administering to the mammal a therapeutically effective amount of a compound described above and one or more agents known to be cytotoxic/antiproliferative. Also, the compounds of the present invention can be administered in combination with radiation therapy for treating cancer and metastatic tumor growth.

In addition, the integrin αvβ3 antagonist compounds of the present invention may be effectively administered in combination with a growth hormone secretagogue in the therapeutic or prophylactic treatment of disorders in calcium or phosphate metabolism and associated diseases. These diseases include conditions which can benefit from a reduction in bone resorption. A reduction in bone resorption should improve the balance between resorption and formation, reduce bone loss or result in bone augmentation. A reduction in bone resorption can alleviate the pain associated with osteolytic lesions and reduce the incidence and/or growth of those lesions. These diseases include: osteoporosis (including estrogen deficiency, immobilization, glucocorticoid induced and senile), osteodystrophy, Paget's disease, myositis ossificans, Bechterew's disease, malignant hypercalcemia, metastatic bone disease, periodontal disease, cholelithiasis, nephrolithiasis, urolithiasis, urinary calculus, hardening of the arteries (sclerosis), arthritis, bursitis, neuritis and tetany. Increased bone resorption can be accompanied by pathologically high calcium and phosphate concentrations in the plasma, which would be alleviated by this treatment. Similarly, the present invention would be useful in increasing bone mass in patients with growth hormone deficiency. Thus, preferred combinations are simultaneous or alternating treatments of an αvβ3 receptor antagonist of the present invention and a growth hormone secretagogue, optionally including a third component comprising an organic bisphosphonate, preferably alendronate monosodium trihydrate.

In accordance with the method of the present invention, the individual components of the combination can be administered separately at different times during the course of therapy or concurrently in divided or single combination forms. The instant invention is therefore to be understood as embracing all such regimes of simultaneous or alternating treatment, and the term "administering" is to be interpreted accordingly. It will be understood that the scope of combinations of the compounds of this invention with other agents useful for treating integrin-mediated conditions includes in principle any combination with any pharmaceutical composition useful for treating osteoporosis.

As used herein, the term "composition" is intended to encompass a product comprising the specified ingredients in the specified amounts, as well as any product which results, directly or indirectly, from combination of the specified ingredients in the specified amounts.

The compounds of the present invention can be administered in such oral dosage forms as tablets, capsules (each of which includes sustained release or timed release formulations), pills, powders, granules, elixirs, tinctures, suspensions, syrups and emulsions. Likewise, they may also be administered in intravenous (bolus or infusion), intraperitoneal, topical (e.g., ocular eyedrop), subcutaneous, intramuscular or transdermal (e.g., patch) form, all using forms well known to those of ordinary skill in the pharmaceutical arts. An effective but non-toxic amount of the compound desired can be employed as an αvβ3 antagonist.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician, veterinarian or clinician can readily determine and prescribe the effective amount of the drug required to prevent, counter or arrest the progress of the condition.

Oral dosages of the present invention, when used for the indicated effects, will range between about 0.01 mg per kg of body weight per day (mg/kg/day) to about 100 mg/kg/day, preferably 0.01 to 10 mg/kg/day, and most preferably 0.1 to 5.0 mg/kg/day. For oral administration, the compositions are preferably provided in the form of tablets containing 0.01, 0.05, 0.1, 0.5, 1.0, 2.5, 5.0, 10.0, 15.0, 25.0, 50.0, 100 and 500 milligrams of the active ingredient for the symptomatic adjustment of the dosage to the patient to be treated. A medicament typically contains from about 0.01 mg to about 500 mg of the active ingredient, preferably, from about 1 mg to about 100 mg of active ingredient. Intravenously, the most preferred doses will range from about 0.1 to about 10 mg/kg/minute during a constant rate infusion. Advantageously, compounds of the present invention may be administered in a single daily dose, or the total daily dosage may be administered in divided doses of two, three or four times daily. Furthermore, preferred compounds for the present invention can be administered in intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittent throughout the dosage regimen.

In the methods of the present invention, the compounds herein described in detail can form the active ingredient, and are typically administered in admixture with suitable pharmaceutical diluents, excipients or carriers (collectively referred to herein as 'carrier' materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamide-phenol, polyhydroxy-ethylaspartamide-phenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and crosslinked or amphipathic block copolymers of hydrogels.

In the schemes and examples below, various reagent symbols and abbreviations have the following meanings:

AcOH: Acetic acid.
BH$_3$.DMS: Borane.dimethylsulfide.
BOC(Boc): t-Butyloxycarbonyl.
BOP: Benzotriazol-1-yloxytris(dimethylamino) phosphonium hexafluorophosphate.
CBZ(Cbz): Carbobenzyloxy or benzyloxycarbonyl.
CDI: Carbonyldiimidazole.
CH$_2$Cl$_2$: Methylene chloride.
CH$_3$CN: Acetonitrile
CHCl$_3$: Chloroform.
DCE: 1,2 Dichloroethane
DEAD: Diethyl azodicarboxylate.
DIAD: Diisopropyl azodicarboxylate.
DIBAH or
DIBAL-H: Diisobutylaluminum hydride.
DIPEA: Diisopropylethylamine.
DMAP: 4-Dimethylaminopyridine.
DME: 1,2-Dimethoxyethane.
DMF: Dimethylformamide.
DMSO: Dimethylsulfoxide.
DPFN: 3,5-Dimethyl-1-pyrazolylformamidine nitrate.
EDC: 1-(3-Dimethylaminopropyl)-3-ethylcarbodiimide.HCl
EtOAc: Ethyl acetate.
EtOH: Ethanol.
HOAc: Acetic acid.
HOAT: 1-Hydroxy-7-azabenzotriazole
HOBT: 1-Hydroxybenzotriazole.
HPLC: High-performance liquid chromatography
IBCF: Isobutylchloroformate
LDA: Lithium diisopropylamide.
MeOH: Methanol.
MNNG 1,1-methyl-3-nitro-1-nitrosoguanidine
NEt$_3$: Triethylamine.
NMM: N-methylmorpholine.
PCA.HCl: Pyrazole carboxamidine hydrochloride.
Pd/C: Palladium on activated carbon catalyst.
Ph: Phenyl.
pTSA p-Toluenesulfonic acid.
TEA: Triethylamine.
TFA: Trifluoroacetic acid.
THF: Tetrahydrofuran.
TLC: Thin Layer Chromatography.
TMEDA: N,N,N',N'-Tetramethylethylenediamine.
TMS: Trimethylsilyl.

The novel compounds of the present invention can be prepared according to the procedure of the following schemes and examples, using appropriate materials and are further exemplified by the following specific examples. The compounds illustrated in the examples are not, however, to be construed as forming the only genus that is considered as the invention. The following examples further illustrate details for the preparation of the compounds of the present invention. Those skilled in the art will readily understand that known variations of the conditions and processes of the following preparative procedures can be used to prepare these compounds. All temperatures are degrees Celsius unless otherwise noted.

SCHEME 1
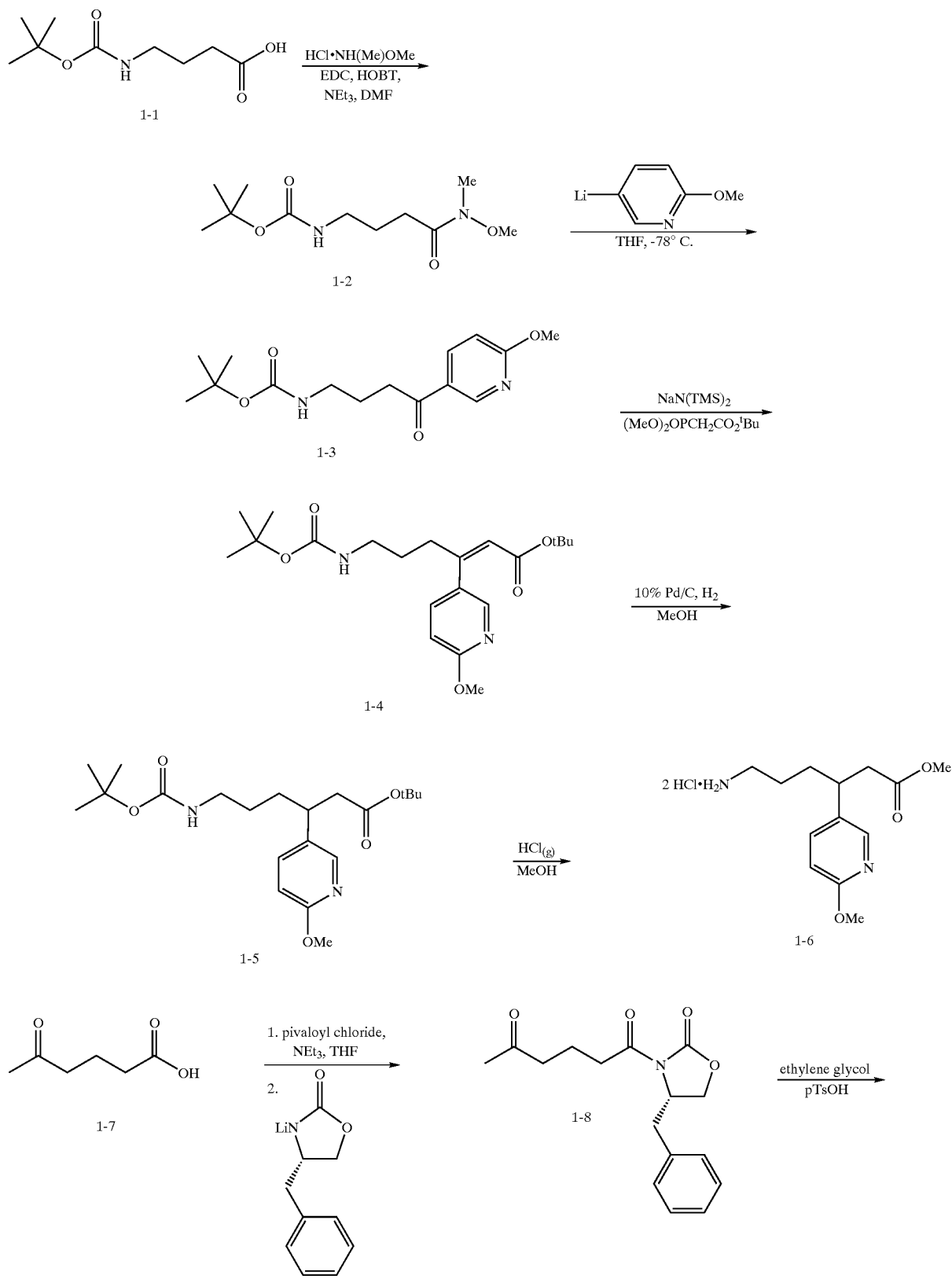

-continued
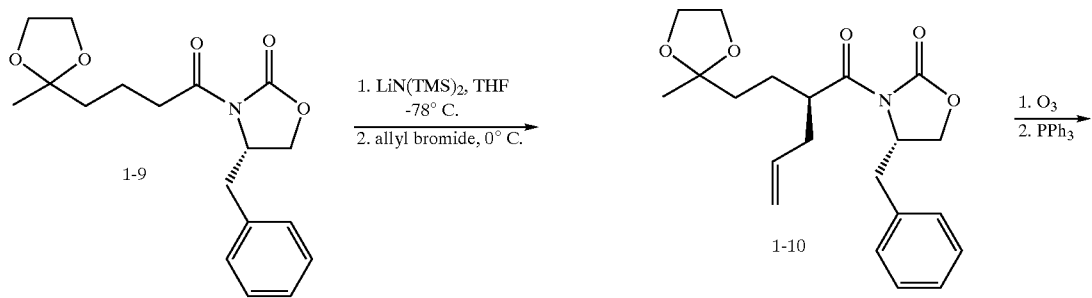
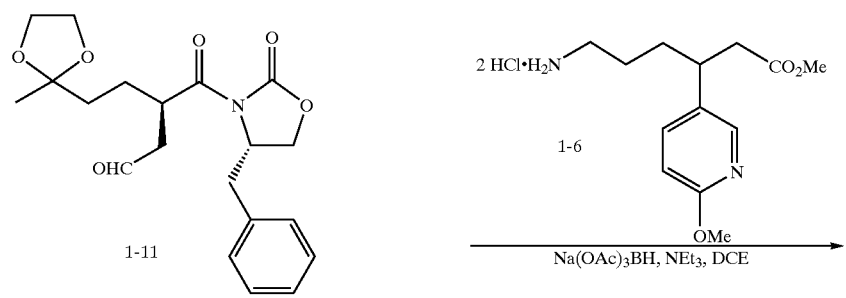
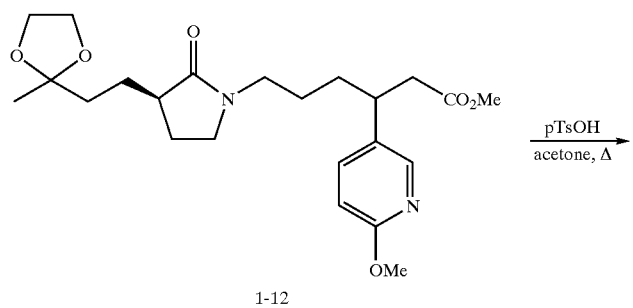
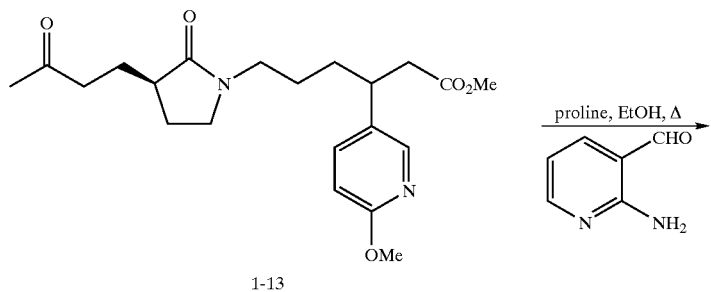
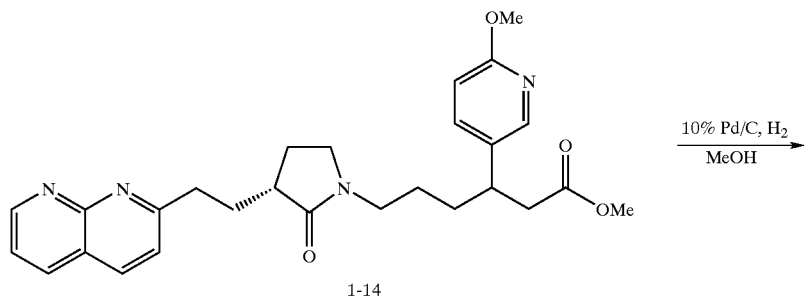

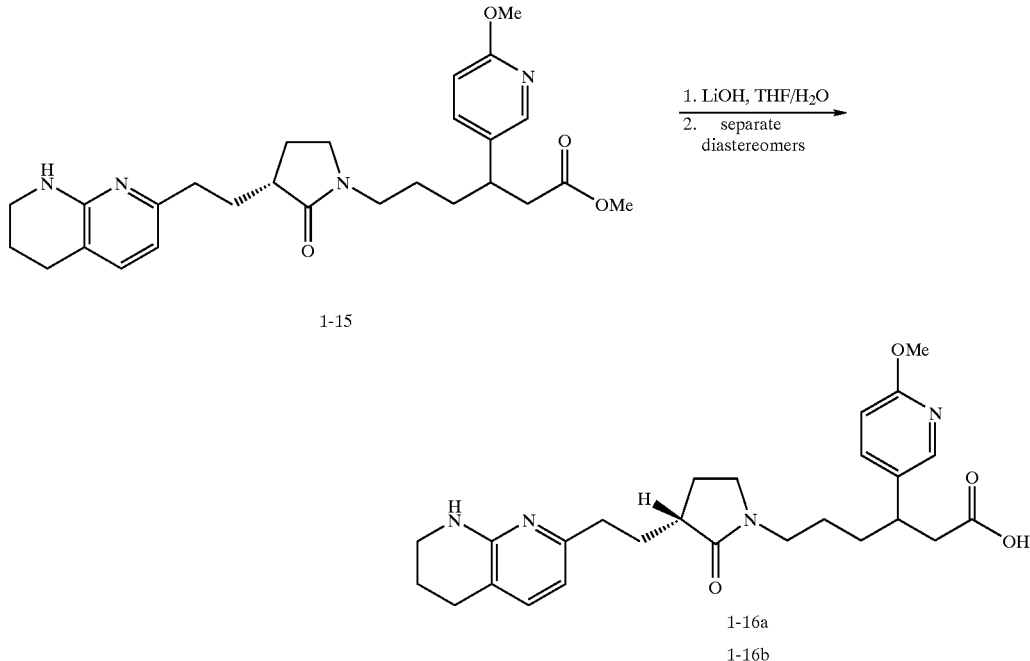

EXAMPLE 1

[3-(N-Methoxy-N'-methyl-carbamoyl)-propyl]-carbamic Acid-tert-butyl Ester (1-2)

4-t-Butoxycarbonylaminobutyric acid 1-1 (10 g, 49.2 mmol) was combined with N,O-dimethylhydroxylamine hydrochloride (4.8 g 49.2 mmol), EDC (99.4 g, 49,2 mmol), HOBT (6.6 g, 49.2 mmol) and NMM (5.4 mL, 49.2 mmol) in DMF (50 mL) and stirred under argon overnight. The reaction mixture was diluted with EtOAc (200 mL) and washed with saturated aqueous sodium chloride, and dried over anhydrous magnesium sulfate, filtered and evaporated affording 1-2 as a yellow oil.

$^1$H NMR (300 MHz, CDCl$_3$): δ 4.80 (br. s, 1H), 3.68 (s, 3H), 3.18 (s, 3H), 3.08 (t, J=7 Hz, 2H), 2.43 (t, J=7 Hz, 2H), 1.81 (m, 2H), 1.43 (s, 9H).

[4-(6-Methoxy-pyridin-3-yl)-4-oxo-butyl]-carbamic Acid tert-Butyl Ester (1-3)

To a stirred solution of 5-bromo-2-methoxypyridine (7.65 g, 40.7 mmol) in tetrahydrofuran (125 mL) at −78° C. under argon was added a solution of butyllithium (16.2 mL of a 2.5 M solution). After 5 min., a solution of 1-2 (2.0 g, 8.12 mmol) in tetrahydrofuran (25 mL) was added. After 15 min, saturated aqueous sodium hydrogen carbonate was added, and the reaction mixture was allowed to warm to ambient temperature. The mixture was extracted with ethyl acetate, and the organic layer was washed with saturated aqueous sodium chloride, and dried over anhydrous magnesium sulfate. The reaction mixture was filtered and concentrated at reduced pressure to give an oil that was purified by flash column chromatography (silica gel, 25 to 50% ethyl acetate/hexanes) to give 1-3 as an oil.

$^1$H NMR (300 MHz, CDCl$_3$) δ 8.79 (d, J=2.5 Hz, 1H), 8.14 (dd, J=2.4, 8.5 Hz, 1H), 6.78 (d, J=8.8 Hz, 1H), 4.66 (br. s, 1H), 4.01 (s, 3H), 3.55–3.33 (m, 2H), 2.94 (app. t, J=7.2 Hz, 2H), 1.94 (app. quintet, J=7.0 Hz, 2H), 1.43 (s, 9H).

6-tert-Butoxycarbonylamino-3-(6-methoxy-pyridin-3-yl)-hex-2-enoic Acid tert-Butyl Ester (1-4)

To a stirred solution of t-butyl dimethylphosphonoacetate (6.86 g, 30.6 mmol) in tetrahydrofuran (150 mL) at −78° C. under argon was added a solution of sodium bis(trimethylsilylamide) (30.6 mL of a 1.0 M solution). After 15 min., a solution of 1-3 (3.0 g, 10.2 mmol) in tetrahydrofuran (30 mL) was added, and the reaction was warmed to ambient temperature, then heated to 40° C. for 1 h. The reaction mixture was then cooled to ambient temperature, diluted with ethyl acetate and washed with saturated aqueous sodium hydrogen carbonate, then saturated aqueous sodium chloride, and dried over anhydrous magnesium sulfate. The reaction mixture was filtered and concentrated at reduced pressure to give an oil that was purified by flash column chromatography (silica gel, 15 to 25% ethyl acetate/hexanes) to give 1-4 and its 2 isomer.

E isomer:

$^1$H NMR (300 MHz, CDCl$_3$) δ 8.22 (d, J=2.3 Hz, 1H), 7.63 (dd, J=2.4, 8.6 Hz, 1H), 6.73 (d, J=8.7 Hz, 1H), 5.97 (s, 1H), 5.18 (br. s, 1H), 3.95 (s, 3H), 3.15–3.05 (m, 4H), 1.66–1.58 (m, 3H), 1.52 (s, 9H), 1.43 (s, 9H).

Z isomer:

$^1$H NMR (300 MHz, CDCl$_3$) δ 7.98 (d, J=2.4 Hz, 1H), 7.42 (dd, J=2.4, 8.5 Hz, 1H), 6.75 (d, J=8.7 Hz, 1H), 5.83 (s, 1H), 4.50 (br. s, 1H), 3.95 (s, 3H), 3.19–3.05 (m, 2H), 2.47–2.40 (m, 2H), 1.62–1.50 (m, 2H), 1.43 (s, 9H), 1.33 (s, 9H).

6-tert-Butoxycarbonylamino-3-(6-methoxy-pyridin-3-yl)-hexanoic Acid tert-Butyl Ester (1-5)

To a stirred solution of a mixture of 1-4 and its Z isomer (3.5 g) in methanol (75 mL) was added a slurry of 10% palladium on carbon (700 mg) in ethanol (10 mL). The resulting suspension was stirred under a slight overpressure of hydrogen for 16 h. The reaction mixture was filtered through Celite and concentrated at reduced pressure to give 1-5 as an oil.

$^1$H NMR (300 MHz, CDCl$_3$) δ 7.96 (d, J=2.4 Hz, 1H), 7.40 (dd, J=2.7, 8.5 Hz, 1H), 6.70 (d, J=8.5 Hz, 1H), 4.48 (br. s, 1H), 3.91 (s, 3H), 3.18–2.92 (m, 4H), 2.57–2.35 (m, 2H), 1.78–1.30 (m, 3H), 1.42 (s, 9H), 1.30 (s, 9H).

6-Amino-3-(6-methoxy-pyridin-3-yl)-hexanoic Acid Methyl Ester Dihydrochloride (1-6)

To a stirred solution of 1-5 (1.5 g) in methanol (70 mL) at 0° C. was bubbled hydrogen chloride. After 15 min, the addition of gas was ceased, and the reaction mixture was warmed to ambient temperature for 3 h. The mixture was then concentrated at reduced pressure to give 1-6 as its dihydrochloride salt as a solid.

$^1$H NMR (300 MHz, CD$_3$OD) δ 8.52 (d, J=8.5 Hz, 1H), 8.35 (br. s, 1H), 7.62 (d, J=8.5 Hz, 1H), 4.25 (s, 3H), 3.58 (s, 3H), 3.36–3.25 (m, 2H), 3.00–2.72 (m, 4H), 1.90–1.43 (m, 4H).

1-(4(S)-Benzyl-2-oxo-oxazolidin-3-yl)-hexane-1,5-dione (1-8)

To a stirred solution of 4-acetylbutyric acid 1-7 (25.0 g, 192 mmol), triethylamine (29.5 ml, 211 mmol) in tetrahydrofuran (500 mL) at −78° C. was added pivaloyl chloride (26.0 ml, 211 mmol). After 20 min, the mixture was warmed to 0° C. for 1.0 h and then recooled to −78° C. To a stirred solution of (S)-(−)-4-benzyl-2-oxazolidinone (37.4 g, 211 mmol) in tetrahydrofuran (500 ml) at −78° C. was added nBuLi (84.5 ml, 211 mmol, 2.5M in hexanes) dropwise over 10 minutes. After 20 minutes, the lithium reagent was transferred to the mixed anhydride via cannula. After 10 minutes, the reaction was warmed to 0° C. for 1.0 h. The mixture was diluted with ethyl acetate, washed with saturated aqueous sodium hydrogen carbonate, saturated aqueous sodium chloride, and dried over anhydrous magnesium sulfate. The reaction mixture was filtered and concentrated at reduced pressure to give 1-8 as a solid which was triturated with ethyl ether and filtered to give a white solid.

$^1$H NMR (300 MHz, CDCl$_3$) δ 7.38–7.21 (m, 5H), 4.65–4.42 (m, 2H), 4.26–4.15 (m, 1H), 3.30 (dd, J=3.1, 13.2 Hz, 1H), 2.99–2.91 (m, 2H), 2.76 (dd, J=9.8, 13.5 Hz, 1H), 2.60–2.53 (m, 2H), 2.17 (s, 3H), 2.07–1.91 (m, 2H).

4(S)-Benzyl-3-[4-(2-methyl-[1,3]dioxolan-2-yl)-butyryl]-oxazolidin-2-one (1-9)

To a stirred solution of 1-8 (45 g, 156 mmol) and ethylene glycol (13.0 mL, 223 mmol) in benzene (500 mL) was added catalytic p-toluenesulfonic acid (125 mg). The resulting mixture was heated at strong reflux with azeotropic removal of water for 4 h. The mixture was cooled to ambient temperature, diluted with ethyl acetate and washed with water, saturated aqueous sodium hydrogen carbonate, saturated aqueous sodium chloride, and dried over anhydrous magnesium sulfate. The reaction mixture was filtered and concentrated at reduced pressure to give 1-9 as a yellow oil, which crystallized on standing.

$^1$H NMR (300 MHz, CDCl$_3$) δ 7.40–7.15 (m, 5H), 4.73–4.62 (m, 1H), 4.25–4.16 (m, 2H), 3.95 (m, 4H), 3.30 (dd, J=3.3, 13.4 Hz, 1H), 3.04–2.86 (m, 2H), 2.76 (dd, J=9.8, 13.5 Hz, 1H), 1.79–1.71 (m, 4H), 1.35 (s, 3H).

4(S)-Benzyl-3-{2(R)-[2-(2-methyl-[1,3]dioxolan-2-yl)-ethyl]-pent-4-enoyl}-oxazolidin-2-one (1-10)

To a stirred solution of 1-9 (19.3 g, 57.9 mmol) in tetrahydrofuran (400 mL) at −78° C. under argon was added a solution of lithium bis(trimethylsilyl)amide (75.2 mL of a 1.0 M solution in tetrahydrofuran) over 20 min. After an additional 20 min., allyl bromide (14.0 g, 116 mmol) was added in one portion. After 20 min., the reaction mixture was allowed to warm to 0° C. After 3.5 h, the reaction mixture was diluted with ethyl acetate, washed with water, saturated aqueous sodium hydrogen carbonate, saturated aqueous sodium chloride, and dried over anhydrous magnesium sulfate. The reaction mixture was filtered and concentrated at reduced pressure. The resulting oil was purified by flash column chromatography (silica gel, 25 to 35% ethyl acetate/hexanes) to give 1-10 as an oil.

$^1$H NMR (300 MHz, CDCl$_3$) δ 7.39–7.22 (m, 5H), 5.90–5.79 (m, 1H), 5.13–5.03 (m, 2H), 4.72–4.65 (m, 1H), 4.20–4.13 (m, 2H), 3.98–3.88 (m, 4H), 3.29 (dd, J=3.3, 13.4 Hz, 1H), 3.04 –2.86 (m, 2H), 2.66 (dd, J=10.0, 13.2 Hz, 1H), 2.53–2.28 (m, 2H), 1.88–1.78 (m, 1H), 1.68–1.59 (m, 3H), 1.31 (s, 3H).

3(R)-(4(S)-Benzyl-2-oxo-oxazolidine-3-carbonyl)-5-(2-methyl-[1,3]dioxolan-2-yl)-pentanal (1-11)

To a stirred solution of 1-10 (16.0 g, 42.8 mmol) and Sudan III dye (10 mg) in dichloromethane (500 mL) at −78° C. was bubble ozone until the color of the dye was discharged (45 min.), after which time the solution was purged with argon for 0.5 h. Triphenylphosphine (16.9 g, 64.3 mmol) was added and the solution was allowed to warm to ambient temperature for 3 h. The reaction mixture was concentrated at reduced pressure and the resulting oil was purified by flash column chromatography (silica gel, 10 to 20% ethyl acetate/dichloromethane) to give 1-11 as an oil which crystallized on standing.

$^1$H NMR (300 MHz, CDCl$_3$) δ 9.78 (s, 1H), 7.39–7.22 (m, 5H), 4.70–4.60 (m, 1H), 4.30–4.18 (m, 3H), 3.97–3.85 (m, 4H), 3.29 (dd, J=3.3, 13.7 Hz, 1H), 3.08 (dd, J=9.8, 18.3 Hz, 1H), 2.79 (dd, J=9.8, 13.4 Hz, 1H), 2.66 (dd, J=3.3, 18.0 Hz, 2H), 1.88–1.55 (m, 4H), 1.30 (s, 3H).

3-(6-Methoxy-pyridin-3-yl)-6-{3(R)-[2-(2-methyl-[1,3]dioxolan-2-yl)-ethyl]2-oxo-pyrrolidin-1-yl}-hexanoic Acid Methyl Ester (1-12)

To a stirred suspension of 1-11 (530 mg, 1.41 mmol), 1-6(460 mg, 1.41 mmol) and triethylamine (0.59 mL, 4.24 mmol) in 1,2-dichloroethane (15 mL) was added sodium triacetoxyborohydride (449 mg, 2.12 mmol) and the mixture was stirred for 16 h. The reaction mixture was diluted with ethyl acetate and washed with saturated aqueous sodium hydrogen carbonate, saturated aqueous sodium chloride, and dried over anhydrous magnesium sulfate. The reaction mixture was filtered and concentrated at reduced pressure. The resulting oil was purified by flash column chromatography (silica gel, 3:0.3:0.3 to 8:0.8:0.8% ethanol/ammonium hydroxide/water in ethyl acetate) to give 1-12 as an inseparable mixture of diastereomers.

$^1$H NMR (300 MHz, CDCl$_3$) δ 7.97 (d, J=2.2 Hz, 1H), 7.40 (dd, J=2.6, 8.6 Hz, 1H), 6.71 (d, J=8.6 Hz, 1H), 3.95–3.90 (m, 4H), 3.92 (s, 3H), 3.59 (s, 3H), 3.30–3.13 (m, 4H), 3.12–3.00 (m, 1H), 2.68–2.51 (m, 2H), 2.43–2.33 (m, 1H), 2.24–2.11 (m, 1H), 2.05–1.90 (m, 1H), 1.78–1.25 (m, 8H), 1.33 (s, 3H).

3-(6-Methoxy-pyridin-3-yl)-6-[2-oxo-3(R)-(3-oxo-butyl)-pyrrolidin-1-yl]-hexanoic Acid Methyl Ester (1-13)

To a stirred solution of 1-12 (440 mg) in acetone (30 mL) was added p-toluenesulfonic acid (270 mg) and the mixture was heated at reflux for 2 h, then cooled to ambient temperature for 3 h. The reaction mixture was concentrated at reduced pressure. The residue was diluted with ethyl acetate and washed with saturated aqueous sodium hydrogen carbonate, saturated aqueous sodium chloride, and dried over anhydrous magnesium sulfate. The reaction mixture was filtered and concentrated at reduced pressure to give 1-13 as an oil, which was used in the next step without further purification.

$^1$H NMR (300 MHz, CDCl$_3$) δ 8.48–8.45 (m, 1H), 8.26–8.20 (m, 1H), 7.26–7.21 (m, 1H), 4.19 (s, 3H), 3.60 (s,

3H), 3.40–3.19 (m, 5H), 2.76–2.46 (m, 5H), 2.25–2.10 (m, 5H), 2.05–1.88 (m, 1H), 1.78–1.60 (m, 4H), 1.56–1.35 (m, 2H).

3-(6-Methoxy-pyridin-3-yl)-6-{2-oxo-3(R)-[2-(5,6,7,8-tetrahydro-[1,8]naphthyridin-2-yl)-ethyl]-pyrrolidin-1-yl}-hexanoic Acid Methyl Ester (1-15)

A stirred solution of 2-amino-3-formylpyridine (1.40 mmol), 1-13 (420 mg, 1.08 mmol) and proline (162 mg, 1.40 mmol) in ethanol (10 mL) was heated at reflux for 14 h, and the cooled to ambient temperature. The reaction mixture was diluted with ethyl acetate and washed with saturated aqueous sodium hydrogen carbonate, saturated aqueous sodium chloride, and dried over anhydrous magnesium sulfate. The reaction mixture was filtered and concentrated at reduced pressure. The resulting oil was purified by flash column chromatography (silica gel, 3:0.3:0.3 to 8:0.8:0.8% ethanol/ammonium hydroxide/water in ethyl acetate) to give 1-14 as an inseparable mixture of diastereomers. To a stirred solution of this mixture in methanol (20 mL) was added a slurry of 10% palladium on carbon (80 mg) in ethanol (2 mL). The resulting suspension was stirred under a slight overpressure of hydrogen for 16 h. The reaction mixture was filtered through Celite and concentrated at reduced pressure. The resulting oil was purified by flash column chromatography (silica gel, 3:0.3:0.3 to 8:0.8:0.8% ethanol/ammonium hydroxide/water in ethyl acetate) to give 1-15 as an inseparable mixture of diastereomers.

$^1$H NMR (300 MHz, CDCl$_3$) δ 8.00–7.93 (m, 1H), 7.43–7.38 (m, 1H), 7.05 (d, J=7.3 Hz, 1H), 6.69 (d, J=7.3 Hz, 1H), 6.39 (d, J=8.6 Hz, 1H), 4.79 (br. s, 1H), 3.95 (s, 3H), 3.59 (s, 3H), 3.49–3.35 (m, 2H), 3.27–3.01 (m, 5H), 2.73–2.50 (m, 6H), 2.49–2.30 (m, 1H), 2.28–2.11 (m, 2H), 1.95–1.22 (m, 9H).

3-(6-Methoxy-pyridin-3-yl)-6-{2-oxo-3(R)-[2-(5,6,7,8-tetrahydro-[1,8]naphthyridin-2-yl)-ethyl]-pyrrolidin-1-yl}-hexanoic Acid (1-16)

To a stirred solution of 1-15 (190 mg) in tetrahydrofuran (7 mL) was added lithium hydroxide monohydrate (70 mg) in water (7 mL) and the mixture was stirred for 16 h. The reaction mixture was then concentrated at reduced pressure and resulting oil was purified by flash column chromatography (silica gel, 30:3:3 to 50:5:5% ethanol/ammonium hydroxide/water in ethyl acetate) to give 1-16 as a mixture of diastereomers.

$^1$H NMR (300 MHz, CD$_3$OD) δ 8.06–7.96 (m, 1H), 7.63–7.57 (m, 1H), 6.80–6.75 (m, 1H), 6.56–6.48 (m, 1H), 3.86 (s, 3H), 3.60–3.38 (m, 4H), 3.30 (s, 3H), 3.28–1.25 (m, 20H).

The diastereomers 1-16a and 1-16b were separated by chiral HPLC using the following conditions to provide the first eluting isomer (1-16a) and the second eluting isomer (1-16b): Chiralpak AD 25×4.6 cm column; 60:40:0.5 hexane/ethanol/trifluoroacetic acid, flow: 1.0 mL/min.

3(R or S)-(6-Methoxy-pyridin-3-yl)-6-{2-oxo-3(R)-[2-(5,6,7,8-tetrahydro-[1,8]naphthyridin-2-yl)-ethyl]-pyrrolidin-1-yl}-hexanoic Acid (1-16a)

$^1$H NMR (300 MHz, CD$_3$OD) δ 8.00 (d, J=2.3 Hz, 1H), 7.61 (dd, J=2.4, 8.4 Hz, 1H), 7.43 (d, J=7.2 Hz, 1H), 6.77 (d, J=8.6 Hz, 1H), 6.52 (d, J=7.2 Hz, 1H), 3.86 (s, 3H), 3.62–3.37 (m, 4H), 3.28–1.25 (m, 20H).

3(S or R)-(6-Methoxy-pyridin-3-yl)-6-{2-oxo-3(R)-[2-(5,6,7,8-tetrahydro-[1,8]naphthyridin-2-yl)-ethyl]-pyrrolidin-1-yl}-hexanoic Acid (1-16b)

$^1$H NMR (300 MHz, CD$_3$OD) δ 8.02 (d, J=2.4 Hz, 1H), 7.63 (dd, J=2.4, 8.5 Hz, 1H), 7.39 (d, J=7.3 Hz, 1H), 6.77 (d, J=8.4 Hz, 1H), 6.49 (d, J=7.2 Hz, 1H), 3.88 (s, 3H), 3.61–3.38 (m, 4H), 3.28–1.25 (m, 20H).

SCHEME 2

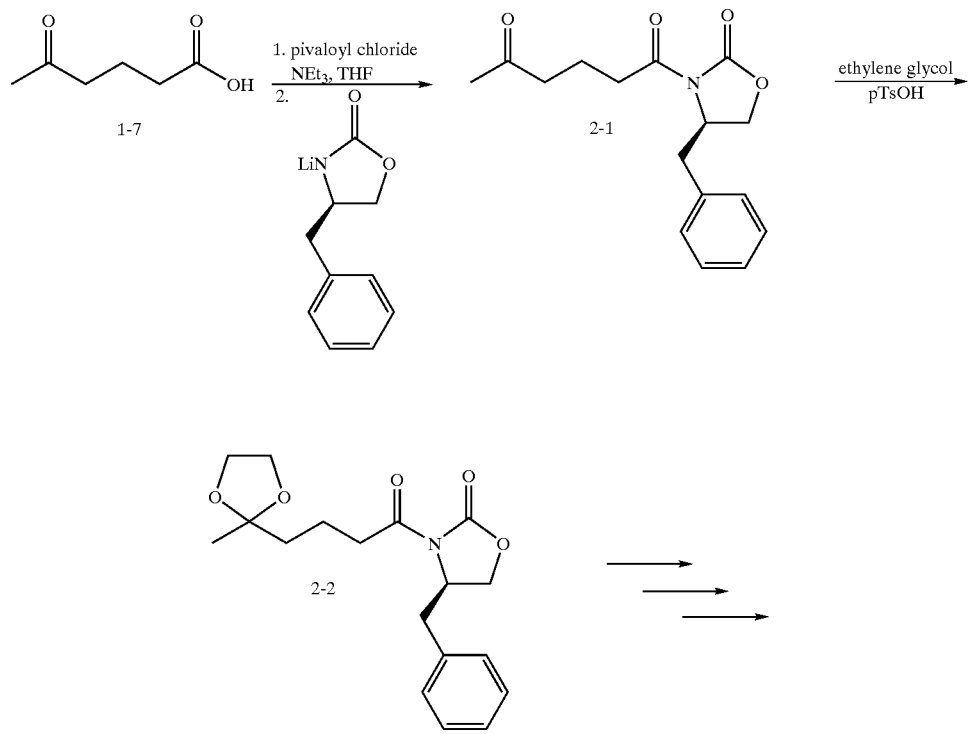

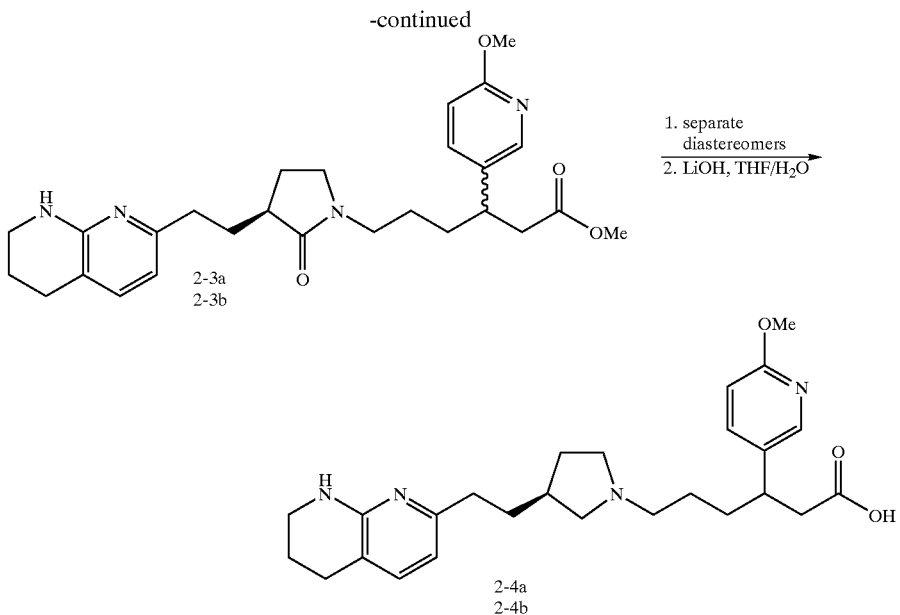

EXAMPLE 2

1-(4(R)-Benzyl-2-oxo-oxazolidin-3-yl)-hexane-1,5-dione (2-1)

To a stirred solution of 4-acetylbutyric acid (1-7) (25.0 g, 192 mmol), triethylamine (29.5 ml, 211 mmol) in tetrahydrofuran (500 mL) at −78° C. was added pivaloyl chloride (26.0 ml, 211 mmol). After 20 min, the mixture was warmed to 0° C. for 1.0 h and then recooled to −78° C. To a stirred solution of (R)-(−)-4-benzyl-2-oxazolidinone (37.4 g, 211 mmol) in tetrahydrofuran (500 ml) at −78° C. was added nBuLi (84.5 ml, 211 mmol, 2.5M in hexanes) dropwise over 10 minutes. After 20 minutes, the lithium reagent was transferred to the mixed anhydride via cannula. After 10 minutes, the reaction was warmed to 0° C. for 1.0 h. The mixture was diluted with ethyl acetate, washed with saturated aqueous sodium hydrogen carbonate, saturated aqueous sodium chloride, and dried over anhydrous magnesium sulfate. The reaction mixture was filtered and concentrated at reduced pressure to give 2-1 as a solid which was triturated with ethyl ether and filtered to give a white solid.

$^{1}$H NMR (300 MHz, CDCl$_3$) δ 7.38–7.21 (m, 5H), 4.65–4.42 (m, 2H), 4.26–4.15 (m, 1H), 3.30 (dd, J=3.1, 13.2 Hz, 1H), 2.99–2.91 (m, 2H), 2.76 (dd, J=9.8, 13.5 Hz, 1H), 2.60–2.53 (m, 2H), 2.17 (s, 3H), 2.07–1.91 (m, 2H).

4(R)-Benzyl-3-[4-(2-methyl-[1,3]dioxolan-2-yl)-butyryl]-oxazolidin-2-one (2-2)

To a stirred solution of 2-1 (45 g, 156 mmol) and ethylene glycol (13.0 mL, 223 mmol) in benzene (500 mL) was added catalytic p-toluenesulfonic acid (125 mg). The resulting mixture was heated at strong reflux with azeotropic removal of water for 4 h. The mixture was cooled to ambient temperature, diluted with ethyl acetate and washed with water, saturated aqueous sodium hydrogen carbonate, saturated aqueous sodium chloride, and dried over anhydrous magnesium sulfate. The reaction mixture was filtered and concentrated at reduced pressure to give 2-2 as a yellow oil, which crystallized on standing.

$^{1}$H NMR (300 MHz, CDCl$_3$) δ 7.40–7.15 (m, 5H), 4.73–4.62 (m, 1H), 4.25–4.16 (m, 2H), 3.95 (m, 4H), 3.30 (dd, J=3.3, 13.4 Hz, 1H), 3.04–2.86 (m, 2H), 2.76 (dd, J=9.8, 13.5 Hz, 1H), 1.79–1.71 (m, 4H), 1.35 (s, 3H).

3-(6-Methoxy-pyridin-3-yl)-6-{2-oxo-3(S)-[2-(5,6,7,8-tetrahydro-[1,8]naphthyridin-2-yl)-ethyl]-pyrrolidin-1-yl}-hexanoic Acid Methyl Ester (2-3a and 2-3b)

The diastereomeric mixture of esters was prepared from 2-2 as described above for 1-15. The esters were separated via Chiral HPLC using the following conditions: Chiralpak AS 25×2 cm column, 80:20:0.2 hexane/ethanol/diethylamine, flow: 7 mL/min.

3(R or S)-(6-Methoxy-pyridin-3-yl)-6-{2-oxo-3(S)-[2-(5,6,7,8-tetrahydro-[1,8]naphthyridin-2-yl)-ethyl]-pyrrolidin-1-yl}-hexanoic Acid Methyl Ester (2-3a)

$^{1}$H NMR (300 MHz, CDCl$_3$) δ 8.00–7.93 (m, 1H), 7.43–7.38 (m, 1H), 7.05 (d, J=7.3 Hz, 1H), 6.69 (d, J=7.3 Hz, 1H), 6.39 (d, J=8.6 Hz, 1H), 4.79 (br. s, 1H), 3.95 (s, 3H), 3.59 (s, 3H), 3.49–3.35 (m, 2H), 3.27–3.01 (m, 5H), 2.73–2.50 (m, 6H), 2.49–2.30 (m, 1H), 2.28–2.11 (m, 2H), 1.95–1.22 (m, 9H).

3(S or R)-(6-Methoxy-pyridin-3-yl)-6-{2-oxo-3(S)-[2-(5,6,7,8-tetrahydro-[1,8]naphthyridin-2-yl)-ethyl]-pyrrolidin-1-yl}-hexanoic Acid Methyl Ester (2-3b)

$^{1}$H NMR (300 MHz, CDCl$_3$) d 8.00–7.93 (m, 1H), 7.43–7.38 (m, 1H), 7.05 (d, J=7.3 Hz, 1H), 6.69 (d, J=7.3 Hz, 1H), 6.39 (d, J=8.6 Hz, 1H), 4.79 (br. s, 1H), 3.95 (s, 3H), 3.59 (s, 3H), 3.49–3.35 (m, 2H), 3.27–3.01 (m, 5H), 2.73–2.50 (m, 6H), 2.49–2.30 (m, 1H), 2.28–2.11 (m, 2H), 1.95–1.22 (m, 9H).

3(R or S)-(6-Methoxy-pyridin-3-yl)-6-{2-oxo-3(S)-[2-(5,6,7,8-tetrahydro-[1,8]naphthyridin-2-yl)-ethyl]-pyrrolidin-1-yl}-hexanoic Acid (2-4a)

To a stirred solution of (2-3a) (60 mg) in tetrahydrofuran (3 mL) was added lithium hydroxide monohydrate (20 mg) in water (3 mL) and the mixture was stirred for 16 h. The reaction mixture was then concentrated at reduced pressure and resulting oil was purified by flash column chromatography (silica gel, 30:3:3 to 50:5:5% ethanol/ammonium hydroxide/water in ethyl acetate) to give 2-4a.

$^{1}$H NMR (300 MHz, CD$_3$OD) δ 8.09–7.99 (m, 1H), 7.66–7.55 (m, 1H), 6.80–6.75 (m, 1H), 6.56–6.48 (m, 1H), 3.83 (s, 3H), 3.61–3.35 (m, 4H), 3.31 (s, 3H), 3.23–1.22 (m, 20H).

3(S or R)-(6-Methoxy-pyridin-3-yl)-6-{2-oxo-3(S)-[2-(5,6,7,8-tetrahydro-[1,8]naphthyridin-2-yl)-ethyl]-pyrrolidin-1-yl}-hexanoic Acid (2-4b)

To a stirred solution of 2-3b (55 mg) in tetrahydrofuran (3 mL) was added lithium hydroxide monohydrate (20 mg) in water (3 mL) and the mixture was stirred for 16 h. The reaction mixture was then concentrated at reduced pressure and resulting oil was purified by flash column chromatography (silica gel, 30:3:3 to 50:5:5% ethanol/ammonium hydroxide/water in ethyl acetate) to give 2-4b.

$^1$H NMR (300 MHz, CD$_3$OD) δ 8.05–7.97 (m, 1H), 7.65–7.55 (m, 1H), 6.82–6.71 (m, 1H), 6.59–6.50 (m, 1H), 3.87 (s, 3H), 3.62–3.36 (m, 4H), 3.31 (s, 3H), 3.29–1.24 (m, 20H).

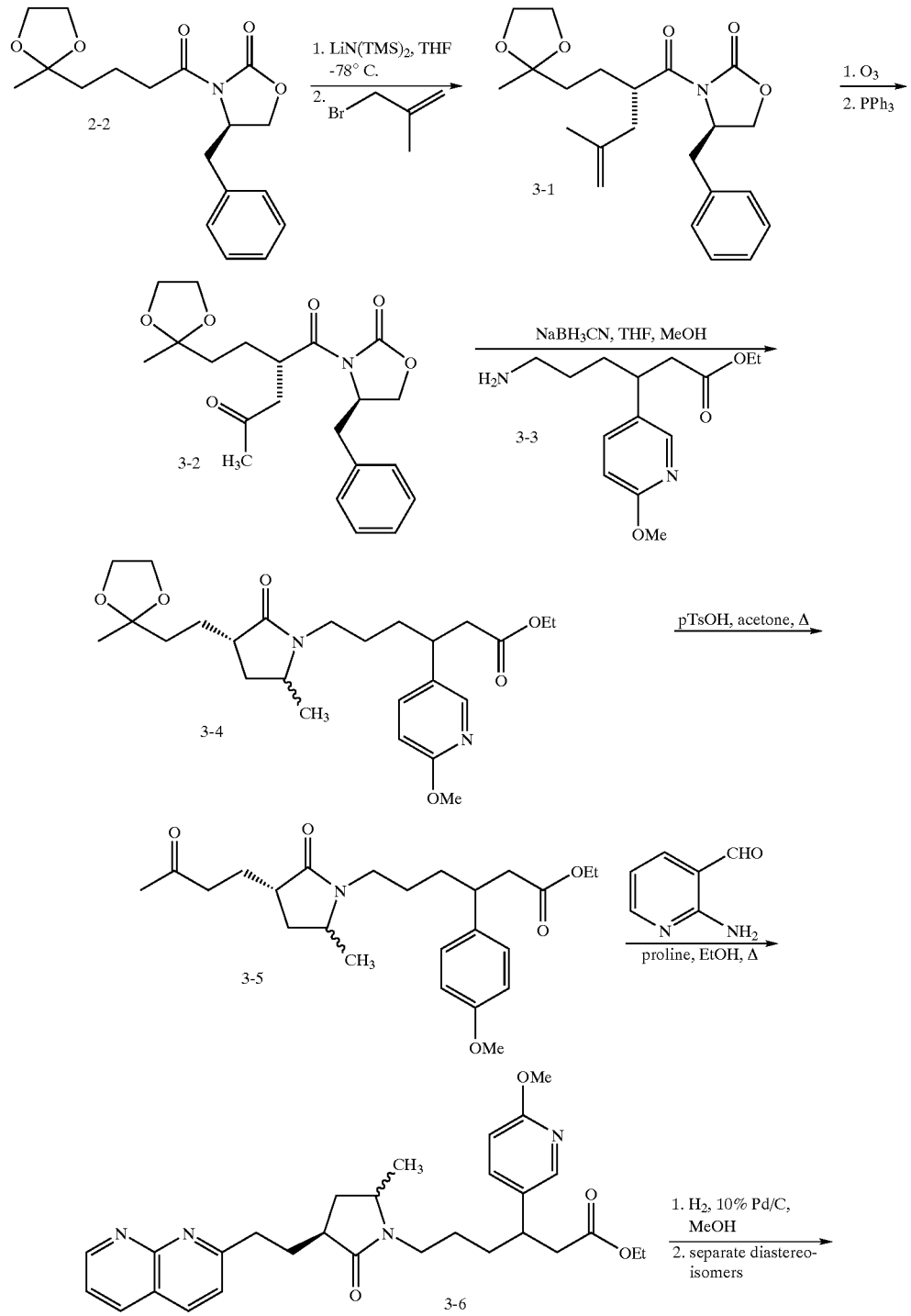

SCHEME 3

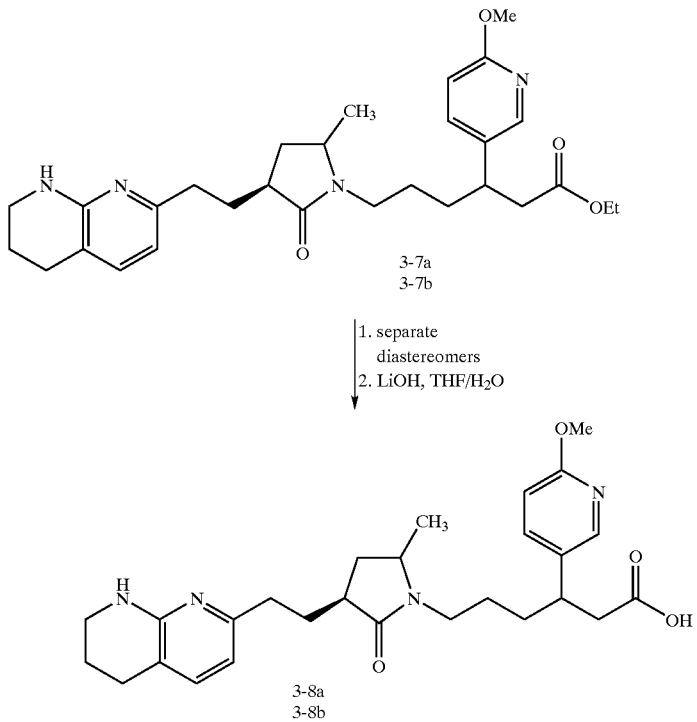

EXAMPLE 3

4(R)-Benzyl-3-{4-methyl-2(S)-[2-(2-methyl-[1,3] dioxolan-2-yl)-ethyl]-pent-4-enoyl}-oxazolidin-2-one (3-1)

To a stirred solution of 2-2 (18 g, 54 mmol) in tetrahydrofuran (400 mL) at −78° C. under argon was added a solution of lithium bis(trimethylsilylamide) (70.2 mL of a 1.0 M solution in tetrahydrofuran) over 20 min. After an additional 20 min., 3-bromo-2-methylpropene (14.6 g, 108 mmol) was added in one portion. After 20 min., the reaction mixture was allowed to warm to 0° C. After 3.5 h, the reaction mixture was diluted with ethyl acetate, washed with water, saturated aqueous sodium hydrogen carbonate, saturated aqueous sodium chloride, and dried over anhydrous magnesium sulfate. The reaction mixture was filtered and concentrated at reduced pressure. The resulting oil (3-1) was used without further purification.

1(R)-(4-Benzyl-2-oxo-oxazolidin-3-yl)-2(S)-[2-(2-methyl-[1,3]dioxolan-2-yl)-ethyl]-pentane-1,4-dione (3-2)

To a stirred solution of 3-1 (16.0 g, 42 mmol) and Sudan III dye (10 mg) in dichloromethane (500 mL) at −78° C. was bubbled ozone until the color of the dye was discharged (45 min.), after which time the solution was purged with argon for 0.5 h. Triphenylphosphine (18 g, 70 mmol) was added and the solution was allowed to warm to ambient temperature for 3 h. The reaction mixture was concentrated at reduced pressure and the resulting oil was purified by flash column chromatography (silica gel, 2 to 10% ethyl acetate/ethanol) to give 3-2 as an oil, which crystallized on standing.

$^1$H NMR (300 MHz, CDCl$_3$) δ 7.39–7.22 (m, 5H), 4.65 (m, 1H), 4.22 (m, 3H), 3.91 (m, 4H), 3.25 (dd, J=3.4, 13.8 Hz, 1H), 3.08 (dd, J=9.8, 18.3 Hz, 1H), 2.75 (dd, J=9.7, 13.5 Hz, 1H), 2.64 (dd, J=3.4, 18.0 Hz, 2H), 2.18 (s, 3H), 1.66 (m, 4H), 1.30 (s, 3H).

6-Amino-3(S or R)-(6-methoxy-pyridin-3-yl)-hexanoic Acid Ethyl ester (3-3)

Racemic 3-3 was prepared from 1-5 as described above by substituting ethanol in the final deprotection step to afford 3-3 as its HCl salt. The free base was prepared by partitioning between ethyl acetate and bicarbonate, and the first eluting isomer was isolated by preparative chiral HPLC (Chiralpak AS; 50×5 cm column, 80:10:0.1 hexane/ethanol/diethylamine; flow: 80.0 mL/min).

$^1$H NMR (300 MHz, CDCl$_3$) δ 7.39–7.22 (m, 5H), 4.65 (m, 1H), 4.22 (m, 3H), 3.91 (m, 4H), 3.25 (dd, J=3.4, 13.8 Hz, 1H), 3.08 (dd, J=9.8, 18.3 Hz, 1H), 2.75 (dd, J=9.7, 13.5 Hz, 1H), 2.64 (dd, J=3.4, 18.0 Hz, 2H), 2.18 (s, 3H), 1.66 (m, 4H), 1.30 (s, 3H).

3(R or S)-(6-Methoxy-pyridin-3-yl)-6-{5-methyl-3 (S)-[2-(2-methyl-[1,3]dioxolan-2-yl)-ethyl]-2-oxo-pyrrolidin-1-yl}-hexanoic Acid Ethyl Ester (3-4)

To a stirred suspension of 3-2 (1.55 g, 4.13 mmol) and 3-3 (1.1 g, 4.13 mmol) in THF/MeOH (25/10 mL) was added sodium cyanoborohydride (260 mg, 4.13 mmol) and the mixture was heated at 60–70° C. for 6 h. The reaction mixture was diluted with ethyl acetate, washed with saturated aqueous sodium hydrogen carbonate, saturated aqueous sodium chloride, and dried over anhydrous magnesium sulfate. The reaction mixture was filtered and concentrated at reduced pressure. The resulting oil was purified by flash column chromatography (silica gel, ethyl acetate/hexanes) to give 3-4 as a mixture of diastereomers.

$^1$H NMR (300 MHz, CDCl$_3$) δ 7.96 (d, J=2.3 Hz, 1H), 7.40 (m, 1H), 6.70 (d, J=8.5 Hz, 1H), 4.05 (q, J=7.0 Hz, 2H), 3.92 (m, 4H), 3.30–3.13 (m, 4H), 3.12–3.00 (m, 1H), 2.68–2.51 (m, 2H), 2.43–2.33 (m, 1H), 2.24–2.11 (m, 1H), 2.05–1.90 (m, 1H), 1.78–1.25 (m, 8H), 1.33 (s, 3H), 1.13 (m, 6H).

3(R or S)-(6-Methoxy-pyridin-3-yl)-6-[5-methyl-2-oxo-3-(3-oxo-butyl)-pyrrolidin-1-yl]-hexanoic Acid Ethyl Ester (3-5)

To a stirred solution of 3-4 (1.1 g) in acetone (50 mL) was added p-toluenesulfonic acid (470 mg) and the mixture was heated at reflux for 2 h, then cooled to ambient temperature. The reaction mixture was concentrated at reduced pressure and the residue was diluted with ethyl acetate, washed with saturated aqueous sodium hydrogen carbonate, saturated aqueous sodium chloride, and dried over anhydrous magnesium sulfate. The reaction mixture was filtered and concentrated at reduced pressure to give 3-5 as an oil, which was used without further purification.

$^1$H NMR (300 MHz, CDCl$_3$) δ 8.48–8.45 (m, 1H), 8.26–8.20 (m, 1H), 7.26–7.21 (m, 1H), 4.19 (s, 3H), 3.60 (s, 3H), 3.40–3.19 (m, 5H), 2.76–2.46 (m, 5H), 2.25–2.10 (m, 5H), 2.05–1.88 (m, 1H), 1.78–1.60 (m, 4H), 1.56–1.35 (m, 2H), 1.15 (m, 6H).

3(R or S)-(6-Methoxy-pyridin-3-yl)-6-{5-methyl-2-oxo-3(S)-[2-(5,6,7,8-tetrahydro-[1,8]naphthyridin-2-yl)-ethyl]-pyrrolidin-1-yl}-hexanoic Acid Ethyl Ester (3-7a, 3-7b)

A stirred solution of 2-amino-3-formylpyridine (341 mg, 2.80 mmol), 3-5 (900 mg, 2.15 mmol) and proline (322 mg, 2.80 mmol) in ethanol (20 mL) was heated at reflux for 4 h, and the cooled to ambient temperature. The reaction mixture was diluted with ethyl acetate, washed with saturated aqueous sodium hydrogen carbonate, saturated aqueous sodium chloride, and dried over anhydrous magnesium sulfate. The reaction mixture was filtered and concentrated at reduced pressure. The resulting oil was purified by flash column chromatography (silica gel, 3:0.3:0.3 to 8:0.8:0.8% ethanol/ammonium hydroxide/water in ethyl acetate) to give 3-6 as an inseparable mixture of diastereomers. To a stirred solution of the mixture of 3-6 in methanol (40 mL) was added a slurry of 10% palladium on carbon (150 mg) in ethanol (3 mL). The resulting suspension was stirred under a slight overpressure of hydrogen for 16 h. The reaction mixture was filtered through Celite and concentrated at reduced pressure. The resulting oil was purified by flash column chromatography (silica gel, 3:0.3:0.3 to 8:0.8:0.8% ethanol/ammonium hydroxide/water in ethyl acetate) to give 3-7 as a 2:1 mixture of diastereomers.

$^1$H NMR (300 MHz, CDCl$_3$) δ 8.00–7.93 (m, 1H), 7.43–7.38 (m, 1H), 7.05 (d, J=7.2 Hz, 1H), 6.64 (d, J=7.3 Hz, 1H), 6.39 (d, J=8.5 Hz, 1H), 4.76 (br. s, 1H), 4.02 (q, J=7.1 Hz, 2H), 3.95 (s, 3H), 3.49–3.35 (m, 2H), 3.27–3.01 (m, 5H), 2.73–2.50 (m, 6H), 2.49–2.30 (m, 1H), 2.28–2.11 (m, 2H), 1.95–1.25 (m, 9H), 1.18–1.03 (m, 6H). These diastereomers were separated via chiral HPLC using the following conditions: Chiralpak OD 25×4.6 cm column, 80:20:0.1 hexane/2-propanol/diethylamine flow: 1.0 mL/min. The major isomer (3-7a) eluted first, followed by the second isomer (3-7b).

3(R or S)-(6-Methoxy-pyridin-3-yl)-6-{5(R or S)-methyl-2-oxo-3(S)-[2-(5,6,7,8-tetrahydro-[1,8]naphthyridin-2-yl)-ethyl]-pyrrolidin-1-yl}-hexanoic Acid (3-8a)

To a stirred solution of 3-7a (210 mg) in tetrahydrofuran (7 mL) was added lithium hydroxide monohydrate (85 mg) in water (7 mL) and the mixture was stirred for 16 h. The reaction mixture was then concentrated at reduced pressure and resulting oil was purified by flash column chromatography (silica gel, 30:3:3 to 50:5:5% ethanol/ammonium hydroxide/water in ethyl acetate) to give 3-8a.

$^1$H NMR (300 MHz, CD$_3$OD) δ 7.99 (d, J=2.1 Hz, 1H), 7.60 (dd, J=2.4, 8.5 Hz, 1H), 7.43 (d, J=7.3 Hz, 1H), 6.78 (d, J=8.6 Hz, 1H), 6.52 (d, J=7.2 Hz, 1H), 3.87 (s, 3H), 3.61–3.35 (m, 4H), 3.31 (s, 3H), 3.23–1.25 (m, 20H), 1.21 (d, J=7.4 Hz, 3H).

3(R or S)-(6-Methoxy-pyridin-3-yl)-6-{5(S or R)-methyl-2-oxo-3(S)-[2-(5,6,7,8-tetrahydro-[1,8]naphthyridin-2-yl)-ethyl]-pyrrolidin-1-yl}-hexanoic Acid (3-8b)

To a stirred solution of 3-7b (55 mg) in tetrahydrofuran (3 mL) was added lithium hydroxide monohydrate (20 mg) in water (3 mL) and the mixture was stirred for 16 h. The reaction mixture was then concentrated at reduced pressure and resulting oil was purified by flash column chromatography (silica gel, 30:3:3 to 50:5:5% ethanol/ammonium hydroxide/water in ethyl acetate) to give 3-8b.

$^1$H NMR (300 MHz, CD$_3$OD) δ 7.98 (d, J=2.2 Hz, 1H), 7.61 (dd, J=2.4, 8.6 Hz, 1H), 7.43 (d, J=7.3 Hz, 1H), 6.78 (d, J=8.6 Hz, 1H), 6.52 (d, J=7.2 Hz, 1H), 3.87 (s,3H), 3.61–3.35 (m, 4H), 3.31 (s, 3H), 3.23–1.25 (m, 20H), 1.15 (d, J=7.3 Hz, 3H).

SCHEME 4

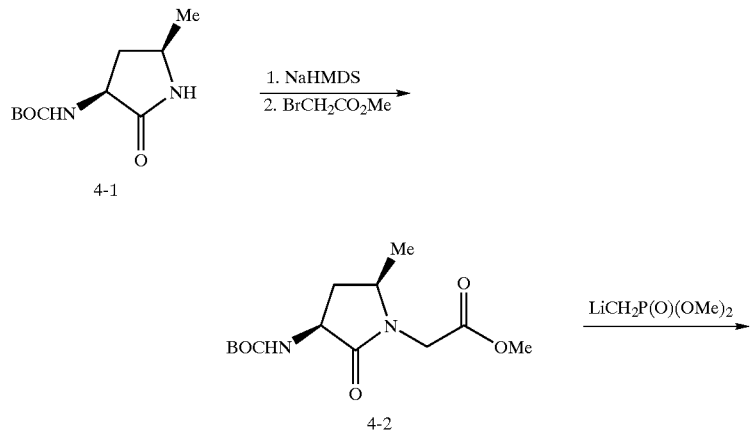

-continued
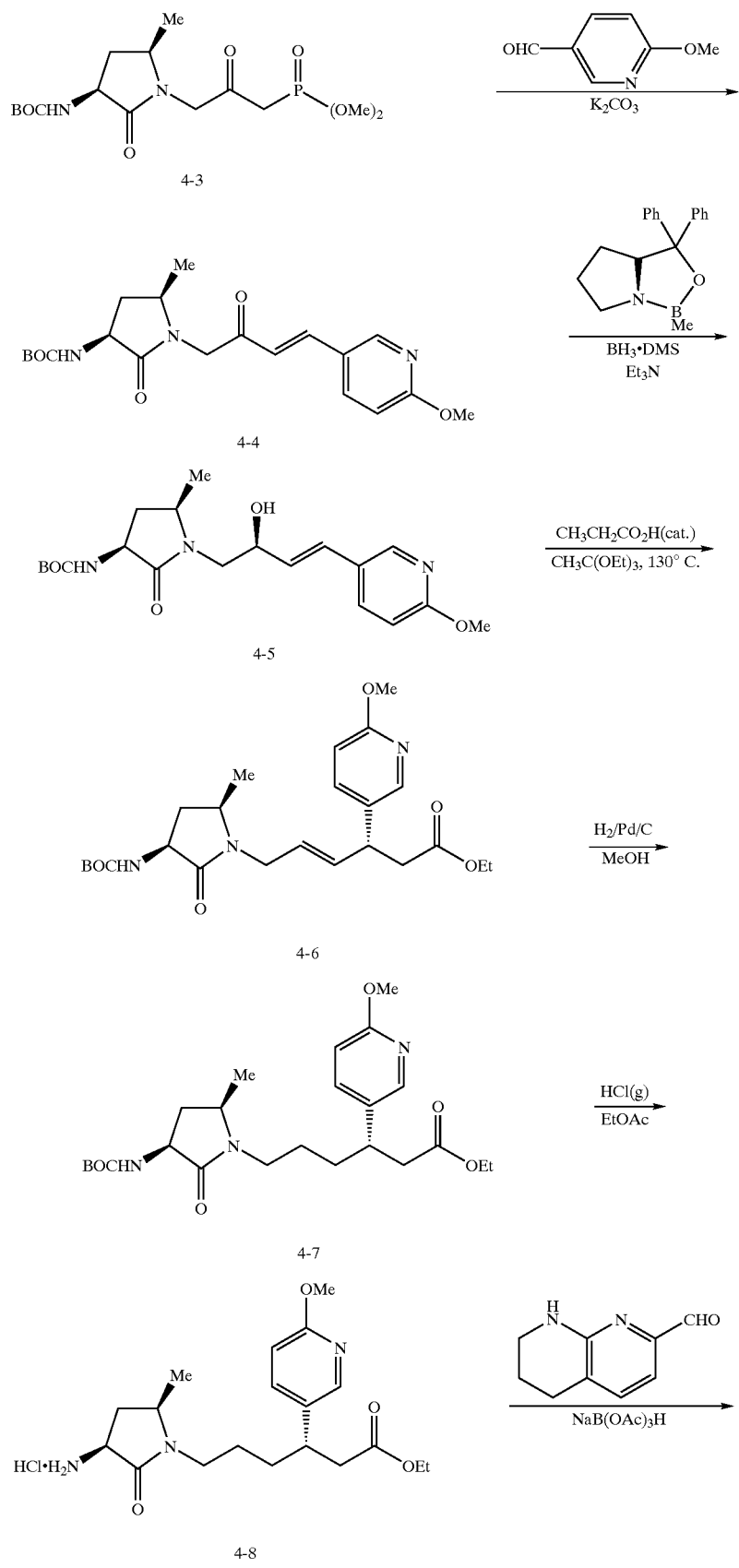

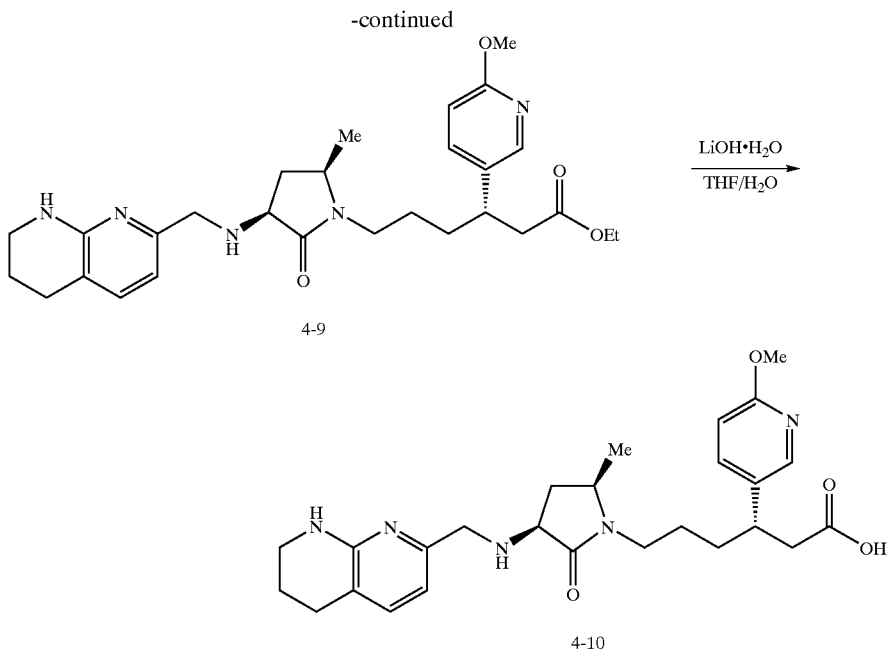

EXAMPLE 4

(3(S)-tert-Butoxycarbonylamino-5(R)-methyl-2-oxo-pyrrolidin-1-yl)-acetic Acid Methyl Ester (4-2)

To a solution of 4-1 (prepared as in WO 98/08840, published on Mar. 5, 1998, which is incorporated by reference in its entirety) (6.7 g, 31.3 mmol) in THF (90 mL) at −78° C. was added sodium bis(trimethylsilyl)amide (34.4 mL, 34.4 mmol; 1M/THF) dropwise. After 20 min, methyl bromoacetate (3.55 mL, 37.5 mmol) was added dropwise. After an additional 20 minutes, the mixture was allowed to warm to 0° C., and 50 mL saturated aqueous ammonium chloride was added. The layers were separated, the aqueous layer washed with ethyl acetate, and the combined organic extracts were dried over magnesium sulfate. Following evaporative removal of the solvent, the residue was purified by flash column chromatography (silica gel, 40% ethyl acetate/hexanes) to give 4-2 as a colorless oil.

$^1$H NMR (300 MHz, CDCl$_3$) δ 5.17 (br s, 1H), 4.38 (d, 1H, J=18 Hz), 4.22 (br s, 1H), 3.77 (m, 5H), 2.83 (m, 1H), 1.44 (s, 9H), 1.23 (m, 3H).

[3-(3 (S)-tert-Butoxycarbonylamino-5(R)-methyl-2-oxo-pyrrolidin-1-yl)-2-oxo-propyl]-phosphonic Acid Dimethyl Ester (4-3)

To a solution of methyl dimethylphosphonate (1.3 g, 10.5 mmol) in THF (25 mL) at −78° C. was added n-butyllithium (4.6 mL, 11.5 mmol; 2.5 M in hexanes) dropwise. After 10 min, 4-2 (1.0 g, 3.49 mmol) in THF (8 mL) was added dropwise. After an additional 20 minutes, saturated aqueous ammonium chloride (20 mL) was added. The THF was evaporated at reduced pressure, and the resulting mixture was extracted with ethyl acetate. The organic layer was washed with saturated aqueous sodium chloride, dried over magnesium sulfate, then filtered. Following evaporative removal of the solvent, the residue was purified by flash column chromatography (silica gel, 95:5% dichloromethane/methanol) to give 4-3 as a colorless oil.

$^1$H NMR (300 MHz, CDCl$_3$) δ 5.10 (br s, 1H), 4.49 (d, J=8.3 Hz, 1H), 4.27, 4.15 (d, J=8.3 Hz, 1H), 3.82 (d, J=1.8 Hz, 3H), 3.79 (d, J=1.8 Hz, 3H), 3.75 (m, 1H), 3.12 (m, 2H), 2.83 (m, 1H), 1.45 (s, 9H), 1.20 (d, J=6.1 Hz, 3H).

{1-[4-(6-Methoxy-pyridin-3-yl)-2-oxo-but-3-enyl]-5(R)-methyl-2-oxo-pyrrolidin-3(S)-yl}-carbamic Acid Tert-butyl Ester (4-4)

A stirred suspension of 4-3 (190 mg, 0.50 mmol), potassium carbonate (104 mg, 0.75 mmol), and 6-methoxy-pyridine-3-carboxaldehyde (for preparation, see U.S. Pat. No. 6,048,861, which is incorporated by reference herein in its entirety) (69 mg, 0.50 mmol) in N,N-dimethylformamide (2 mL) was heated at 80–85° C. for 3 hours and then cooled to ambient temperature. The reaction mixture was diluted with ethyl acetate, washed with saturated aqueous sodium hydrogen carbonate, saturated aqueous sodium chloride, dried over magnesium sulfate, and filtered. Following evaporative removal of the solvent, the residue was purified by flash column chromatography (silica gel, 95:5% ethyl acetate/methanol) to give 4-4 as a colorless oil.

$^1$H NMR (300 MHz, CDCl$_3$) δ 8.31 (d, J=2.5 Hz, 1H), 7.85 (dd, J=2.2, 8.9 Hz, 1H), 7.63 (d, J=6.2 Hz, 1H), 6.78 (d, J=8.6 Hz, 1H), 6.72 (d, J=5.8 Hz, 1H), 5.16 (br s, 1H), 4.52 (br d, J=7.6 Hz, 1H), 4.20 (m, 2H), 3.99 (s, 3H), 3.69 (m, 1H), 2.83 (m, 1H), 1.57 (m, 1H), 1.46 (s, 9H), 1.22 (d, J=6.1 Hz, 3H).

{1-[2(R)-Hydroxy-4-(6-methoxy-pyridin-3-yl)-but-3-enyl]-5(R)-methyl-2-oxo-pyrrolidin-3(S)-yl }-carbamic Acid Tert-butyl Ester (4-5)

To a stirred solution of (S)-2-methyl-CBS-oxazaborolidine (4.47 mL, 1M in toluene) in dichloromethane (10 mL) was added a solution of borane-dimethylsulfide (0.45 mL, 10M) and the resulting solution was stirred at ambient temperature for 40 minutes. This solution was added to a stirred solution of 4-4 (580 mg, 1.49 mmol) in THF (15 mL) at −40° C. and the reaction mixture was stirred for 3 hours. Methanol (2 mL) was added and the reaction mixture was concentrated at reduced pressure. The residue was purified by flash column chromatography (silica gel, 2:1 ethyl acetate/hexanes) to give 4-5 as a colorless oil.

¹H NMR (300 MHz, CDCl₃) δ 8.11 (d, J=2.4 Hz, 1H), 7.65 (dd, J=2.4, 8.5 Hz, 1H), 6.72 (d, J=8.6 Hz, 1H), 6.65 (d, J=16.2 Hz, 1H), 6.08 (dd, J=16.2, 6.3 Hz, 1H), 5.12 (br s, 1H), 4.47 (m, 1H), 4.20 (m, 2H), 3.96 (s, 3H), 3.72 (m, 1H), 3.60 (m, 1H), 3.52 (dd, J=14.5, 3.2 Hz, 1H), 3.37 (dd, J=14.3, 8.8 Hz, 1H), 2.83 (m, 1H), 1.45 (s, 9H), 1.33 (d, J=6.2 Hz, 3H).

6-(3(S)-tert-Butoxycarbonylamino-5(R)-methyl-2-oxo-pyrrolidin-1-yl)-3(R)-(6-methoxy-pyridin-3-yl)-hex-4-enoic Acid Ethyl Ester (4-6)

A stirred solution of 4-5 (400 mg) and propionic acid (5 mg) in triethylorthoacetate (5 mL) was heated at 130° C. for 2 hours, then cooled to ambient temperature, The mixture was diluted with ethyl acetate, washed with saturated aqueous sodium hydrogen carbonate, saturated aqueous sodium chloride, dried over magnesium sulfate, and filtered. Following evaporative removal of the solvent, the residue was purified by flash column chromatography (silica gel, 7:3 ethyl acetate/hexanes) to give 4-6 as a colorless oil.

¹H NMR (300 MHz, CDCl₃) δ 7.95 (d, J=2.3 Hz, 1H), 7.36 (dd, J=2.4, 8.6 Hz, 1H), 6.68 (d, J=8.6 Hz, 1H), 5.74 (m, 1H), 5.34 (m, 1H), 5.12 (br s, 1H), 4.22 (m, 1H), 4.08 (m, 1H), 4.05 (q, J=7.3 Hz, 2H), 3.89 (s, 3H), 3.81 (m, 1H), 3.53 (m, 2H), 2.70 (m, 3H), 1.42 (s, 9H), 1.17 (m, 5H).

6-(3(S)-tert-Butoxycarbonylamino-5(R)-methyl-2-oxo-pyrrolidin-1-yl)-3(S)-(6-methoxy-pyridin-3-yl)-hexanoic Acid Ethyl Ester (4-7)

To stirred solution of 4-6 (250 mg) in methanol (15 mL) was added a suspension of 10% Pd on carbon (90 mg) in ethanol (2 mL). The resulting suspension was stirred under an atmosphere of hydrogen for 1.5 hours. The mixture was filtered through Celite. The solvent was evaporated to give 4-7 as a colorless oil.

¹H NMR (300 MHz, CDCl₃) δ 7.95 (d, J=2.3 Hz, 1H), 7.36 (dd, J=2.4, 8.6 Hz, 1H), 6.68 (d, J=8.6 Hz, 1H), 5.12 (br s, 1H), 4.22 (m, 1H), 4.08 (m, 1H), 4.05 (q, J=7.3 Hz, 2H), 3.89 (s, 3H), 3.81 (m, 1H), 3.53 (m, 2H), 2.70 (m, 3H), 1.42 (s, 9H), 1.17 (m, 5H).

6-(3(S)-Amino-5(R)-methyl-2-oxo-pyrrolidin-1-yl)-3(S)-(6-methoxy-pyridin-3-yl)-hexanoic Acid Ethyl Ester Dihydrochloride (4-8)

To stirred solution of 4-7 (240 mg) in ethyl acetate (15 mL) at 0° C. was bubbled hydrogen chloride gas for 0.5 hours. The solution was warmed to ambient temperature and concentrated at reduced pressure. The resulting solid was pumped in vacuo to give the dihydrochloride salt (4-8).

¹H NMR (300 MHz, CD₃OD) δ 8.51 (dd, J=2.5, 9.2 Hz, 1H), 8.33 (d, J=2.2 Hz, 1H), 7.59 (d, J=9.1 Hz, 1H), 4.23 (s, 3H), 4.09 (m, 4H), 3.75 (m, 1H), 3.58 (m, 1H), 3.17 (m, 1H), 2.77 (m, 3H), 1.74 (m, 2H), 1.55 (m, 2H), 1.28 (d, J=6.1 Hz, 3H), 1.24 (t, J=7.2 Hz, 3H).

3(S)-(6-Methoxy-pyridin-3-yl)-6-{5(R)-methyl-2-oxo-3(S)-[(5,6,7,8-tetrahydro-[1,8]naphthyridin-2-yl-methyl)-amino]-pyrrolidin-1-yl}-hexanoic Acid Ethyl Ester (4-9)

To a stirred suspension of 4-8 (250 mg, 0.57 mmol), triethylamine (80 mL, 0.57 mmol), and 5,6,7,8-tetrahydro-[1,8]naphthyridine-2-carboxaldehyde (for preparation, see U.S. Pat. No. 6,048,861) (93 mg, 0.57 mmol) in 1,2-dichloroethane (5 mL) was added sodium triacetoxyborohydride (182 mg, 0.86 mmol) and the resulting mixture was stirred for 1.5 hours. The reaction mixture was poured into saturated aqueous sodium hydrogen carbonate and extracted with ethyl acetate. The organic layer was then washed with saturated aqueous sodium chloride, dried over magnesium sulfate, then filtered. Following evaporative removal of the solvent, the residue was purified by flash column chromatography (silica gel, 95:5:0.5:0.5% ethyl acetate/ethanol/NH₄OH/H₂O) to give 4-9 as a colorless oil.

¹H NMR (300 MHz, CDCl₃) δ 7.95 (d, J=2.3 Hz, 1H), 7.39 (dd, J=2.4, 8.6 Hz, 1H), 7.08 (d, J=7.4 Hz, 1H), 6.69 (d, J=8.6 Hz, 1H), 6.48 (d, J=7.4 Hz, 1H), 4.82 (br s, 1H), 4.03 (q, J=7.0 Hz, 2H), 3.91 (s, 3H), 3.71 (m, 2H), 3.51 (m, 1H), 3.38 (m, 4H), 3.00 (m, 2H), 2.68 (m, 2H), 2.49 (m, 4H), 1.89 (m, 2H), 1.51 (m, 6H), 1.15 (m, 5H).

3(S)-(6-Methoxy-pyridin-3-yl)-6-{5(R)-methyl-2-oxo-3(S)-[(5,6,7,8-tetrahydro-[1,8]naphthyridin-2-yl-methyl)-amino]-pyrrolidin-1-yl}-hexanoic Acid (4-10)

To a stirred solution of 4-9 (150 mg) in tetrahydrofuran (6 mL) was added lithium hydroxide monohydrate (60 mg) in water (6 mL) and the mixture was stirred for 16 h. The reaction mixture was then concentrated at reduced pressure and the resulting oil was purified by flash column chromatography (silica gel, 30:3:3 to 50:5:5% ethanol/ammonium hydroxide/water in ethyl acetate) to give 4-10 as a white solid.

¹H NMR (300 MHz, CD₃OD) δ 7.97 (d, J=2.1 Hz, 1H), 7.39 (dd, J=2.3, 8.5 Hz, 1H), 7.33 (d, J=6.3 Hz, 1H), 6.75 (d, J=8.3 Hz, 1H), 6.56 (d, J=7.0 Hz, 1H), 3.95 (m, 5H), 3.48 (m, 5H), 3.11 (m, 2H), 2.78 (m, 2H), 2.50 (m, 3H), 1.95 (m, 3H), 1.78 (m, 1H), 1.59 (m, 1H), 1.39 (m, 2H), 1.21 (d, J=6.4 Hz, 3H).

SCHEME 5

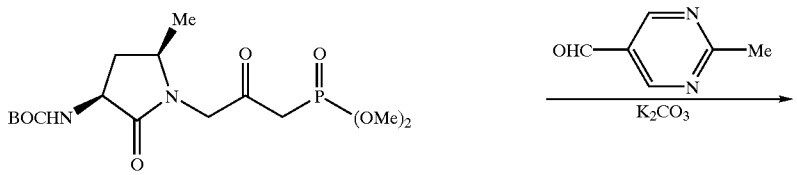

4-3

-continued
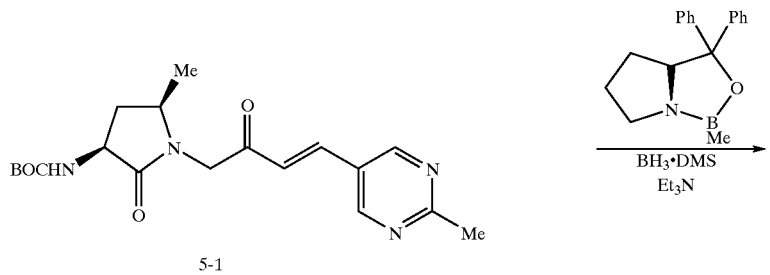
5-1
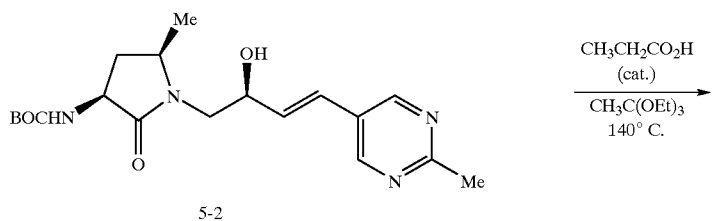
5-2
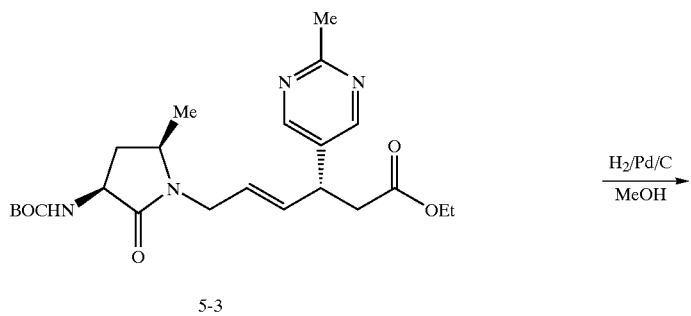
5-3
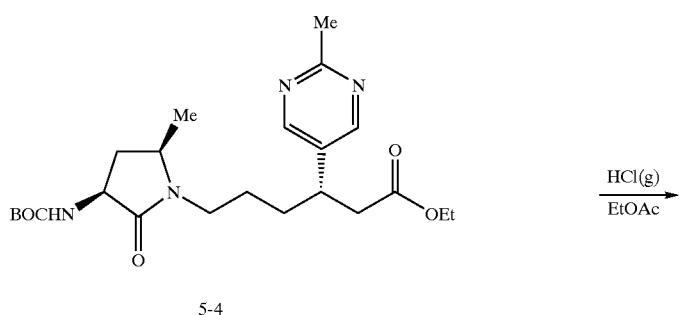
5-4
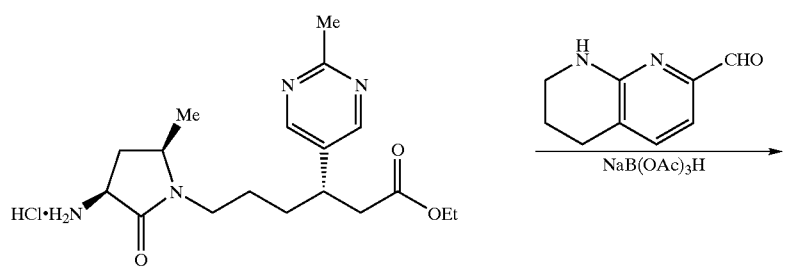
5-5

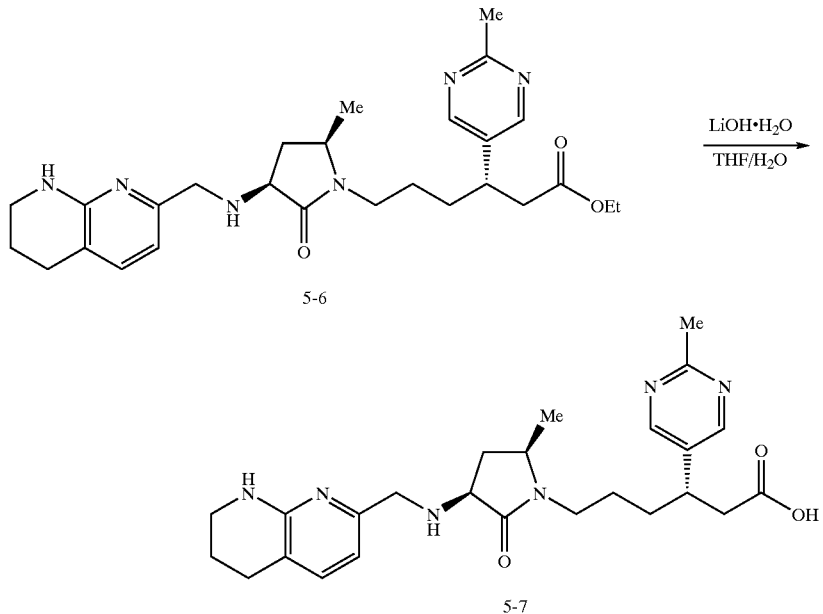

EXAMPLE 5

{1-[4-(2-methyl-pyrimidin-5-yl)-2-oxo-but-3-enyl]-5(R)-methyl-2-oxo-pyrrolidin-3(S)-yl}-carbamic Acid Tert-butyl Ester (5-1)

A stirred suspension of 4-3 (2.5 g, 6.61 mmol), potassium carbonate (1.83 g, 13.2 mmol), and 2-methyl-pyrimidine-5-carboxaldehyde (for preparation, see U.S. Pat. No. 6,048,861) (0.81 g, 6.61 mmol) in THF (50 mL) was heated at 60–65° C. for 3 hours and then cooled to ambient temperature. The reaction mixture was diluted with ethyl acetate, washed with saturated aqueous sodium hydrogen carbonate, saturated aqueous sodium chloride, dried over magnesium sulfate, and filtered. Following evaporative removal of the solvent, the residue was purified by flash column chromatography (silica gel, 95:5% ethyl acetate/methanol) to give 5-1 as a white foam.

$^1$H NMR (300 MHz, CDCl$_3$) δ 8.83 (s, 2H), 7.59 (d, J=8.1 Hz, 1H), 6.92 (d, J=7.4 Hz, 1H), 5.16 (br s, 1H), 4.53 (br d, J=7.6 Hz, 1H), 4.20 (m, 2H), 3.78 (m, 2H), 2.80 (m, 1H), 2.78 (s, 3H), 1.57 (m, 1H), 1.46 (s, 9H), 1.22 (d, J=6.1 Hz, 3H).

{1-[2-Hydroxy-4-(2-methyl-pyrimidin-5-yl)-but-3-enyl]-5(R)-methyl-2-oxo-pyrrolidin-3(S)-yl}-carbamic Acid Tert-butyl Ester (5-2)

To a stirred solution of (S)-2-methyl-CBS-oxazaborolidine (6.4 mL, 1M in toluene) in dichloromethane (15 mL) was added a solution of borane-dimethylsulfide (0.64 mL, 10M) and the resulting solution was stirred at ambient temperature for 40 minutes. This solution was added to a stirred solution of 5-1 (800 mg, 2.14 mmol) in THF (30 mL) at −40° C. and the reaction mixture was stirred for 3 hours. Methanol (5 mL) was added and the reaction mixture was concentrated at reduced pressure. The residue was purified by flash column chromatography (silica gel, 9:1 ethyl acetate/methanol) to give 5-2 as a colorless oil.

$^1$H NMR (300 MHz, CDCl$_3$) δ 8.63 (s, 2H), 6.68 (d, J=16 Hz, 1H), 6.30 (dd, J=16.1, 6.2 Hz, 1H), 5.12 (br s, 1H), 4.47 (m, 1H), 4.20 (m, 2H), 3.70 (m, 2H), 3.48 (dd, J=14.4, 3.3 Hz, 1H), 3.40 (dd, J=14.3, 8.6 Hz, 1H), 2.82 (m, 1H), 1.45 (s, 9H), 1.34 (d, J=6.1 Hz, 3H).

6-(3(S)-tert-Butoxycarbonylamino-5(R)-methyl-2-oxo-pyrrolidin-1-yl)-3(R)-(2-methyl-pyrimidin-5-yl)-hex-4-enoic Acid Ethyl Ester (5-3)

A stirred solution of 5-2 (300 mg) and propionic acid (5 mg) in triethylorthoacetate (6 mL) was heated at 140° C. for 3 hours, then cooled to ambient temperature. The mixture was diluted with ethyl acetate, washed with saturated aqueous sodium hydrogen carbonate, saturated aqueous sodium chloride, dried over magnesium sulfate, and filtered. Following evaporative removal of the solvent, the residue was purified by flash column chromatography (silica gel, 9:1 ethyl acetate/methanol) to give 5-3 as a tan foam.

$^1$H NMR (300 MHz, CDCl$_3$) δ 8.48 (s, 2H), 5.76 (m, 1H), 5.42 (m, 1H), 5.09 (br s, 1H), 4.21 (m, 1H), 4.08 (m, 1H), 4.07 (q, J=7.3 Hz, 2H), 3.59 (m, 2H), 2.72 (m, 3H), 2.70 (s, 3H), 1.42 (s, 9H), 1.19 (m, 5H).

6-(3(S)-tert-Butoxycarbonylamino-5(R)-methyl-2-oxo-pyrrolidin-1-yl)-3(S)-(2-methyl-pyrimidin-5-yl)-hexanoic Acid Ethyl Ester (5-4)

To stirred solution of 5-3 (180 mg) in methanol (8 mL) was added a suspension of 10% Pd on carbon (60 mg) in ethanol (1 mL). The resulting suspension was stirred under an atmosphere of hydrogen for 1.5 hours. The mixture was filtered through Celite. The solvent was evaporated to give 5-4 as an oil.

$^1$H NMR (300 MHz, CDCl$_3$) δ 8.48 (s, 2H), 5.10 (br s, 1H), 4.15 (m, 1H), 4.05 (q, J=7.4 Hz, 2H), 3.51 (m, 2H), 3.06 (m, 2H), 2.72 (s, 3H), 2.61 (m, 2H), 1.42 (s,9H), 1.17 (m, 5H).

6-(3(S)-Amino-5(R)-methyl-2-oxo-pyrrolidin-1-yl)-3(S)-(2-methyl-pyrimidin-5-yl)-hexanoic Acid Ethyl Ester Dihydrochloride (5-5)

To stirred solution of 5-4 (180 mg) in ethyl acetate (15 mL) at 0° C. was bubbled hydrogen chloride gas for 0.5 hours. The solution was warmed to ambient temperature and concentrated at reduced pressure. The resulting solid was pumped in vacuo to give the dihydrochloride salt (5-5).

$^1$H NMR (300 MHz, CD$_3$OD) δ 8.88 (s, 2H), 4.09 (m, 4H), 3.75 (m, 1H), 3.58 (m, 1H), 3.17 (m, 1H), 2.81 (s, 3H), 2.77 (m, 3H), 1.74 (m, 2H), 1.55 (m, 2H), 1.26 (d, J=6.2 Hz, 3H), 1.21 (t, J=7.2 Hz, 3H).

3(S)-(2-Methyl-pyrimidin-5-yl)-6-{5(R)-methyl-2-oxo-3(S)-[(5,6,7,8-tetrahydro-[1,8]naphthyridin-2-yl-methyl)-amino]-pyrrolidin-1-yl}-hexanoic Acid Ethyl Ester (5-6)

To a stirred suspension of 5-5 (170 mg, 0.44 mmol), triethylamine (61 mL, 0.44 mmol), and 5,6,7,8-tetrahydro-[1,8]naphthyridine-2-carbaldehyde (72 mg, 0.44 mmol) in 1,2-dichloroethane (4 mL) was added sodium triacetoxyborohydride (112 mg, 0.53 mmol) and the resulting mixture was stirred for 1.5 hours. The reaction mixture poured into saturated aqueous sodium hydrogen carbonate and extracted with ethyl acetate. The organic layer was then washed with saturated aqueous sodium chloride, dried over magnesium sulfate, and filtered. Following evaporative removal of the solvent, the residue was purified by flash column chromatography (silica gel, 95:5:0.5:0.5% ethyl acetate/ethanol/NH$_4$OH/H$_2$O) to give 5-6 as a colorless oil.

$^1$H NMR (300 MHz, CDCl$_3$) δ 8.47 (s, 2H), 7.08 (d, J=7.3 Hz, 1H), 6.48 (d, J=7.0 Hz, 1H), 4.85 (br s, 1H), 4.03 (q, J=7.0 Hz, 2H), 3.71 (m, 2H), 3.42 (m, 4H), 2.71 (s, 3H), 2.51 (m, 4H), 1.89 (m, 2H), 1.43 (m, 6H), 1.16 (m, 5H).

3(S)-(2-Methyl-pyrimidin-5-yl)-6-{5(R)-methyl-2-oxo-3(S)-[(5,6,7,8-tetrahydro-[1,8]naphthyridin-2-yl-methyl)-amino]-pyrrolidin-1-yl}-hexanoic Acid (5-7)

To a stirred solution of 5-6 (110 mg) in tetrahydrofuran (4.5 mL) was added lithium hydroxide monohydrate (45 mg) in water (4.5 mL) and the mixture was stirred for 16 h. The reaction mixture was concentrated at reduced pressure and the resulting oil was purified by flash column chromatography (silica gel, 30:3:3 to 50:5:5% ethanol/ammonium hydroxide/water in ethyl acetate) to give 5-7 as a white solid.

1H NMR (300 MHz, CD$_3$OD) δ 8.60 (s, 2H), 7.32 (d, J=7.3 Hz, 1H), 6.56 (d, J=5.2 Hz, 1H), 3.94 (m, 2H), 3.50 (m, 5H), 3.16 (m, 2H), 2.78 (m, 2H), 2.62 (s, 3H), 2.56 (m, 3H), 1.95 (m, 2H), 1.70 (m, 2H), 1.40 (m, 2H), 1.23 (d, J=7.1 Hz, 3H).

EXAMPLE 6

3(R or S)-(2-Methoxy-pyrimidin-5-yl)-6-{2-oxo-3(S)-[2-(5,6,7,8-tetrahydro-[1,8]naphthyridin-2-yl)-ethyl]-pyrrolidin-1-yl}hexanoic Acid The title compound was prepared in a similar manner as Example 2 depicted in Scheme 2 but using 6-amino-3-(2-methoxy-pyrimidin-5-yl)-hexanoic acid methyl ester dihydrochloride in place of 6-amino-3-(6-methoxy-pyridin-3-yl)-hexanoic acid methyl ester dihydrochloride (1-6).

EXAMPLE 7

3(S or R)-(2-Methoxy-pyrimidin-5-yl)-6-{5(S or R)-methyl-2-oxo-3(S)-[(5,6,7,8-tetrahydro-[1,8]naphthyridin-2-yl)-ethyl]-pyrrolidin-1-yl}hexanoic Acid and 3(S or R)-(2-Methoxy-pyrimidin-5-yl)-6-{5(R or S)-methyl-2-oxo-3(S)-[(5,6,7,8-tetrahydro-[1,8]naphthyridin-2-yl)-ethyl]-pyrrolidin-1-yl}hexanoic Acid The title compounds were prepared in a similar manner as Example 3 depicted in Scheme 3 but using 6-amino-3(S or R)-(2-methoxy-pyrimidin-5-yl)-hexanoic acid ethyl ester in place of 6-amino-3-(6-methoxy-pyridin-3-yl)-hexanoic acid ethyl ester (3-3).

SCHEME A
Synthesis of Radioligand for SPAV3 Assay

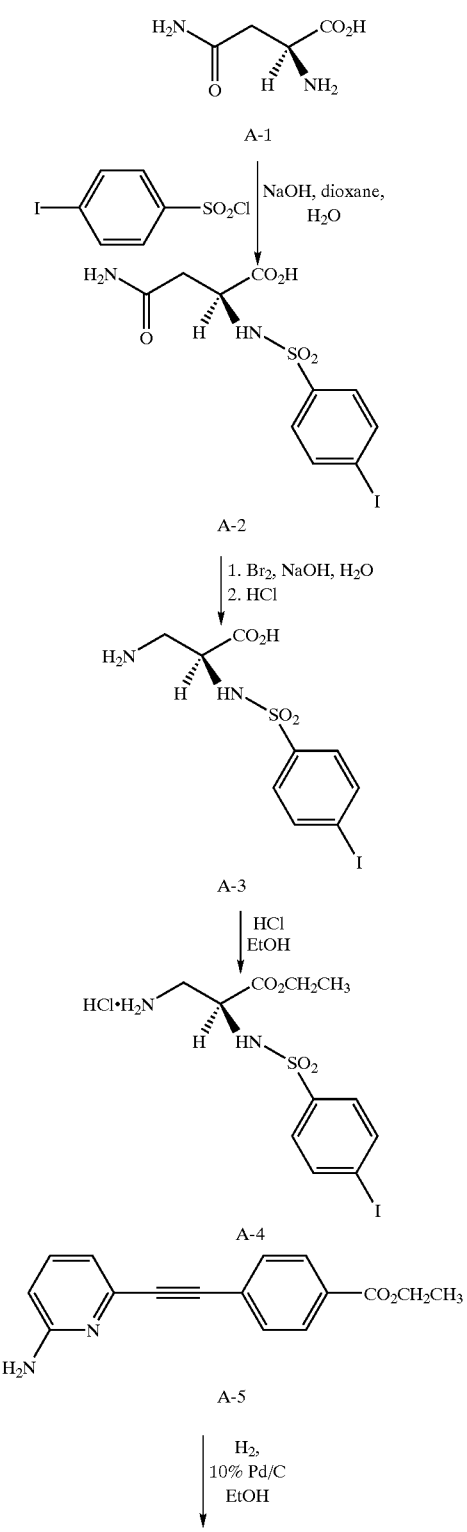

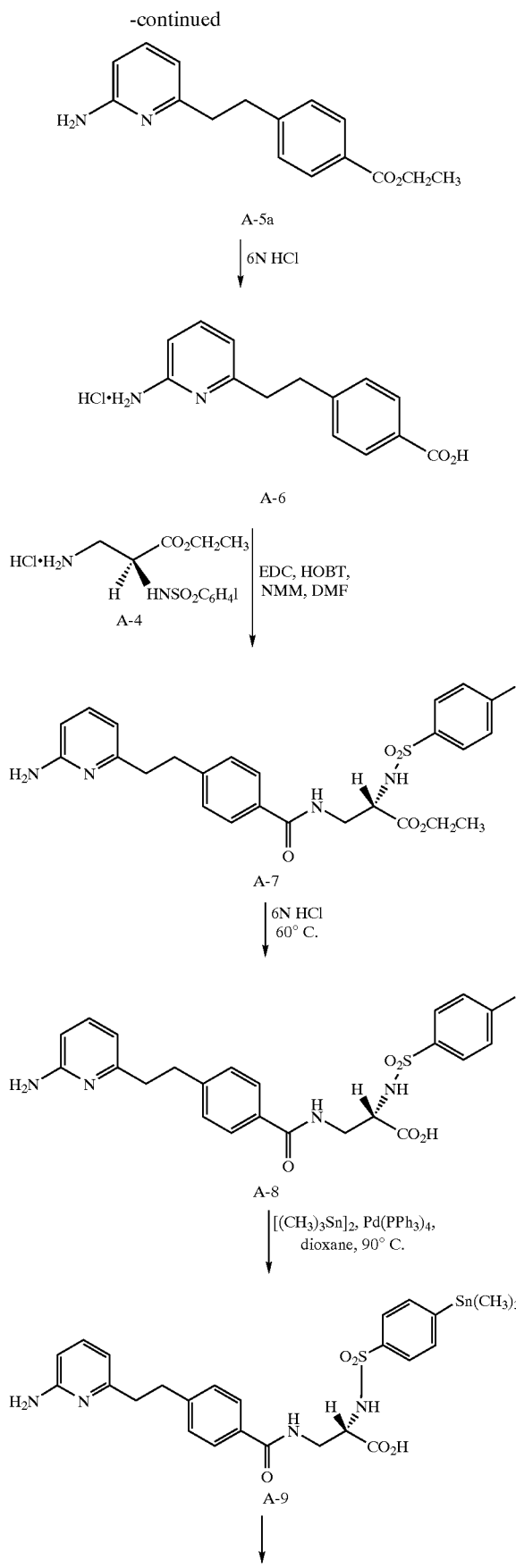

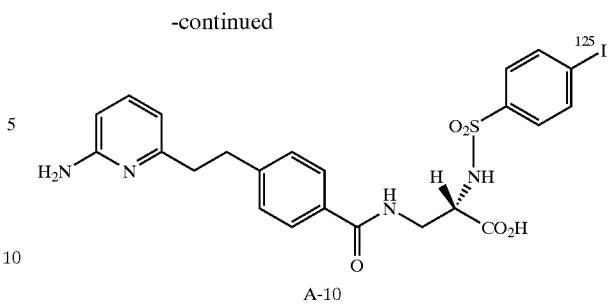

N-(4-Iodo-phenylsulfonylamino)-L-asparagine (A-2)

To a stirred solution of acid A-1 (4.39 g, 33.2 mmol), NaOH (1.49 g, 37.2 mmol), dioxane (30 ml) and H$_2$O (30 ml) at 0° C. was added pipsyl chloride (10.34 g, 34.2 mmol). After 5 minutes, NaOH (1.49, 37.2 mmol) dissolved in 15 ml H$_2$O), was added followed by the removal of the cooling bath. After 2.0 h, the reaction mixture was concentrated. The residue was dissolved in H$_2$O (300 ml) and then washed with EtOAc. The aqueous portion was cooled to 0° C. and then acidified with concentrated HCl. The solid was collected and then washed with Et$_2$O to provide acid A-2 as a white solid.

$^1$H NMR (300 MHz, D$_2$O) δ 7.86 (d, 2H, J=8 Hz), 7.48 (d, 2H, J=8 Hz) 3.70 (m, 1H), 2.39 (m, 2H).

2(S)-(4-Iodo-phenylsulfonylamino)-β-alanine (A-3)

To a stirred solution of NaOH (7.14 g, 181.8 mmol) and H$_2$O (40 ml) at 0° C. was added Br$_2$ (1.30 ml, 24.9 mmol) dropwise over a ten minute period. After ~5 minutes, acid A-2 (9.9 g, 24.9 mmol), NaOH (2.00 g, 49.8 mmol) and H$_2$O (35 ml) were combined, cooled to 0° C. and then added in a single portion to the reaction. After stirring for 20 minutes at 0° C., the reaction was heated to 90° C. for 30 minutes and then recooled to 0° C. The pH was adjusted to ~7 by dropwise addition of concentrated HCl. The solid was collected, washed with EtOAc, and then dried in vacuo to provide acid A-3 as a white solid.

$^1$H NMR (300 MHz, D$_2$O) δ 8.02 (d, 2H, J=8 Hz), 7.63 (d, 2H, J=8 Hz), 4.36 (m, 1H), 3.51 (dd, 1H, J=5 Hz, 13 Hz) 3.21 (m, 1H).

Ethyl 2(S)-(4-iodo-phenylsulfonylamino)-β-alanine-hydrochloride (A-4)

HCl gas was rapidly bubbled through a suspension of acid A-3 (4.0 g, 10.81 mmol) in EtOH (50 ml) at 0° C. for 10 minutes. The cooling bath was removed and the reaction was heated to 60° C. After 18 h, the reaction was concentrated to provide ester A-4 as a white solid.

$^1$H NMR (300 MHz, CD$_3$OD) δ 7.98 (d, 2H, J=8 Hz), 7.63 (d, 2H, J=8 Hz), 4.25 (q, 1H, J=5 Hz), 3.92 (m, 2H), 3.33 (m, 1H), 3.06 (m, 1H), 1.01 (t, 3H, J=7 Hz).

Ethyl 4-[2-(2-Aminopyridin-6-yl)ethyl]benzoate (A-5a)

A mixture of ester A-5 (700 mg, 2.63 mmol), (for preparation, see: Scheme 29 (intermediate 29-3) of U.S. Pat. No. 5,741,796 (Apr. 21, 1998)), 10% Pd/C (350 mg) and EtOH were stirred under 1 atm H$_2$. After 20 h, the reaction was filtered through a celite pad and then concentrated to provide ester A-5a as a brown oil.

TLC R$_f$=0.23 (silica, 40% EtOAc/hexanes); $^1$H NMR (300 MHz, CDCl$_3$) δ 7.95 (d, 2H, J=8 Hz), 7.26 (m, 3H), 6.43 (d, 1H, J=7 Hz), 6.35 (d, 1H, J=8 Hz), 4.37 (m, 4H), 3.05 (m, 2H), 2.91 (m, 2H), 1.39 (t, 3H, J=7 Hz).

4-[2-(2-Aminopyridin-6-yl)ethyl]benzoic Acid Hydrochloride (A-6)

A suspension of ester A-5a (625 mg, 2.31 mmol) in 6N HCl (12 ml) was heated to 60° C. After ~20 h, the reaction was concentrated to give acid A-6 as a tan solid.

$^1$H NMR (300 MHz, CD$_3$OD) δ 7.96 (d, 2H, J=8 Hz), 7.80 (m, 1H), 7.33 (d, 2H, J=8 Hz), 6.84 (d, 1H, J=9 Hz), 6.69 (d, 1H, J=7 Hz), 3.09 (m, 4H).

Ethyl 4-[2-(2-Aminopyridin-6-yl)ethyl]benzoyl-2(S)-(4-iodo-phenylsulfonylamino)-β-alanine (A-7)

A solution of acid 15-6 (400 mg, 1.43 mmol), amine A-4 (686 mg, 1.57 mmol), EDC (358 mg, 1.86 mmol), HOBT (252 mg, 1.86 mmol), NMM (632 μl, 5.72 mmol) in DMF (10 ml) was stirred for ~20 h. The reaction was diluted with EtOAc and then washed with sat. NaHCO$_3$, brine, dried (MgSO$_4$) and concentrated. Flash chromatography (silica, EtOAc then 5% isopropanol/EtOAc) provided amide A-7 as a white solid.

TLC R$_f$=0.4 (silica, 10% isopropanol/EtOAc); $^1$H NMR (300 MHz, CD3OD) δ 7.79 (d, 2H, J=9 Hz) 7.61 (d, 2H, J=8Hz), 7.52 (d, 2H, J=9 Hz), 7.29 (m, 1H), 7.27 (d, 2H, J=8 Hz), 4.20 (m, 1H), 3.95 (q, 2H, J=7 Hz), 3.66 (dd, 1H, J=6 Hz, 14 Hz), 3.49 (dd, 1H, J=8 Hz, 13 Hz), 3.01 (m, 2H), 2.86 (m, 2H), 1.08 (t, 3H, J=7 Hz).

4-[2-(2-Aminopyridin-6-yl)ethyl]benzoyl-2(S)-(4-iodophenyl-sulfonylamino)-β-alanine (A-8)

A solution of ester A-7 (200 mg, 0.3213 mmol) and 6N HCl (30 ml) was heated to 60° C. After ~20 h, the reaction mixture was concentrated. Flash chromatography (silica, 20:20:1:1 EtOAc/EtOH/ NH$_4$OH/H$_2$O) provided acid A-8 as a white solid.

TLC R$_f$=0.45 (silica, 20:20:1:1 EtOAc/EtOH/NH$_4$OH/ H$_2$O); $^1$H NMR (400 MHz, DMSO-d6) δ 8.40 (m, 1H), 8.14 (Bs, 1H), 7.81 (d, 2H, J=8 Hz), 7.62 (d, 2H, J=8 Hz), 7.48 (d, 2H, J=8 Hz), 7.27 (m, 3H), 6.34 (d, 1H, J=7 Hz), 6.25 (d, 1H, J=8 Hz), 5.85 (bs, 2H), 3.89 (bs, 1H), 3.35 (m, 2H), 2.97 (m, 2H), 2.79 (m, 2H).

4-[2-(2-Aminopyridin-6-yl)ethyl)benzoyl-2(S)-(4-trimethylstannyl-phenylsulfonylamino-β-alanine (A-9)

A solution of iodide A-8 (70 mg, 0.1178 mmol), [(CH$_3$)$_3$Sn]$_2$ (49 μl, 0.2356 mmol), Pd(PPh$_3$)$_4$ (5 mg) and dioxane (7 ml) was heated to 90° C. After 2 h, the reaction was concentrated and then purified by preparative HPLC (Delta-Pak C$_{18}$ 15 μM 100A°, 40×100 mm; 95:5 then 5:95 H$_2$O/CH$_3$CN) to provide the trifluoroacetate salt. The salt was suspended in H$_2$O (10 ml), treated with NH$_4$OH (5 drops) and then lyophilized to provide amide A-9 as a white solid.

$^1$H NMR (400 MHz, DMSO-d6) δ 8.40 (m, 1H), 8.18 (d, 1H, J=8 Hz), 7.67 (m, 5H), 7.56 (d, 2H, J=8 Hz), 7.29 (d, 2H, J=8 Hz), 6.95–7.52 (m, 2H), 6.45 (bs, 2H), 4.00 (m, 1H), 3.50 (m, 1H), 3.33 (m, 1H), 2.97 (m, 2H), 2.86 (m, 2H).

4-[2-(2-Aminopyridin-6-yl)ethyl]benzoyl-2(S)-4-$^{125}$iodo-phenylsulfonylamino-β-alanine (A-10)

An iodobead (Pierce) was added to a shipping vial of 5 mCi of Na$^{125}$I (Amersham, IMS30) and stirred for five minutes at room temperature. A solution of 0.1 mg of A-9 in 0.05 mL of 10% H$_2$SO$_4$/MeOH was made and immediately added to the Na$^{125}$I/iodobead vial. After stirring for three minutes at room temperature, approximately 0.04–0.05 mL of NH$_4$OH was added so the reaction mixture was at pH 6–7. The entire reaction mixture was injected onto the HPLC for purification [Vydac peptide-protein C-18 column, 4.6×250 mm, linear gradient of 10% acetonitrile (0.1% (TFA):H$_2$O (0.1% TFA) to 90% acetonitrile (0.1% TFA):H$_2$O (0.1% TFA) over 30 minutes, 1 mL/min]. The retention time of A-10 is 17 minutes under these conditions. Fractions containing the majority of the radioactivity were pooled, lyophilized and diluted with ethanol to give approximately 1 mCi of A-10, which coeluted on HPLC analysis with an authentic sample of A-8.

SCHEME B
Synthesis of Radioligand for SPAV5 Assay

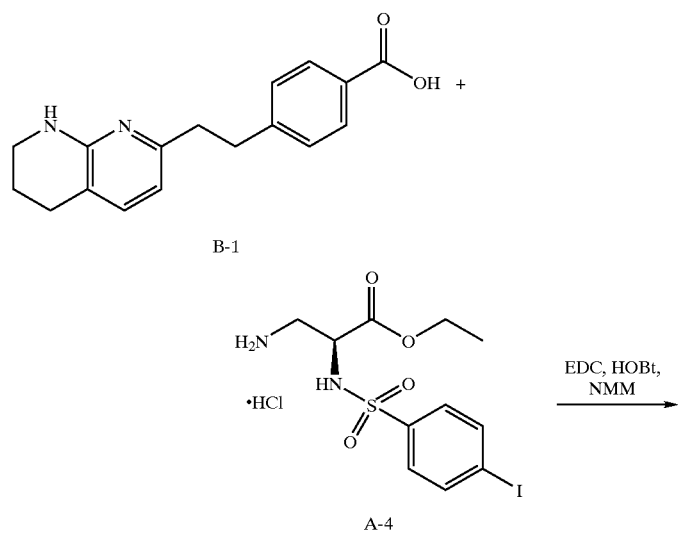

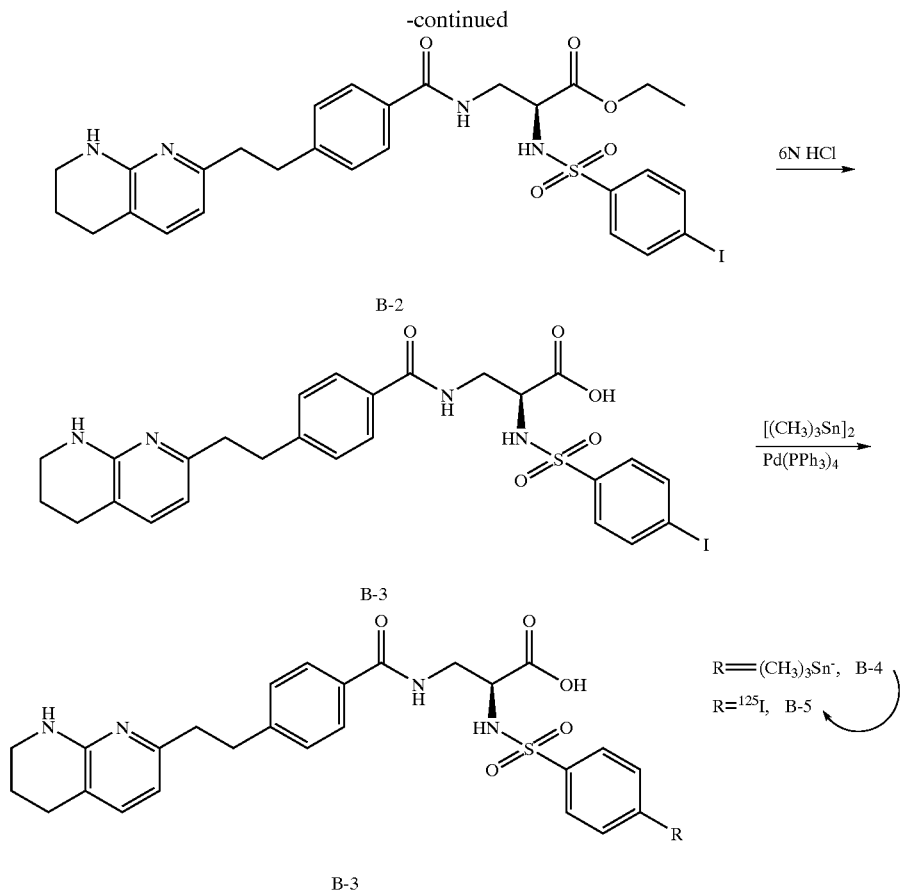

B-2

B-3

B-3

2(S)-(4-Iodo-benzenesulfonylamino)-3-{4-[2-(5,6,7,8-tetrahydro-[1,8]naphthyridin-2-yl)-ethyl]-benzoylamino}-propionic Acid Ethyl Ester (B-2)

A mixture of B-1 (0.23 g, 0.72 mmol; for preparation see U.S. Pat. No. 5,741,796), A-4 (0.343 g, 0.792 mmol), EDC (0.179 g, 0.93 mmol), HOBT (0.126 g, 0.93 mmol), NMM (0.316 mL, 2.86 mmol) in acetonitrile (3 mL) and DMF (3 mL) was stirred for 2 hours at ambient temperature then diluted with ethyl acetate, washed with water, saturated aqueous $NaHCO_3$, and brine, dried over $MgSO_4$, and concentrated. The residue was chromatographed on silica gel (70:25:5 $CHCl_3$/EtOAc/MeOH) to give B-2 as a white solid.

TLC $R_f$=0.22 (silica, 70:25:5 $CHCl_3$/EtOAc/MeOH). $^1$H NMR (300 MHz, $CDCl_3$) δ 7.79 (d, 2H, J=8 Hz), 7.63 (d, 2H, J=8 Hz), 7.54 (d, 2H, J=8 Hz), 7.27 (d, 2H, J=8 Hz),7.04 (d, 1H, J=7 Hz), 6.60 (m, 1H), 6.29 (d, 1H, J=7 Hz), 4.83 (br s, 1H), 4.09 (m, 3H), 3.84 (m, 1H), 3.68 (m, 1H), 3.42 (m, 2H), 3.01 (m, 4H), 2.86 (m, 4H), 2.69 (t, 2H, J=6 Hz), 1.88 (m, 2H).

2(S)-(4-Iodo-benzenesulfonylamino)-3-{4-[2-(5,6,7,8-tetrahydro-[1,8]naphthyridin-2-yl)-ethyl]-benzoylamino}-propionic Acid (B-3)

A mixture of B-2 (0.38 g, 0.573 mmol) and 6N HCl (50 mL) was stirred for 14 hours at 60° C. After cooling to room temperature, the mixture was concentrated, and the residue chromatographed on silica gel (25:10:1:1 to 15:10:1:1 EtOAc/EtOH/$NH_4OH$/$H_2O$) to give B-3 as a white solid.

TLC $R_f$=0.43 (silica, 10:10:1:1 EtOAc/EtOH/$NH_4OH$/$H_2O$). $^1$H NMR (300 MHz, DMSO-$d_6$) δ 8.42 (m, 1H), 7.79 (d, 2H, J=8 Hz), 7.63 (d, 2H, J=8 Hz), 7.44 (d, 2H, J=8 Hz), 7.27 (d, 2H, J=8 Hz),7.10 (d, 1H, J=7 Hz), 6.58 (br s, 1H), 6.32 (d, 1H, J=7 Hz), 3.96 (m, 1H), 3.51 (m, 1H), 3.30 (m, 5H), 2.96 (m, 2H), 2.78 (m, 2H), 2.62 (m, 2H), 1.77 (m, 2H). HRMS: For $C_{26}H_{27}IN_4O_5S$, expected 635.0818, found 635.0831.

3-{4-[2-(5,6,7,8-Tetrahydro-[1,8]naphthyridin-2-yl)-ethyl]-benzoylamino}-2(S)-(4-trimethylstannanyl-benzenesulfonylamino)-propionic Acid (B-4)

A mixture of B-3 (0.10 g, 0.16 mmol), hexamethyldistannane (0.065 mL, 0.32 mmol), $Pd(PPh_3)_4$, and dioxane (10 mL) was stirred for one hour at 90° C. After cooling to room temperature, the mixture was concentrated, and the residue chromatographed on silica gel (50:10:1:1 to 25:10:1:1 EtOAc/EtOH/$NH_4OH$/$H_2O$) to give B-4 as a white solid.

TLC $R_f$=0.48 (silica, 15:10:1:1 EtOAc/EtOH/$NH_4OH$/$H_2O$). $^1$H NMR (300 MHz, DMSO-$d_6$) δ 8.38 (m, 1H), 8.14 (m, 1H), 7.63 (m, 4H), 7.28 (d, 2H, J=8 Hz), 7.08 (d, 1H, J=7 Hz), 6.50 (br 3, 1H), 6.28 (d, 1H, J=7 Hz), 3.96 (m, 1H), 3.48 (m, 1H), 3.31 (m, 5H), 2.96 (m, 2H), 2.78 (m, 2H), 2.62 (m, 2H), 1.77 (m, 2H), 0.28 (s, 9H). High resolution mass spectrum: For $C_{29}H_{36}N_4O_5SSn$, expected 665.1533 ($^{112}$Sn) and 673.1507 ($^{120}$Sn), found 665.1510 and 673.1505.

2(S)-(4-$^{125}$Iodo-benzenesulfonylamino)-3-{4-[2-(5,6,7,8-tetrahydro-[1,8]naphthyridin-2-yl)-ethyl]-benzoylamino}-propionic Acid (B-5)

A stir bar, methanol (0.05 mL) and an iodobead (Pierce) were added to a shipping vial of Na$^{125}$I (10 mCi, Amersham, IMS300) and stirred for five minutes at room temperature. A solution of B-4 (~0.1 mg) in methanol (0.04 mL) was made and a portion (0.02 mL) was added to a mixture of $H_2SO_4$ (0.005 mL) in methanol (0.025 mL), and this solution was added immediately to the $Na^{125}I$/iodobead vial. After stirring for two minutes at room temperature, the reaction was quenched with $NH_4OH$ (0.04–0.05 mL) and the entire reaction mixture was injected onto the HPLC for purification [Vydac peptide-protein C-18 column, 4.6×250 mm, linear gradient of 10% acetonitrile:$H_2O$ (0.1% TFA) to 90% acetonitrile:$H_2O$ (0.1% TFA) over 20 minutes, 1 mL/min]. The retention time of B-5 is 16 minutes under these conditions. Fractions containing the majority of the radioactivity were pooled, lyophilized and diluted with ethanol to give approximately 1 mCi of B-5, which coeluted on HPLC analysis with an authentic sample of B-3.

Instrumentation: Analytical and preparative HPLC was carried out using a Waters 600E Powerline Multi Solvent Delivery System with 0.1 mL heads with a Rheodyne 7125 injector and a Waters 990 Photodiode Array Detector with a Gilson FC203 Microfraction collector. For analytical and preparative HPLC, a Vydac peptide-protein C-18 column, 4.6×250 mm was used with a C-18 Brownlee modular guard column. The acetonitrile used for the HPLC analyses was Fisher Optima grade. The HPLC radiodetector used was a Beckman 170 Radioisotope detector. A Vydac C-18 protein and peptide column, 3.9×250 mm was used for analytical and preparative HPLC. Solutions of radioactivity were concentrated using a Speedvac vacuum centrifuge. Calibration curves and chemical concentrations were determined using a Hewlett Packard Model 8452A UV/Vis Diode Array Spectrophotometer. Sample radioactivities were determined in a Packard A5530 gamma counter.

The test procedures employed to measure $\alpha v \beta 3$ and $\alpha v \beta 5$ binding and the bone resorption inhibiting activity of the compounds of the present invention are described below.

BONE RESORPTION-PIT ASSAY

When osteoclasts engage in bone resorption, they can cause the formation of pits in the surface of bone that they are acting upon. Therefore, when testing compounds for their ability to inhibit osteoclasts, it is useful to measure the ability of osteoclasts to excavate these resorption pits when the inhibiting compound is present.

Consecutive 200 micron thick cross sections from a 6 mm cylinder of bovine femur diaphysis are cut with a low speed diamond saw (Isomet, Beuler, Ltd., Lake Bluff, Ill.). Bone slices are pooled, placed in a 10% ethanol solution and refrigerated until further use.

Prior to experimentation, bovine bone slices are ultrasonicated twice, 20 minutes each in $H_2O$. Cleaned slices are placed in 96 well plates such that two control lanes and one lane for each drug dosage are available. Each lane represents either triplicate or quadruplicate cultures. The bone slices in 96 well plates are sterilized by UV irradiation. Prior to incubation with osteoclasts, the bone slices are hydrated by the addition of 0.1 ml $\alpha$MEM, pH 6.9 containing 5% fetal bovine serum and 1% penicillin/streptomycin.

Long bones from 7–14 day old rabbits (New Zealand White Hare) are dissected, cleaned of soft tissue and placed in $\alpha$MEM containing 20 mM HEPES. The bones are minced using scissors until the pieces are <1 mm and transferred to a 50 ml tube in a volume of 25 ml. The tube is rocked gently by hand for 60 cycles, the tissue is sedimented for 1 min., and the supernatant is removed. Another 25 ml of medium is added to the tissue and rocked again. The second supernatant is combined with the first. The number of cells is counted excluding erythrocytes (typically ~$2 \times 10^7$ cells/ml).

A cell suspension consisting of $5 \times 10^6$/ml in $\alpha$MEM containing 5% fetal bovine serum, 10 nM $1,25(OH)_2D_3$, and pencillin-streptomycin is prepared. 200 ml aliquots are added to bovine bone slices (200 mm×6 mm) and incubated for 2 hrs. at 37° C. in a humidified 5% $CO_2$ atmosphere. The medium is removed gently with a micropipettor and fresh medium containing test compounds is added. The cultures are incubated for 48 hrs., and assayed for c-telopeptide (fragments of the al chain of type I collagen) by Crosslaps for culture media (Herlev, Denmark).

Bovine bone slices are exposed to osteoclasts for 20–24 hrs and are processed for staining. Tissue culture media is removed from each bone slice. Each well is washed with 200 ml of $H_2O$, and the bone slices are then fixed for 20 minutes in 2.5% glutaraldehyde, 0.1 M cacodylate, pH 7.4. After fixation, any remaining cellular debris is removed by 2 min. ultrasonication in the presence of 0.25 M $NH_4OH$ followed by 2×15 min ultrasonication in $H_2O$. The bone slices are immediately stained for 6–8 min with filtered 1% toluidine blue and 1% borax.

After the bone slices have dried, resorption pits are counted in test and control slices. Resorption pits are viewed in a Microphot Fx (Nikon) fluorescence microscope using a polarizing Nikon IGS filter cube. Test dosage results are compared with controls and resulting $IC_{50}$ values are determined for each compound tested.

The appropriateness of extrapolating data from this assay to mammalian (including human) disease states is supported by the teaching found in Sato, M., et al., *Journal of Bone and Mineral Research*, Vol. 5, No. 1, pp. 31–40, 1990, which is incorporated by reference herein in its entirety. This article teaches that certain bisphosphonates have been used clinically and appear to be effective in the treatment of Paget's disease, hypercalcemia of malignancy, osteolytic lesions produced by bone metastases, and bone loss due to immobilization or sex hormone deficiency. These same bisphosphonates are then tested in the resorption pit assay described above to confirm a correlation between their known utility and positive performance in the assay.

EIB ASSAY

Duong et al., *J. Bone Miner. Res.*, 8: S378 (1993), describes a system for expressing the human integrin $\alpha v \beta 3$. It has been suggested that the integrin stimulates attachment of osteoclasts to bone matrix, since antibodies against the integrin, or RGD-containing molecules, such as echistatin (European Publication 382 451), can effectively block bone resorption.

Reaction Mixture:
1. 175 $\mu$l TBS buffer (50 mM Tris.HCl pH 7.2, 150 mM NaCl, 1% BSA, 1 mM $CaCl_2$, 1 mM $MgCl_2$).
2. 25 ml cell extract (dilute with 100 mM octylglucoside buffer to give 2000 cpm/25 $\mu$l).
3. $^{125}$I-echistatin (25 $\mu$l/50,000 cpm) (see EP 382 451).
4. 25 $\mu$l buffer (total binding) or unlabeled echigtatin (non-specific binding).

The reaction mixture was then incubated for 1 h at room temp. The unbound and the bound $\alpha v \beta 3$ were separated by filtration using a Skatron Cell Harvester. The filters (prewet in 1.5% poly-ethyleneimine for 10 mins) were then washed with the wash buffer (50 mM Tris HCl, 1 mM $CaCl_2/MgCl_2$, pH 7.2). The filter was then counted in a gamma counter.

SPAV3 ASSAY MATERIALS:
1. Wheat germ agglutinin Scintillation Proximity Beads (SPA): Amersham
2. Octylglucopyranoside: Calbiochem
3. HEPES: Calbiochem
4. NaCl: Fisher 5. CaCl$_2$: Fisher
6. MgCl$_2$: SIGMA
7. Phenylmethylsulfonylfluoride (PMSF): SIGMA
8. Optiplate: PACKARD
9. Compound A-10 (specific activity 500–1000 Ci/mmole)
10. test compound
11. Purified integrin receptor: $\alpha v\beta 3$ was purified from 293 cells overexpressing $\alpha v\beta 3$ (Duong et al., *J. Bone Min. Res.*, 8:S378, 1993) according to Pytela (Methods in Enzymology, 144:475, 1987)
12. Binding buffer: 50 mM HEPES, pH 7.8, 100 mM NaCl, 1 mM Ca$^{2+}$/Mg$^{2+}$, 0.5 mM PMSF
13. 50 mM octylglucoside in binding buffer: 50-OG buffer

PROCEDURE:

1. Pretreatment of SPA beads:

500 mg of lyophilized SPA beads were first washed four times with 200 ml of 50-OG buffer and once with 100 ml of binding buffer, and then resuspended in 12.5 ml of binding buffer.

2. Preparation of SPA beads and receptor mixture

In each assay tube, 2.5 μl (40 mg/ml) of pretreated beads were suspended in 97.5 μl of binding buffer and 20 ml of 50-OG buffer. 5 ml (~30 ng/μl) of purified receptor was added to the beads in suspension with stirring at room temperature for 30 minutes. The mixture was then centrifuged at 2,500 rpm in a Beckman GPR Benchtop centrifuge for 10 minutes at 4° C. The pellets were then resuspended in 50 μl of binding buffer and 25 μl of 50-OG buffer.

3. Reaction

The following were sequentially added into Optiplate in corresponding wells:
    (i) Receptor/beads mixture (75 μl)
    (ii) 25 μl of each of the following: compound to be tested, binding buffer for total binding or A-8 for non-specific binding (final concentration 1 μM)
    (iii) A-10 in binding buffer (25 μl, final concentration 40 pM)
    (iv) Binding buffer (125 μl)
    (v) Each plate was sealed with plate sealer from PACKARD and incubated overnight with rocking at 4° C.

4. Plates were counted using PACKARD TOPCOUNT
5. % inhibition was calculated as follows:

A=total counts

B=nonspecific counts

C=sample counts

% inhibition=[{(A−B)−(C−B)}/(A−B)]/(A−B)×100

OCFORM ASSAY

Osteoblast-like cells (1.8 cells), originally derived from mouse calvaria, were plated in CORNING 24 well tissue culture plates in αMEM medium containing ribo- and deoxyribonucleosides, 10% fetal bovine serum and penicillin-streptomycin. Cells were seeded at 40,000/well in the morning. In the afternoon, bone marrow cells were prepared from six week old male Balb/C mice as follows:

Mice were sacrificed, tibiae removed and placed in the above medium. The ends were cut off and the marrow was flushed out of the cavity into a tube with a 1 mL syringe with a 27.5 gauge needle. The marrow was suspended by pipetting up and down. The suspension was passed through >100 mm nylon cell strainer. The resulting suspension was centrifuged at 350×g for seven minutes. The pellet was resuspended, and a sample was diluted in 2% acetic acid to lyse the red cells. The remaining cells were counted in a hemacytometer. The cells were pelleted and resuspended at 1×10$^6$ cells/mL. 50 μL was added to each well of 1.8 cells to yield 50,000 cells/well and 1,25-dihydroxy-vitamin D$_3$ (D$_3$) was added to each well to a final concentration of 10 nM. The cultures were incubated at 37° C. in a humidified, 5% CO$_2$ atmosphere. After 48 h, the medium was changed. 72 h after the addition of bone marrow, test compounds were added with fresh medium containing D$_3$ to quadruplicate wells. Compounds were added again after 48 h with fresh medium containing D$_3$. After an additional 48 h., the medium was removed, cells were fixed with 10% formaldehyde in phosphate buffered saline for 10 minutes at room temperature, followed by a 1–2 minute treatment with ethanol:acetone (1:1) and air dried. The cells were then stained for tartrate resistant acid phosphatase as follows:

The cells were stained for 10–15 minutes at room temperature with 50 mM acetate buffer, pH 5.0 containing 30 mM sodium tartrate, 0.3 mg/mL Fast Red Violet LB Salt and 0.1 mg/mL Naphthol AS-MX phosphate. After staining, the plates were washed extensively with deionized water and air dried. The number of multinucleated, positive staining cells was counted in each well.

SPAV5 ASSAY MATERIALS:

1. Wheat germ agglutinin Scintillation Proximity Beads (SPA): Amersham
2. Octylglucopyranoside and Phorbo-12-myristate-13-acetate (PMA): Calbiochem
3. Tris-HCl, NaCl and CaCl$_2$: Fisher
4. Minimum Essential Media (MEM): Gibco/BRL
5. Fetal bovine serum (FBS): Hyclone
6. MgCl$_2$, MnCl$_2$, and Phenylmethylsulfonylfluoride (PMSF): SIGMA
7. Protease inhibitor cocktail tablets: Boehringer Mannheim.
8. Optiplate-96 wells: PACKARD
9. B-5 was used as radiolabeled ligand (specific activity 500–1000 Ci/mmole) and B-3 (2.5 μM) was used to achieve 100% inhibition.
10. Test compound.
11. HEK293 cells overexpressing $\alpha_v\beta_5$ integrins (Simon et al., J. Biol. Chem. 272, 29380–29389, 1997) are cultured in 150 mm dishes in 10% FBS/MEM media (Gibco/BRL).
12. Lysis buffer: 100 mM octylglucopyranoside, 50 mM Tris, pH 7.5, 100 mM NaCl, 1 mM CaCl$_2$, 1 mM MgCl$_2$, 0.5 mM PMSF and protease inhibitors (1 tablet/50 ml buffer).
13. Binding buffer: 50 mM Tris, pH 7.5, 100 mM NaCl, 1 mM CaCl$_2$ 1 mM MgCl$_2$ and 1 mM MnCl$_2$.
14. 50 mM octylglucopyranoside in binding buffer: 50-OG buffer

PROCEDURE:

1. $\alpha_v\beta_5$-cell lysates: HEK 293 cells expressing $\alpha_v\beta_5$ integrins were cultured until confluent. Cells were then starved overnight in media containing 0.5% FBS, followed by treatment with 100 nM PMA for 20 min. Cells were washed 2 times with cold phosphate buffer saline (4° C.) and solubilized in lysis buffer for 30 min on ice. Lysates were clarified using a Beckman JA-20 at 20,000× g. Protein concentration of clarified lysates was determined using a micro BCA kit (Pierce) and stored in aliquots at 80° C.

2. Pretreatment of SPA beads:

500 mg of lyophilized SPA beads were first washed four times with 200 ml of 50-OG buffer and once with 100 ml of binding buffer, and then resuspended in 12.5 ml of binding buffer.

3. Preparation of SPAV5 binding reaction
   To each assay well, the following were sequentially added into Optiplate plates:
   (i) Binding buffer to make up final volume of 125 μl per well.
   (ii) 3 μl (120 μg/well) of pretreated beads diluted with 22 μl of 50-OG Buffer
   (iii) 15 μg of $\alpha_v\beta_5$-cell lysate proteins.
   (iv) B-5 at 50,000 cpm.
   (v) 25 μl of graded concentrations of test compound.
   (vi) Each plate was sealed with plate sealer from PACKARD and incubated overnight with rocking at 4° C.
4. Plates were counted using PACKARD TOPCOUNT microplate scintillation counter.
5. % Inhibition was calculated as follows:
   A=total counts (binding of receptor to B-5)
   B=nonspecific counts (binding of receptor to B-5 in the presence of 2.5 μM cold ligand)
   C=counts from receptor binding to test compound % inhibition=[{(A−B)−(C−B)}/(A−B)]/(A−B)×100
   $IC_{50}$ of test compound was calculated as 50% of inhibition.

Representative compounds of the present invention were tested and found to bind to human αvβ3 integrin. These compounds were generally found to have $IC_{50}$ values less 10 nM in the SPAV3 assay.

Representative compounds of the present invention were also tested in the SPAV5 assay to determine affinity for the αvβ5 receptor. These compounds were generally found to have $IC_{50}$ values less than 100 nM.

EXAMPLE OF A PHARMACEUTICAL FORMULATION

As a specific embodiment of an oral composition, 100 mg of any of the compounds of the present invention are formulated with sufficient finely divided lactose to provide a total amount of 580 to 590 mg to fill a size O hard gel capsule.

While the invention has been described and illustrated in reference to certain preferred embodiments thereof, those skilled in the art will appreciate that various changes, modifications and substitutions can be made therein without departing from the spirit and scope of the invention. For example, effective dosages other than the preferred doses as set forth hereinabove may be applicable as a consequence of variations in the responsiveness of the mammal being treated for severity of bone disorders caused by resorption, or for other indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be limited only by the scope of the claims which follow and that such claims be interpreted as broadly as is reasonable.

What is claimed is:
1. A compound of the formula

$$W\text{-}Y\text{-}Z\text{-}(CH_2)_3\text{-}C(R^4)(R^5)\text{-}C(R^6)(R^7)\text{-}C(O)OR^8$$

wherein any methylene ($CH_2$) carbon atom of the propylene [$(CH_2)_3$] chain in the formula can be independently substituted by one or two $R^3$ substituents;
W is

[structure showing a bicyclic ring with NH, N, X, and $R^1$ substituent]

wherein the ring carbon atoms are unsubstituted or substituted with one or two $R^1$ substituents;
X is $CH_2$, O, or S;
Y is selected from the group consisting of
   —$(CH_2)_m$—,
   —$(CH_2)_m$—O—$(CH_2)_n$—,
   —$(CH_2)_m$—$NR^2$—$(CH_2)_n$—,
   —$(CH_2)_m$—S—$(CH_2)_n$—,
   —$(CH_2)_m$—SO—$(CH_2)_n$—,
   —$(CH_2)_m$—$SO_2$—$(CH_2)_n$—,
   —$(CH_2)_m$—O—$(CH_2)_n$—O—$(CH_2)_p$—,
   —$(CH_2)_m$—O—$(CH_2)_n$—$NR^2$—$(CH_2)_p$—,
   —$(CH_2)_m$—$NR^2$—$(CH_2)_n$—$NR^2$—$(CH_2)_p$—,
   —$(CH_2)_m$—O—$(CH_2)_n$—S—$(CH_2)_p$—,
   —$(CH_2)_m$—S—$(CH_2)_n$—S—$(CH_2)_p$—,
   —$(CH_2)_m$—$NR^2$—$(CH_2)_n$—S—$(CH_2)_p$—,
   —$(CH_2)_m$—$NR^2$—$(CH_2)_n$—O—$(CH_2)_p$—,
   —$(CH_2)_m$—S—$(CH_2)_n$—O—$(CH_2)_p$—, and
   —$(CH_2)_m$—S—$(CH_2)_n$—$NR^2$—$(CH_2)_p$—,
   wherein any methylene ($CH_2$) carbon atom in Y, other than in $R^2$, can be substituted by one or two $R^3$ substituents;
Z is a 5- or 6-membered heterocyclic ring system having 1 to 3 heteroatoms selected from the group consisting of N, O, and S, and wherein the ring carbon atoms are either unsubstituted or substituted with one or more substituents independently selected from the group consisting of $R^9$, such that two $R^9$ substituents, when on the same carbon atom, are taken together with the carbon atom to which they are attached to form a $C_3$–$C_6$ cycloalkyl group;
$R^1$ is independently selected from the group consisting of hydrogen, halogen, $C_1$–$C_{10}$ alkyl, $C_{3-8}$ cycloalkyl, $C_{3-8}$ cycloheteroalkyl, $C_{3-8}$ cycloalkyl $C_{1-6}$ alkyl, $C_{3-8}$ cycloheteroalkyl $C_{1-6}$ alkyl, aryl, aryl $C_{1-8}$ alkyl, amino, amino $C_{1-8}$ alkyl, $C_{1-3}$ acylamino, $C_{1-3}$ acylamino $C_{1-8}$ alkyl, $(C_{1-6}$ alkyl$)_p$amino, $(C_{1-6}$ alkyl$)_p$ amino $C_{1-8}$ alkyl, $C_{1-4}$ alkoxy, $C_{1-4}$ alkoxy $C_{1-6}$ alkyl, hydroxycarbonyl, hydroxycarbonyl $C_{1-6}$ alkyl, $C_{1-3}$ alkoxycarbonyl, $C_{1-3}$ alkoxycarbonyl $C_{1-6}$ alkyl, hydroxycarbonyl-$C_{1-6}$ alkyloxy, hydroxy, hydroxy $C_{1-6}$ alkyl, $C_{1-6}$ alkyloxy-$C_{1-6}$ alkyl, nitro, cyano, trifluoromethyl, trifluoromethoxy, trifluoroethoxy, $C_{1-8}$ alkyl-S(O)$_p$, $(C_{1-8}$ alkyl$)_p$aminocarbonyl, $C_{1-8}$ alkyloxycarbonylamino, $(C_{1-8}$ alkyl$)_p$ aminocarbonyloxy, (aryl $C_{1-8}$ alkyl$)_p$amino, (aryl$)_p$ amino, aryl $C_{1-8}$-alkylsulfonylamino, and $C_{1-8}$ alkylsulfonylamino;
or two $R^1$ substituents, when on the same carbon atom, are taken together with the carbon atom to which they are attached to form a carbonyl group;

each $R^2$ is independently selected from the group consisting of
hydrogen,
aryl,
aminocarbonyl,
$C_{3-8}$ cycloalkyl,
amino $C_{1-6}$ alkyl,
$(aryl)_p$aminocarbonyl,
$(aryl\ C_{1-5}\ alkyl)_p$aminocarbonyl,
hydroxycarbonyl $C_{1-6}$ alkyl,
$C_{1-8}$ alkyl,
aryl $C_{1-6}$ alkyl,
$(C_{1-6}\ alkyl)_p$amino $C_{2-6}$ alkyl,
$(aryl\ C_{1-6}\ alkyl)_p$amino $C_{2-6}$ alkyl,
$C_{1-8}$ alkylsulfonyl,
$C_{1-8}$ alkoxycarbonyl,
aryloxycarbonyl,
aryl $C_{1-8}$ alkoxycarbonyl,
$C_{1-8}$ alkylcarbonyl,
arylcarbonyl,
aryl $C_{1-6}$ alkylcarbonyl,
$(C_{1-8}\ alkyl)_p$aminocarbonyl,
aminosulfonyl,
$C_{1-8}$ alkylaminosulfonyl,
$(aryl)_p$aminosulfonyl,
$(aryl\ C_{1-8}\ alkyl)_p$aminosulfonyl,
arylsulfonyl,
aryl$C_{1-6}$ alkylsulfonyl,
$C_{1-6}$ alkylthiocarbonyl,
arylthiocarbonyl, and
aryl $C_{1-6}$ alkylthiocarbonyl,
wherein any of the alkyl groups of $R^2$ are either unsubstituted or substituted with one to three $R^1$ substituents;
each $R^3$ is independently selected from the group consisting of
hydrogen,
aryl,
$C_{1-10}$ alkyl,
aryl-$(CH_2)_r$—O—$(CH_2)_s$—,
aryl-$(CH_2)_r$—S(O)$_p$—$(CH_2)_s$—,
aryl-$(CH_2)_r$—C(O)—$(CH_2)_s$—,
aryl-$(CH_2)_r$—C(O)—N($R^2$)—$(CH_2)_s$—,
aryl-$(CH_2)_r$—N($R^2$)—C(O)—$(CH_2)_s$—,
aryl-$(CH_2)_r$—N($R^2$)—$(CH_2)_s$—,
halogen,
hydroxyl,
oxo,
trifluoromethyl,
$C_{1-8}$ alkylcarbonylamino,
aryl $C_{1-5}$ alkoxy,
$C_{1-5}$ alkoxycarbonyl,
$(C_{1-8}\ alkyl)_p$aminocarbonyl,
$C_{1-6}$ alkylcarbonyloxy,
$C_{3-8}$ cycloalkyl,
$(C_{1-6}\ alkyl)_p$amino,
amino $C_{1-6}$ alkyl,
arylaminocarbonyl,
aryl $C_{1-5}$ alkylaminocarbonyl,
aminocarbonyl,
aminocarbonyl $C_{1-6}$ alkyl,
hydroxycarbonyl,
hydroxycarbonyl $C_{1-6}$ alkyl,
HC≡C—$(CH_2)_t$—,
$C_{1-6}$ alkyl-C≡C—$(CH_2)_t$—,
$C_{3-7}$ cycloalkyl-C≡C—$(CH_2)_t$—,
aryl-C≡C—$(CH_2)_t$—,
$C_{1-6}$ alkylaryl-C≡C—$(CH_2)_t$—,
$CH_2$=CH—$(CH_2)_t$—,
$C_{1-6}$ alkyl-CH=CH—$(CH_2)_t$—,
$C_{3-7}$ cycloalkyl-CH=CH—$(CH_2)_t$—,
aryl-CH=CH—$(CH_2)_t$—,
$C_{1-6}$ alkylaryl-CH=CH—$(CH_2)_t$—,
$C_{1-6}$ alkyl-$SO_2$—$(CH_2)_t$—,
$C_{1-6}$ alkylaryl-$SO_2$—$(CH_2)_t$—,
$C_{1-6}$ alkoxy,
aryl $C_{1-6}$ alkoxy,
aryl $C_{1-6}$ alkyl,
$(C_{1-6}\ alkyl)_p$amino $C_{1-6}$ alkyl,
$(aryl)_p$amino,
$(aryl)_p$amino $C_{1-6}$ alkyl,
$(aryl\ C_{1-6}\ alkyl)_p$amino,
$(aryl\ C_{1-6}\ alkyl)_p$amino $C_{1-6}$ alkyl,
arylcarbonyloxy,
aryl $C_{1-6}$ alkylcarbonyloxy,
$(C_{1-6}\ alkyl)_p$aminocarbonyloxy,
$C_{1-8}$ alkylsulfonylamino,
arylsulfonylamino,
$C_{1-8}$ alkylsulfonylamino $C_{1-6}$ alkyl,
arylsulfonylamino $C_{1-6}$ alkyl,
aryl $C_{1-6}$ alkylsulfonylamino,
aryl $C_{1-6}$ alkylsulfonylamino $C_{1-6}$ alkyl,
$C_{1-8}$ alkoxycarbonylamino,
$C_{1-8}$ alkoxycarbonylamino $C_{1-8}$ alkyl,
aryloxycarbonylamino $C_{1-8}$ alkyl,
aryl $C_{1-8}$ alkoxycarbonylamino,
aryl $C_{1-8}$ alkoxycarbonylamino $C_{1-8}$ alkyl,
$C_{1-8}$ alkylcarbonylamino,
$C_{1-8}$ alkylcarbonylamino $C_{1-6}$ alkyl,
arylcarbonylamino $C_{1-6}$ alkyl,
aryl $C_{1-6}$ alkylcarbonylamino,
aryl $C_{1-6}$ alkylcarbonylamino $C_{1-6}$ alkyl,
aminocarbonylamino $C_{1-6}$ alkyl,
$(C_{1-8}\ alkyl)_p$aminocarbonylamino,
$(C_{1-8}\ alkyl)_p$aminocarbonylamino $C_{1-6}$ alkyl,
$(aryl)_p$aminocarbonylamino $C_{1-6}$ alkyl,
$(aryl\ C_{1-8}\ alkyl)_p$aminocarbonylamino,
$(aryl\ C_{1-8}\ alkyl)_p$aminocarbonylamino $C_{1-6}$ alkyl,
aminosulfonylamino $C_{1-6}$ alkyl,
$(C_{1-8}\ alkyl)_p$aminosulfonylamino,
$(C_{1-9}\ alkyl)_p$aminosulfonylamino $C_{1-6}$ alkyl,
$(aryl)_p$aminosulfonylamino $C_{1-6}$ alkyl,
$(aryl\ C_{1-8}\ alkyl)_p$aminosulfonylamino,
$(aryl\ C_{1-8}\ alkyl)_p$aminosulfonylamino $C_{1-6}$ alkyl,
$C_{1-6}$ alkylsulfonyl,
$C_{1-6}$ alkylsulfonyl $C_{1-6}$ alkyl,
arylsulfonyl $C_{1-6}$ alkyl,
aryl $C_{1-6}$ alkylsulfonyl,
aryl $C_{1-6}$ alkylsulfonyl $C_{1-6}$ alkyl,
$C_{1-6}$ alkylcarbonyl,
$C_{1-6}$ alkylcarbonyl $C_{1-6}$ alkyl,
arylcarbonyl $C_{1-6}$ alkyl,
aryl $C_{1-6}$ alkylcarbonyl,
aryl $C_{1-6}$ alkylcarbonyl $C_{1-6}$ alkyl,
$C_{1-6}$ alkylthiocarbonylamino,
$C_{1-6}$ alkylthiocarbonylamino $C_{1-6}$ alkyl,
arylthiocarbonylamino $C_{1-6}$ alkyl,
aryl $C_{1-6}$ alkylthiocarbonylamino,
aryl $C_{1-6}$ alkylthiocarbonylamino $C_{1-6}$ alkyl,
$(C_{1-8}\ alkyl)_p$aminocarbonyl $C_{1-6}$ alkyl, (aryl)$_p$aminocarbonyl C$_{1-6}$ alkyl,
(aryl C$_{1-8}$ alkyl)$_p$aminocarbonyl, and
(aryl C$_{1-8}$ alkyl)$_p$aminocarbonyl C$_{1-6}$ alkyl,
or two R$^3$ substituents, when on the same carbon atom are taken together with the carbon atom to which they are attached to form a carbonyl or cyclopropyl group, wherein any of the alkyl groups of R$^3$ are either unsubstituted or substituted with one to three R$^1$ substituents, and provided that each R$^3$ is selected such that in the resultant compound the carbon atom or atoms to which R$^3$ is attached is itself attached to no more than one heteroatom;

R$^4$ and R$^5$ are each independently selected from the group consisting of
hydrogen,
C$_{1-10}$ alkyl,
aryl,
aryl-(CH$_2$)$_r$—O—(CH$_2$)$_s$—,
aryl-(CH$_2$)$_r$—S(O)$_p$—(CH$_2$)$_s$—,
aryl-(CH$_2$)$_r$—C(O)—(CH$_2$)$_s$—,
aryl-(CH$_2$)$_r$—C(O)—N(R$^2$)—(CH$_2$)$_s$—,
aryl-(CH$_2$)$_r$—N(R$^2$)—C(O)—(CH$_2$)$_s$—,
aryl-(CH$_2$)$_r$—N(R$^2$)—(CH$_2$)$_s$—,
halogen,
hydroxyl,
C$_{1-8}$ alkylcarbonylamino,
aryl C$_{1-5}$ alkoxy,
C$_{1-5}$ alkoxycarbonyl,
(C$_{1-8}$ alkyl)$_p$aminocarbonyl,
C$_{1-6}$ alkylcarbonyloxy,
C$_{3-8}$ cycloalkyl,
(C$_{1-6}$ alkyl)$_p$amino,
amino C$_{1-6}$ alkyl,
arylaminocarbonyl,
aryl C$_{1-5}$ alkylaminocarbonyl,
aminocarbonyl,
aminocarbonyl C$_{1-6}$ alkyl,
hydroxycarbonyl,
hydroxycarbonyl C$_{1-6}$ alkyl,
HC≡C—(CH$_2$)$_t$—,
C$_{1-6}$ alkyl-C≡C—(CH$_2$)$_t$—,
C$_{3-7}$ cycloalkyl-C≡C—(CH$_2$)$_t$—,
aryl-C≡C—(CH$_2$)$_t$—,
C$_{1-6}$ alkylaryl-C≡C—(CH$_2$)$_t$—,
CH$_2$=CH—(CH$_2$)$_t$—,
C$_{1-6}$ alkyl-CH=CH—(CH$_2$)$_t$—,
C$_{3-7}$ cycloalkyl-CH=CH—(CH$_2$)$_t$—,
aryl-CH=CH—(CH$_2$)$_t$—,
C$_{1-6}$ alkylaryl-CH=CH—(CH$_2$)$_t$—,
C$_{1-6}$ alkyl-SO$_2$—(CH$_2$)$_t$—,
C$_{1-6}$ alkylaryl-SO$_2$—(CH$_2$)$_t$—,
C$_{1-6}$ alkoxy,
aryl C$_{1-6}$ alkoxy,
aryl C$_{1-6}$ alkyl,
(C$_{1-6}$ alkyl)$_p$amino C$_{1-6}$ alkyl,
(aryl)$_p$amino,
(aryl)$_p$amino C$_{1-6}$ alkyl,
(aryl C$_{1-6}$ alkyl)$_p$amino,
(aryl C$_{1-6}$ alkyl)$_p$amino C$_{1-6}$ alkyl,
arylcarbonyloxy,
aryl C$_{1-6}$ alkylcarbonyloxy,
(C$_{1-6}$ alkyl)$_p$aminocarbonyloxy,
C$_{1-8}$ alkylsulfonylamino,
arylsulfonylamino,
C$_{1-8}$ alkylsulfonylamino C$_{1-6}$ alkyl,
arylsulfonylamino C$_{1-6}$ alkyl,
aryl C$_{1-6}$ alkylsulfonylamino,
aryl C$_{1-6}$ alkylsulfonylamino C$_{1-6}$ alkyl,
C$_{1-8}$ alkoxycarbonylamino,
C$_{1-8}$ alkoxycarbonylamino C$_{1-8}$ alkyl,
aryloxycarbonylamino C$_{1-8}$ alkyl,
aryl C$_{1-8}$ alkoxycarbonylamino,
aryl C$_{1-8}$ alkoxycarbonylamino C$_{1-8}$ alkyl,
C$_{1-8}$ alkylcarbonylamino,
C$_{1-8}$ alkylcarbonylamino C$_{1-6}$ alkyl,
arylcarbonylamino C$_{1-6}$ alkyl,
aryl C$_{1-6}$ alkylcarbonylamino,
aryl C$_{1-6}$ alkylcarbonylamino C$_{1-6}$ alkyl,
aminocarbonylamino C$_{1-6}$ alkyl,
(C$_{1-8}$ alkyl)$_p$aminocarbonylamino,
(C$_{1-8}$ alkyl)$_p$aminocarbonylamino C$_{1-6}$ alkyl,
(aryl)$_p$aminocarbonylamino C$_{1-6}$ alkyl,
(aryl C$_{1-8}$ alkyl)$_p$aminocarbonylamino,
(aryl C$_{1-8}$ alkyl)$_p$aminocarbonylamino C$_{1-6}$ alkyl,
aminosulfonylamino C$_{1-6}$ alkyl,
(C$_{1-8}$ alkyl)$_p$aminosulfonylamino,
(C$_{1-8}$ alkyl)$_p$aminosulfonylamino C$_{1-6}$ alkyl,
(aryl)$_p$aminosulfonylamino C$_{1-6}$ alkyl,
(aryl C$_{1-8}$ alkyl)$_p$aminosulfonylamino,
(aryl C$_{1-8}$ alkyl)$_p$aminosulfonylamino C$_{1-6}$ alkyl,
C$_{1-6}$ alkylsulfonyl,
C$_{1-6}$ alkylsulfonyl C$_{1-6}$ alkyl,
arylsulfonyl C$_{1-6}$ alkyl,
aryl C$_{1-6}$ alkylsulfonyl,
aryl C$_{1-6}$ alkylsulfonyl C$_{1-6}$ alkyl,
C$_{1-6}$ alkylcarbonyl,
C$_{1-6}$ alkylcarbonyl C$_{1-6}$ alkyl,
arylcarbonyl C$_{1-6}$ alkyl,
aryl C$_{1-6}$ alkylcarbonyl,
aryl C$_{1-6}$ alkylcarbonyl C$_{1-6}$ alkyl,
C$_{1-6}$ alkylthiocarbonylamino,
C$_{1-6}$ alkylthiocarbonylamino C$_{1-6}$ alkyl,
arylthiocarbonylamino C$_{1-6}$ alkyl,
aryl C$_{1-6}$ alkylthiocarbonylamino,
aryl C$_{1-6}$ alkylthiocarbonylamino C$_{1-6}$ alkyl,
(C$_{1-8}$ alkyl)$_p$aminocarbonyl C$_{1-6}$ alkyl,
(aryl)$_p$aminocarbonyl C$_{1-6}$ alkyl,
(aryl C$_{1-8}$ alkyl)$_p$aminocarbonyl, and
(aryl C$_{1-8}$ alkyl)$_p$aminocarbonyl C$_{1-6}$ alkyl;
or R$^4$ and R$^5$ are taken together with the carbon atom to which they are attached to form a carbonyl group, wherein any of the alkyl groups of R$^4$ or R$^5$ are either unsubstituted or substituted with one to three R$^1$ substituents, and provided that each R$^4$ and R$^5$ are selected such that in the resultant compound the carbon atom to which R$^4$ and R$^5$ are attached is itself attached to no more than one heteroatom;

R$^6$ and R$^7$ are each independently selected from the group consisting of
hydrogen,
C$_{1-10}$ alkyl,
aryl,
aryl-(CH$_2$)$_r$—O—(CH$_2$)$_s$—,
aryl-(CH$_2$)$_r$—S(O)$_p$—(CH$_2$)$_s$—,
aryl-(CH$_2$)$_r$—C(O)—(CH$_2$)$_s$—,
aryl-(CH$_2$)$_r$—C(O)—N(R$^2$)—(CH$_2$)$_s$—,
aryl-(CH$_2$)$_r$—N(R$^2$)—C(O)—(CH$_2$)$_s$—,
aryl-(CH$_2$)$_r$—N(R$^2$)—(CH$_2$)$_s$—,
halogen,
hydroxyl,
C$_{1-8}$ alkylcarbonylamino,
aryl C$_{1-5}$ alkoxy,
C$_{1-5}$ alkoxycarbonyl,
(C$_{1-8}$ alkyl)$_p$aminocarbonyl, $C_{1-6}$ alkylcarbonyloxy,
$C_{3-8}$ cycloalkyl,
$(C_{1-6}$ alkyl$)_p$amino,
amino $C_{1-6}$ alkyl,
arylaminocarbonyl,
aryl $C_{1-5}$ alkylaminocarbonyl,
aminocarbonyl,
aminocarbonyl $C_{1-6}$ alkyl,
hydroxycarbonyl,
hydroxycarbonyl $C_{1-6}$ alkyl,
$HC{\equiv}C-(CH_2)_t-$,
$C_{1-6}$ alkyl-$C{\equiv}C-(CH_2)_t-$,
$C_{3-7}$ cycloalkyl-$C{\equiv}C-(CH_2)_t-$,
aryl-$C{\equiv}C-(CH_2)_t-$,
$C_{1-6}$ alkylaryl-$C{\equiv}C-(CH_2)_t-$,
$CH_2{=}CH-(CH_{42})_t-$,
$C_{1-6}$ alkyl-$CH{=}CH-(CH_2)_t-$,
$C_{3-7}$ cycloalkyl-$CH{=}CH-(CH_2)_t-$,
aryl-$CH{=}CH-(CH_2)_t-$,
$C_{1-6}$ alkylaryl-$CH{=}CH-(CH_2)_t-$,
$C_{1-6}$ alkyl-$SO_2-(CH_2)_t-$,
$C_{1-6}$ alkylaryl-$SO_2-(CH_2)_t-$,
$C_{1-6}$ alkoxy,
aryl $C_{1-6}$ alkoxy,
aryl $C_{1-6}$ alkyl,
$(C_{1-6}$ alkyl$)_p$amino $C_{1-6}$ alkyl,
(aryl$)_p$amino,
(aryl$)_p$amino $C_{1-6}$ alkyl,
(aryl $C_{1-6}$ alkyl$)_p$amino,
(aryl $C_{1-6}$ alkyl$)_p$amino $C_{1-6}$ alkyl,
arylcarbonyloxy,
aryl $C_{1-6}$ alkylcarbonyloxy,
$(C_{1-6}$ alkyl$)_p$aminocarbonyloxy,
$C_{1-8}$ alkylsulfonylamino,
arylcarbonylamino,
arylsulfonylamino,
$C_{1-8}$ alkylsulfonylamino $C_{1-6}$ alkyl,
arylsulfonylamino $C_{1-6}$ alkyl,
aryl $C_{1-6}$ alkylsulfonylamino,
aryl $C_{1-6}$ alkylsulfonylamino $C_{1-6}$ alkyl,
$C_{1-8}$ alkoxycarbonylamino,
$C_{1-8}$ alkoxycarbonylamino $C_{1-8}$ alkyl,
aryloxycarbonylamino $C_{1-8}$ alkyl,
aryl $C_{1-8}$ alkoxycarbonylamino,
aryl $C_{1-8}$ alkoxycarbonylamino $C_{1-8}$ alkyl,
$C_{1-8}$ alkylcarbonylamino $C_{1-6}$ alkyl,
arylcarbonylamino $C_{1-6}$ alkyl,
aryl $C_{1-6}$ alkylcarbonylamino,
aryl $C_{1-6}$ alkylcarbonylamino $C_{1-6}$ alkyl,
aminocarbonylamino $C_{1-6}$ alkyl,
$(C_{1-8}$ alkyl$)_p$aminocarbonylamino,
$(C_{1-8}$ alkyl$)_p$aminocarbonylamino $C_{1-6}$ alkyl,
(aryl) paminocarbonylamino $C_{1-6}$ alkyl,
arylaminocarbonylamino,
(aryl $C_{1-8}$ alkyl$)_p$aminocarbonylamino,
(aryl $C_{1-8}$ alkyl$)_p$aminocarbonylamino $C_{1-6}$ alkyl,
aminosulfonylamino $C_{1-6}$ alkyl,
$(C_{1-8}$ alkyl$)_p$aminosulfonylamino,
$(C_{1-8}$ alkyl$)_p$aminosulfonylamino $C_{1-6}$ alkyl,
(aryl$)_p$aminosulfonylamino $C_{1-6}$ alkyl,
(aryl $C_{1-8}$ alkyl$)_p$aminosulfonylamino,
(aryl $C_{1-8}$ alkyl$)_p$aminosulfonylamino $C_{1-6}$ alkyl,
$C_{1-6}$ alkylsulfonyl,
$C_{1-6}$ alkylsulfonyl $C_{1-6}$ alkyl,
arylsulfonyl $C_{1-6}$ alkyl,
aryl $C_{1-6}$ alkylsulfonyl,
aryl $C_{1-6}$ alkylsulfonyl $C_{1-6}$ alkyl,
$C_{1-6}$ alkylcarbonyl,
$C_{1-6}$ alkylcarbonyl $C_{1-6}$ alkyl,
arylcarbonyl $C_{1-6}$ alkyl,
aryl $C_{1-6}$ alkylcarbonyl,
aryl $C_{1-6}$ alkylcarbonyl $C_{1-6}$ alkyl,
$C_{1-6}$ alkylthiocarbonylamino,
$C_{1-6}$ alkylthiocarbonylamino $C_{1-6}$ alkyl,
arylthiocarbonylamino $C_{1-6}$ alkyl,
aryl $C_{1-6}$ alkylthiocarbonylamino,
aryl $C_{1-6}$ alkylthiocarbonylamino $C_{1-6}$ alkyl,
$(C_{1-8}$ alkyl$)_p$aminocarbonyl $C_{1-6}$ alkyl,
(aryl$)_p$aminocarbonyl $C_{1-6}$ alkyl,
(aryl $C_{1-8}$ alkyl$)_p$aminocarbonyl,
(aryl $C_{1-8}$ alkyl$)_p$aminocarbonyl $C_{1-6}$ alkyl, and
$C_{7-20}$ polycyclyl $C_{0-8}$ alkylsulfonylamino;
wherein any of the alkyl groups of $R^6$ and $R^7$ are either unsubstituted or substituted with one to three $R^1$ substituents, and provided that each $R^6$ and $R^7$ are selected such that in the resultant compound the carbon atom to which $R^6$ and $R^7$ are attached is itself attached to no more than one heteroatom;
$R^8$ is selected from the group consisting of
hydrogen,
$C_{1-8}$ alkyl,
aryl,
aryl $C_{1-8}$ alkyl,
$C_{1-8}$ alkylcarbonyloxy $C_{1-4}$ alkyl,
aryl $C_{1-8}$ alkylcarbonyloxy $C_{1-4}$ alkyl,
$C_{1-8}$ alkylaminocarbonylmethylene, and
$C_{1-8}$ dialkylaminocarbonylmethylene;
$R^9$ is selected from the group consisting of
hydrogen,
$C_{1-8}$ alkyl,
aryl,
halogen,
hydroxyl,
oxo,
aminocarbonyl,
$C_{3-8}$ cycloalkyl,
amino $C_{1-6}$ alkyl,
(aryl$)_p$aminocarbonyl,
hydroxycarbonyl,
(aryl $C_{1-5}$ alkyl$)_p$aminocarbonyl,
hydroxycarbonyl $C_{1-6}$ alkyl,
aryl $C_{1-6}$ alkyl,
$(C_{1-6}$ alkyl$)_p$amino $C_{1-6}$ alkyl,
(aryl $C_{1-6}$ alkyl$)_p$amino $C_{2-6}$ alkyl,
$C_{1-8}$ alkylsulfonyl,
$C_{1-8}$ alkoxycarbonyl,
aryloxycarbonyl,
aryl $C_{1-8}$ alkoxycarbonyl,
$C_{1-8}$ alkylcarbonyl,
arylcarbonyl,
aryl $C_{1-6}$ alkylcarbonyl,
$(C_{1-8}$ alkyl$)_p$aminocarbonyl,
aminosulfonyl,
$C_{1-8}$ alkylaminosulfonyl,
(aryl$)_p$aminosulfonyl,
(aryl $C_{1-8}$ alkyl$)_p$aminosulfonyl,
$C_{1-6}$ alkylsulfonyl,
arylsulfonyl,
aryl $C_{1-6}$ alkylsulfonyl,
aryl $C_{1-6}$ alkylcarbonyl,
$C_{1-6}$ alkylthiocarbonyl,
arylthiocarbonyl,
aryl $C_{1-6}$ alkylthiocarbonyl,
aryl-$(CH_2)_r-O-(CH_2)_s-$, aryl-(CH$_2$)$_r$—S(O)$_p$—(CH$_2$)$_s$—,
aryl-(CH$_2$)$_r$—C(O)—(CH$_2$)$_s$—,
aryl-(CH$_2$)$_r$—C(O)—N(R$^2$)—(CH$_2$)$_s$—,
aryl-(CH$_2$)$_r$—N(R$^2$)—C(O)—(CH$_2$)$_s$—,
aryl-(CH$_2$)$_r$—N(R$^2$)—(CH$_2$)$_s$—,
HC≡C—(CH$_2$)$_t$—,
C$_{1-6}$ alkyl-C≡C—(CH$_2$)$_t$—,
C$_{3-7}$ cycloalkyl-C≡C—(CH$_2$)$_t$—,
aryl-C≡C—(CH$_2$)$_t$—,
C$_{1-6}$ alkylaryl-C≡C—(CH$_2$)$_t$—,
CH$_2$=CH—(CH$_2$)$_t$—,
C$_{1-6}$ alkyl-CH=CH—(CH$_2$)$_t$—,
C$_{3-7}$ cycloalkyl-CH=CH—(CH$_2$)$_t$—,
aryl-CH=CH—(CH$_2$)$_t$—,
C$_{1-6}$ alkylaryl-CH=CH—(CH$_2$)$_t$—,
C$_{1-6}$ alkyl-SO$_2$—(CH$_2$)$_t$—,
C$_{1-6}$ alkylaryl-SO$_2$—(CH$_2$)$_t$—,
C$_{7-20}$ polycyclyl C$_{0-8}$ alkylsulfonylamino C$_{0-6}$ alkyl,
C$_{7-20}$ polycyclyl C$_{0-8}$ alkylcarbonylamino C$_{0-6}$ alkyl,
C$_{7-20}$ polycyclyl C$_{0-8}$ alkylaminosulfonyolamino C$_{0-6}$ alkyl,
C$_{7-20}$ polycyclyl C$_{0-8}$ alkylaminocarbonylamino C$_{0-6}$ alkyl,
C$_{7-20}$ polycyclyl C$_{0-8}$ alkyloxycarbonylamino C$_{0-6}$ alkyl,
C$_{1-8}$ alkylcarbonylamino,
aryl C$_{1-5}$ alkoxy,
C$_{1-5}$ alkoxycarbonyl,
(C$_{1-8}$ alkyl)$_p$aminocarbonyl,
C$_{1-6}$ alkylcarbonyloxy,
(C$_{1-6}$ alkyl)$_p$amino,
aminocarbonyl C$_{1-6}$ alkyl,
C$_{1-6}$ alkoxy,
aryl C$_{1-6}$ alkoxy,
(aryl)$_p$amino,
(aryl)$_p$amino C$_{1-6}$ alkyl,
(aryl C$_{1-6}$ alkyl)$_p$amino,
(aryl C$_{1-6}$ alkyl)$_p$amino C$_{1-6}$ alkyl,
arylcarbonyloxy,
aryl C$_{1-6}$ alkylcarbonyloxy,
(C$_{1-6}$ alkyl)$_p$aminocarbonyloxy,
C$_{1-8}$ alkylsulfonylamino,
arylsulfonylamino,
C$_{1-8}$ alkylsulfonylamino C$_{1-6}$ alkyl,
arylsulfonylamino C$_{1-6}$ alkyl,
aryl C$_{1-6}$ alkylsulfonylamino,
aryl C$_{1-6}$ alkylsulfonylamino C$_{1-6}$ alkyl,
C$_{1-8}$ alkoxycarbonylamino,
C$_{1-8}$ alkoxycarbonylamino C$_{1-8}$ alkyl,
aryloxycarbonylamino C$_{1-8}$ alkyl,
aryl C$_{1-8}$ alkoxycarbonylamino,
aryl C$_{1-8}$ alkoxycarbonylamino C$_{1-8}$ alkyl,
C$_{1-8}$ alkylcarbonylamino,
C$_{1-8}$ alkylcarbonylamino C$_{1-6}$ alkyl,
arylcarbonylamino C$_{1-6}$ alkyl,
aryl C$_{1-6}$ alkylcarbonylamino,
aryl C$_{1-6}$ alkylcarbonylamino C$_{1-6}$ alkyl,
aminocarbonylamino C$_{1-6}$ alkyl,
(C$_{1-8}$ alkyl)$_p$aminocarbonylamino,
(C$_{1-8}$ alkyl)$_p$aminocarbonylamino C$_{1-6}$ alkyl,
(aryl)$_p$aminocarbonylamino C$_{1-6}$ alkyl,
(aryl C$_{1-8}$ alkyl)$_p$aminocarbonylamino,
(aryl C$_{1-8}$ alkyl)$_p$aminocarbonylamino C$_{1-6}$ alkyl,
aminosulfonylamino C$_{1-6}$ alkyl,
(C$_{1-8}$ alkyl)$_p$aminosulfonylamino,
(C$_{1-8}$ alkyl)$_p$aminosulfonylamino C$_{1-6}$ alkyl,
(aryl)$_p$aminosulfonylamino C$_{1-6}$ alkyl,
(aryl C$_{1-8}$ alkyl)$_p$aminosulfonylamino,
(aryl C$_{1-8}$ alkyl)$_p$aminosulfonylamino C$_{1-6}$ alkyl,
C$_{1-6}$ alkylsulfonyl,
C$_{1-6}$ alkylsulfonyl C$_{1-6}$ alkyl,
arylsulfonyl C$_{1-6}$ alkyl,
aryl C$_{1-6}$ alkylsulfonyl,
aryl C$_{1-6}$ alkylsulfonyl C$_{1-6}$ alkyl,
C$_{1-6}$ alkylcarbonyl,
C$_{1-6}$ alkylcarbonyl C$_{1-6}$ alkyl,
arylcarbonyl C$_{1-6}$ alkyl,
aryl C$_{1-6}$ alkylcarbonyl,
aryl C$_{1-6}$ alkylcarbonyl C$_{1-6}$ alkyl,
C$_{1-6}$ alkylthiocarbonylamino,
C$_{1-6}$ alkylthiocarbonylamino C$_{1-6}$ alkyl,
arylthiocarbonylamino C$_{1-6}$ alkyl,
aryl C$_{1-6}$ alkylthiocarbonylamino,
aryl C$_{1-6}$ alkylthiocarbonylamino C$_{1-6}$ alkyl,
(C$_{1-8}$ alkyl)$_p$aminocarbonyl C$_{1-6}$ alkyl,
(aryl)$_p$aminocarbonyl C$_{1-6}$ alkyl,
(aryl C$_{1-8}$ alkyl)$_p$aminocarbonyl, and
(aryl C$_{1-8}$ alkyl)$_p$aminocarbonyl C$_{1-6}$ alkyl;

and wherein any of the alkyl groups of R$^9$ are either unsubstituted or substituted with one to three R$^1$ substituents;

wherein each m is independently an integer from 0 to 3;
each n is independently an integer from 0 to 3;
each p is independently an integer from 0 to 2;
each r is independently an integer from 0 to 3;
each s is independently an integer from 0 to 3; and
each t is independently an integer from 0 to 3;
or a pharmaceutically acceptable salt thereof.

2. The compound of claim 1 wherein
Z is selected from the group consisting of

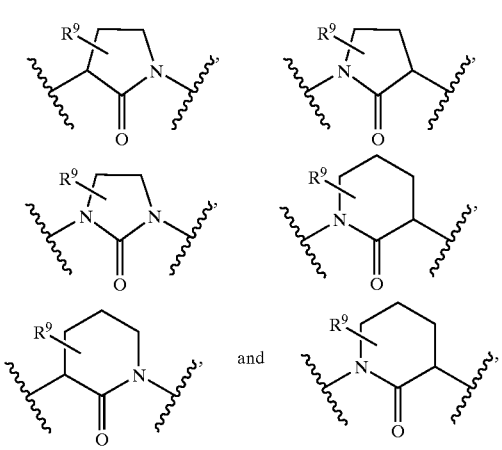

wherein the ring carbon atoms are either unsubstituted or substituted with one to three substituents independently selected from the group consisting of R$^9$.

3. The compound of claim 2 wherein Z is selected from the group consisting of

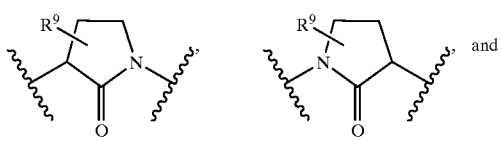

and

-continued

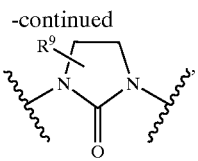

wherein the ring carbon atoms are either unsubstituted or substituted with one to three substituents independently selected from the group consisting of $R^9$.

4. The compound of claim 3 wherein W is

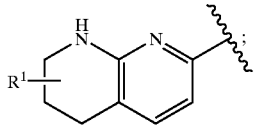

Y is selected from the group consisting of
—$(CH_2)_m$—,
—$(CH_2)_m$—O—$(CH_2)_n$—,
—$(CH_2)_m$—$NR^2$—$(CH_2)_n$—,
—$(CH_2)_m$—S—$(CH_2)_n$—,
—$(CH_2)_m$—SO—$(CH_2)_n$—,
—$(CH_2)_m$—$SO_2$—$(CH_2)_n$—,
—$(CH_2)_m$—O—$(CH_2)_n$—O—$(CH_2)_p$—,
—$(CH_2)_m$—O—$(CH_2)_n$—$NR^2$—$(CH_2)_p$—,
—$(CH_2)_m$—$NR^2$—$(CH_2)_n$—$NR^2$—$(CH_2)_p$—, and
—$(CH_2)_m$—$NR^2$—$(CH_2)_n$—O—$(CH_2)_p$—,
wherein any carbon atom in Y, other than in $R^2$, can be substituted by one or two $R^3$ substituents;
and Z is

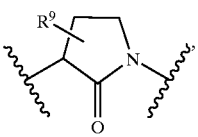

wherein the ring carbon atoms are either unsubstituted or substituted with one to three substituents independently selected from the group consisting of $R^9$.

5. The compound of claim 4 wherein Y is selected from the group consisting of
$(CH_2)_m$, $(CH_2)_m$—O—$(CH_2)_n$, and $(CH_2)_m$—$NR^2$—$(CH_2)_n$,
wherein any methylene ($CH_2$) carbon atom in Y, other than in $R^2$, can be substituted by one or two $R^3$ substituents, and
m is an integer from 0–2, and
n is an integer from 0–1.

6. The compound of claim 5 wherein each $R^2$ is independently selected from the group consisting of
hydrogen,
aryl,
$C_{3-8}$ cycloalkyl,
$C_{1-8}$ alkyl,
$C_{1-8}$ alkylcarbonyl,
arylcarbonyl,
$C_{1-6}$ alkylsulfonyl,
arylsulfonyl,
aryl$C_{1-6}$alkylsulfonyl,
aryl$C_{1-6}$alkylcarbonyl,
$C_{1-8}$alkylaminocarbonyl,
aryl$C_{1-5}$alkylaminocarbonyl,
aryl$C_{1-8}$alkoxycarbonyl, and
$C_{1-8}$alkoxycarbonyl; and
each $R^3$ is independently selected from the group consisting of
hydrogen,
fluoro,
trfluorcomethyl,
aryl,
$C_{1-8}$ alkyl,
aryl $C_{1-6}$ alkyl,
hydroxyl,
oxo,
arylaminocarbonyl,
aryl $C_{1-5}$ alkylaminocarbonyl,
aminocarbonyl, and
aminocarbonyl $C_{1-6}$ alkyl.

7. The compound of claim 6 wherein $R^5$, $R^6$, and $R^7$ are each hydrogen and $R^4$ is selected from the group consisting of
hydrogen,
aryl,
$C_{1-8}$ alkyl,
aryl-C≡C—$(CH_2)_t$—,
aryl $C_{1-6}$ alkyl,
$CH_2$=CH—$(CH_2)_t$—, and
HC≡C—$(CH_2)_t$—.

8. The compound of claim 7 wherein $R^8$ is selected from the group consisting of hydrogen, methyl, and ethyl.

9. The compound of claim 8 wherein $R^8$ is hydrogen.

10. The compound of claim 6 wherein $R^4$, $R^5$, and $R^7$ are each hydrogen and $R^6$ is selected from the group consisting of
hydrogen,
aryl,
$C_{1-8}$ alkylcarbonylamino,
$C_{1-8}$ alkylsulfonylamino,
arylcarbonylamino,
arylsulfonylamino,
$C_{1-8}$ alkylsulfonylamino $C_{1-6}$ alkyl,
arylsulfonylamino $C_{1-6}$ alkyl,
aryl $C_{1-6}$ alkylsulfonylamino,
aryl $C_{1-6}$ alkylsulfonylamino $C_{1-6}$ alkyl,
$C_{1-8}$ alkoxycarbonylamino,
$C_{1-8}$ alkoxycarbonylamino $C_{1-8}$ alkyl,
aryloxycarbonylamino $C_{1-8}$ alkyl,
aryl $C_{1-8}$ alkoxycarbonylamino,
aryl $C_{1-8}$ alkoxycarbonylamino $C_{1-8}$ alkyl,
$C_{1-8}$ alkylcarbonylamino $C_{1-6}$ alkyl,
arylcarbonylamino $C_{1-6}$ alkyl,
aryl $C_{1-6}$ alkylcarbonylamino,
aryl $C_{1-6}$ alkylcarbonylamino $C_{1-6}$ alkyl,
aminocarbonylamino $C_{1-6}$ alkyl,
$(C_{1-8}$ alkyl$)_p$aminocarbonylamino,
$(C_{1-8}$ alkyl$)_p$aminocarbonylamino $C_{1-6}$ alkyl,
(aryl$)_p$aminocarbonylamino $C_{1-6}$ alkyl,
arylaminocarbonylamino, (aryl $C_{1-8}$ alkyl)$_p$aminocarbonylamino,
(aryl $C_{1-8}$ alkyl)$_p$aminocarbonylamino $C_{1-6}$ alkyl,
aminosulfonylamino $C_{1-6}$ alkyl,
($C_{1-8}$ alkyl)$_p$aminosulfonylamino,
($C_{1-8}$ alkyl)$_p$aminosulfonylamino $C_{1-6}$ alkyl,
(aryl)$_p$aminosulfonylamino $C_{1-6}$ alkyl,
(aryl $C_{1-8}$ alkyl)$_p$aminosulfonylamino,
(aryl $C_{1-8}$ alkyl)$_p$aminosulfonylamino $C_{1-6}$ alkyl,
$C_{1-6}$ alkylthiocarbonylamino,
$C_{1-6}$ alkylthiocarbonylamino $C_{1-6}$ alkyl,
arylthiocarbonylamino $C_{1-6}$ alkyl,
aryl $C_{1-6}$ alkylthiocarbonylamino, and
aryl $C_{1-6}$ alkylthiocarbonylamino $C_{1-6}$ alkyl.

11. The compound of claim 10 wherein $R^6$ is selected from the group consisting of
hydrogen,
aryl,
$C_{1-8}$ alkylcarbonylamino,
aryl $C_{1-6}$ alkylcarbonylamino,
arylcarbonylamino,
$C_{1-8}$ alkylsulfonylamino,
aryl $C_{1-6}$ alkylsulfonylamino,
arylsulfonylamino,
$C_{1-8}$ alkoxycarbonylamino,
aryl $C_{1-8}$ alkoxycarbonylamino,
arylaminocarbonylamino,
($C_{1-8}$ alkyl)$_p$aminocarbonylamino,
(aryl $C_{1-8}$ alkyl)$_p$aminocarbonylamino,
($C_{1-8}$ alkyl)$_p$aminosulfonylamino, and
(aryl $C_{1-8}$ alkyl)$_p$aminosulfonylamino.

12. The compound of claim 11 wherein $R^8$ is selected from the group consisting of hydrogen, methyl, and ethyl.

13. The compound of claim 12 wherein $R^8$ is hydrogen.

14. The compound of claim 11 selected from the group consisting of:

3(R or S)-(6-Methoxy-pyridin-3-yl)-6-{2-oxo-3(R)-[2-(5,6,7,8-tetrahydro-[1,8]naphthyridin-2-yl)-ethyl]-pyrrolidin-1-yl}hexanoic acid;

3(S or R)-(6-Methoxy-pyridin-3-yl)-6-{2-oxo-3(R)-[2-(5,6,7,8-tetrahydro-[1,8]naphthyridin-2-yl)-ethyl]-pyrrolidin-1-yl}hexanoic acid;

3(R or S)-(6-Methoxy-pyridin-3-yl)-6-{2-oxo-3(S)-[2-(5,6,7,8-tetrahydro-[1,8]naphthyridin-2-yl)-ethyl]-pyrrolidin-1-yl}hexanoic acid;

3(S or R)-(6-Methoxy-pyridin-3-yl)-6-{2-oxo-3(S)-[2-(5,6,7,8-tetrahydro-[1,8]naphthyridin-2-yl)-ethyl]-pyrrolidin-1-yl}hexanoic acid;

3(S or R)-(6-Methoxy-pyridin-3-yl)-6-{5(S or R)-methyl-2-oxo-3(S)-[(5,6,7,8-tetrahydro-[1,8]naphthyridin-2-yl)-ethyl]-pyrrolidin-1-yl}hexanoic acid;

3(S or R)-(6-Methoxy-pyridin-3-yl)-6-{5(R or S)-methyl-2-oxo-3(S)-[(5,6,7,8-tetrahydro-[1,8]naphthyridin-2-yl)-ethyl]-pyrrolidin-1-yl}hexanoic acid;

3(S)-(6-Methoxy-pyridin-3-yl)-6-{5(R)-methyl-2-oxo-3(S)-[(5,6,7,8-tetrahydro-[1,8]naphthyridin-2-ylmethyl)-amino]-pyrrolidin-1-yl}-hexanoic acid;

3(S)-(2-Methyl-pyrimidin-5-yl)-6-{5(R)-methyl-2-oxo-3(S)-[(5,6,7,8-tetrahydro-[1,8]naphthyridin-2-ylmethyl)-amino]-pyrrolidin-1-yl}-hexanoic acid;

3(R or S)-(2-Methoxy-pyrimidin-5-yl)-6-{2-oxo-3(S)-[2-(5,6,7,8-tetrahydro-[1,8]naphthyridin-2-yl)-ethyl]-pyrrolidin-1-yl}hexanoic acid;

3(S or R)-(2-Methoxy-pyrimidin-5-yl)-6-{5(S or R)-methyl-2-oxo-3(S)-[(5,6,7,8-tetrahydro-[1,8]naphthyridin-2-yl)-ethyl]-pyrrolidin-1-yl}hexanoic acid, and 3(S or R)-(2-Methoxy-pyrimidin-5-yl)-6-{5(R or S)-methyl-2-oxo-3(S)-[(5,6,7,8-tetrahydro-[1,8]naphthyridin-2-yl)-ethyl]-pyrrolidin-1-yl }hexanoic acid; or a pharmaceutically acceptable salt thereof.

15. A pharmaceutical composition comprising a therapeutically effective amount of a compound according to claim 1 and a pharmaceutically acceptable carrier.

16. A method of inhibiting bone resorption in a mammal in need thereof, comprising administering to the mammal a therapeutically effective amount of the composition of claim 15.

17. A method of treating or preventing osteoporosis in a mammal in need thereof, comprising administering to the mammal a therapeutically effective amount of the composition of claim 15.

18. A method of inhibiting a condition selected from the group consisting of bone resorption, restenosis, angiogenesis, diabetic retinopathy, macular degeneration, and inflammatory arthritis, comprising administering to a mammal in need thereof a therapeutically effective amount of a compound according to claim 1.

19. A method of treating or preventing osteoporosis in a mammal in need thereof, comprising administering to the mammal a therapeutically or prophylactically effective amount of a compound according to claim 1.

20. A method of treating or preventing osteoporosis which comprises administering to a mammal in need of such treatment or prevention a therapeutically or prophylactically effective amount of a compound of claim 1 in combination with an effective amount of an organic bisphosphonate or a pharmaceutically acceptable salt or ester thereof.

21. The method of claim 20 wherein said organic bisphosphonate or pharmaceutically acceptable salt or ester thereof is alendronate monosodium trihydrate.

* * * * *